(12) United States Patent
Parham et al.

(10) Patent No.: US 9,040,172 B2
(45) Date of Patent: May 26, 2015

(54) MATERIALS FOR ORGANIC ELECTROLUMINESCENT DEVICES

(75) Inventors: Amir Hossain Parham, Frankfurt am Main (DE); Christof Pflumm, Frankfurt am Main (DE); Teresa Mujica-Fernaud, Darmstadt (DE); Arne Buesing, Frankfurt am Main (DE); Holger Heil, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 479 days.

(21) Appl. No.: 13/379,879

(22) PCT Filed: Jun. 1, 2010

(86) PCT No.: PCT/EP2010/003324
§ 371 (c)(1),
(2), (4) Date: Dec. 21, 2011

(87) PCT Pub. No.: WO2011/000455
PCT Pub. Date: Jan. 6, 2011

(65) Prior Publication Data
US 2012/0097899 A1    Apr. 26, 2012

(30) Foreign Application Priority Data
Jun. 30, 2009   (DE) .......................... 10 2009 031 021

(51) Int. Cl.
| | | |
|---|---|---|
| H01L 51/54 | (2006.01) | |
| C09B 57/00 | (2006.01) | |
| C07D 401/04 | (2006.01) | |
| C07D 403/04 | (2006.01) | |
| C07D 403/14 | (2006.01) | |
| C07D 471/04 | (2006.01) | |
| C07D 487/04 | (2006.01) | |
| C07D 487/14 | (2006.01) | |
| C07D 498/04 | (2006.01) | |
| C07D 513/04 | (2006.01) | |
| H01L 51/00 | (2006.01) | |
| H01L 51/50 | (2006.01) | |

(52) U.S. Cl.
CPC .............. *C09B 57/00* (2013.01); *C07D 401/04* (2013.01); *C07D 403/04* (2013.01); *C07D 403/14* (2013.01); *C07D 471/04* (2013.01); *C07D 487/04* (2013.01); *C07D 487/14* (2013.01); *C07D 498/04* (2013.01); *C07D 513/04* (2013.01); *H01L 51/0067* (2013.01); *H01L 51/0072* (2013.01); *H01L 51/5016* (2013.01); *Y02E 10/549* (2013.01); *Y10S 428/917* (2013.01)

(58) Field of Classification Search
None
See application file for complete search history.

(56) References Cited

U.S. PATENT DOCUMENTS

| | | |
|---|---|---|
| 5,843,607 A | 12/1998 | Hu et al. |
| 2002/0132134 A1 | 9/2002 | Hu et al. |
| 2008/0145708 A1 | 6/2008 | Heil et al. |
| 2008/0220285 A1* | 9/2008 | Vestweber et al. ............ 428/690 |
| 2010/0148161 A1 | 6/2010 | Kai et al. |
| 2010/0187977 A1* | 7/2010 | Kai et al. ...................... 313/504 |
| 2012/0068170 A1 | 3/2012 | Pflumm et al. |

FOREIGN PATENT DOCUMENTS

| | | |
|---|---|---|
| EP | 2301926 A1 | 3/2011 |
| JP | 2006339577 A | 12/2006 |
| JP | 2012-528088 | 11/2012 |
| WO | WO-2006/108497 A1 | 10/2006 |
| WO | WO-2008/056746 A1 | 5/2008 |
| WO | WO-2008/146839 A1 | 12/2008 |
| WO | WO-2009/148015 A1 | 12/2009 |

OTHER PUBLICATIONS

Nozaki et al., Synthesis, Structures, and Properties of Unsymmetrical Heteroacenes Containing Both Pyrrole and Furan Rings, 2008, Organic Letters, vol. 10, No. 6, pp. 1199-1202.*
Sonntag, et al., "Synthesis and Characterization of Novel Conjugated Bisindenocarbazoles", Tetrahedron, vol. 62, (2006), pp. 8103-8108.

* cited by examiner

*Primary Examiner* — Gregory Clark
(74) *Attorney, Agent, or Firm* — Drinker Biddle & Reath LLP

(57) ABSTRACT

The present invention describes novel indenofluorene derivatives which can preferably be employed as matrix materials for phosphorescent dopants or as electron-transport materials, in particular for use in the emission and/or charge-transport layer of electroluminescent devices. The invention furthermore relates to polymers which comprise these compounds as structural units and to a process for the preparation of the compounds according to the invention and to electronic devices which comprise same.

16 Claims, No Drawings

MATERIALS FOR ORGANIC ELECTROLUMINESCENT DEVICES

RELATED APPLICATIONS

This application is a national stage application (under 35 U.S.C. §371) of PCT/EP2010/003324, filed Jun. 1, 2010, which claims benefit of German Application No. 10 2009 031 021.5, filed Jun. 30, 2009.

The present invention describes indenocarbazole derivatives which can preferably be employed as matrix materials for phosphorescent dopants or as electron-transport materials, in particular for use in the emission and/or charge-transport layer of electroluminescent devices. The invention furthermore relates to polymers which comprise these compounds as structural units and to a process for the preparation of the compounds according to the invention and to electronic devices which comprise these compounds.

Organic semiconductors are being developed for a number of electronic applications of different types. The structure of organic electroluminescent devices (OLEDs), in which these organic semiconductors are employed as functional materials, is described, for example, in U.S. Pat. No. 4,539,507, U.S. Pat. No. 5,151,629, EP 0676461 and WO 98/27136. However, further improvements are still necessary. Thus, there is still a need for improvement, in particular, with respect to the lifetime, efficiency and operating voltage of organic electroluminescent devices. It is furthermore necessary for the compounds to have high thermal stability and a high glass-transition temperature and to be sublimable without decomposition.

Improvements in the above-mentioned properties are still necessary, in particular in the case of phosphorescent electroluminescent devices. In particular, there is a need for improvement in matrix materials for phosphorescent emitters which simultaneously result in good efficiency, a long lifetime and a low operating voltage. The properties of the matrix materials in particular are frequently limiting for the lifetime and the efficiency of the organic electroluminescent device.

Carbazole derivatives, for example bis(carbazolyl)biphenyl, are frequently used as matrix materials in accordance with the prior art. There is still a need for improvement here, in particular, with respect to the lifetime and glass-transition temperature of the materials.

Furthermore, ketones (WO 2004/093207, WO 2010/006680), phosphine oxides and sulfones (WO 2005/003253) are used as matrix materials for phosphorescent emitters. In particular with ketones, low operating voltages and long lifetimes are achieved. There is still a need for improvement here, in particular, with respect to the efficiency and compatibility with metal complexes which contain ketoketonate ligands, for example acetylacetonate.

Furthermore, metal complexes, for example BAlq or zinc (II) bis[2-(2-benzothiazolyl)phenoxide], are used as matrix materials for phosphorescent emitters. There is still a need for improvement here, in particular, with respect to the operating voltage and chemical stability. Purely organic compounds are frequently more stable than these metal complexes. Thus, some of these metal complexes are sensitive to hydrolysis, which makes handling of the complexes more difficult.

In particular, there is still a need for improvement in matrix materials for phosphorescent emitters which simultaneously result in high efficiencies, long lifetimes and low operating voltages and which are also compatible with phosphorescent emitters which carry ketoketonate ligands.

Improvements in the properties are likewise also still desirable in the case of electron-transport materials, since the properties of the electron-transport material in particular also have an essential influence on the above-mentioned properties of the organic electroluminescent device. In particular, there is a need for improvement in electron-transport materials which simultaneously result in good efficiency, a long lifetime and a low operating voltage.

It would be desirable here to have available electron-transport materials which result in better electron injection into the emitting layer, since an electron-richer emission layer results in better efficiency. In addition, better injection enables the operating voltage to be reduced. Further improvements in the electron-transport material are therefore necessary for this purpose.

Electroluminescent devices which use $AlQ_3$ as electron conductor have been known for some time and were described as long ago as 1993 in U.S. Pat. No. 4,539,507. $AlQ_3$ has since then frequently been used as electron-transport material, but has a number of disadvantages: it cannot be vapour-deposited without leaving a residue since it partially decomposes at the sublimation temperature, which represents a major problem, in particular, for production plants. This has the consequence that the vapour-deposition sources frequently have to be cleaned or exchanged. Furthermore, decomposition products of $AlQ_3$ enter the OLED, where they contribute to a shortened lifetime and reduced quantum and power efficiency. In addition, $AlQ_3$ has low electron mobility, which results in higher voltages and thus in lower power efficiency. In order to avoid short circuits in the display, it would be desirable to increase the layer thickness; this is not possible with $AlQ_3$ owing to the low charge-carrier mobility and the resultant increase in voltage. The charge-carrier mobility of other electron conductors (U.S. Pat. No. 4,539,507) is likewise too low for thicker layers to be built up therewith, with the lifetime of the OLED being even worse than on use of $AlQ_3$. The inherent colour (yellow in the solid state) of $AlQ_3$, which can result in colour shifts, especially in the case of blue OLEDs, due to reabsorption and weak re-emission, also proves unfavourable. Blue OLEDs can only be produced here with considerable adverse effects on efficiency and colour location.

There thus continues to be a demand for electron-transport materials which result in good efficiencies and at the same time in long lifetimes in organic electroluminescent devices. Surprisingly, it has now been found that organic electroluminescent devices which comprise certain indenofluorene derivatives—indicated below—as electron-transport materials have significant improvements over the prior art. Using these materials, it is possible simultaneously to obtain high efficiencies and long lifetimes, which is not possible using materials in accordance with the prior art. In addition, it has been found that the operating voltages can additionally be significantly reduced, which corresponds to higher power efficiencies.

It has furthermore been found that electronic devices which comprise these indenofluorene derivatives as electron-transport materials in combination with an organic alkali metal compound have significant improvements over the prior art. Using this material combination, high efficiencies and long lifetimes are achieved and at the same time the operating voltages are reduced.

EP 1860097, WO 2006/100896, DE 102006025846, WO 2006/122630, WO 2008/132103, WO 2008/006449, WO 2008/056746, WO 2008/149691, WO 2008/146839 and WO 2008/006449 disclose indenofluorene derivatives for use in electronic devices. Good lifetimes on use as hole-transport material or as deep-blue emitter are cited therein. However, some of these compounds have the problem that, due to the crystallinity of the materials, they crystallise on the vapour-deposition source during vapour deposition in mass production and clog the vapour-deposition source. The use of these materials in production is therefore associated with increased technical complexity. Further improvements are therefore still desirable here.

Consequently, there continues to be a demand both for improved matrix materials for phosphorescent dopants which are suitable for improving the efficiency of organic electroluminescent devices, simultaneously result in long lifetimes and can be processed industrially without problems, and also for improved electron-transport materials.

The object of the present invention thus consists in the provision of such compounds.

Surprisingly, it has been found that electroluminescent devices which use indenocarbazole derivatives according to the invention have significant improvements over the prior art, in particular on use as matrix materials for phosphorescent dopants or as electron-transport materials. On the one hand longer lifetimes, on the other hand lower operating voltages arise due to changes in the interfacial morphology and a lower dependence of the voltage on the transport-layer thickness, possibly due to improved electron mobility.

To this end, the invention provides a compound of the following formula I:

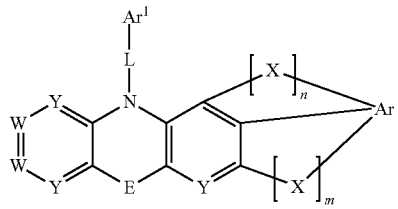

formula I where the symbols and indices used have the following meanings:

W is, identically or differently on each occurrence, N or $CR^1$;
Y is, identically or differently on each occurrence, N or $CR^2$
E is either a single covalent bond or a divalent unit selected from the group consisting of $N(R^3)$, $C(R^3)_2$, $Si(R^3)_2$, $C=O$, $C=NR^3$, $C=C(R^3)_2$, S, $S=O$, $SO_2$, $P(R^3)$ and $P(=O)R^3$;
X is, identically or differently on each occurrence, a divalent unit selected from the group consisting of $C(R^3)_2$, $N(R^3)$, $Si(R^3)_2$, $C=O$, $C=NR^3$, $C=C(R^3)_2$, S, O, $S=O$, $SO_2$, $P(R^3)$ and $P(=O)R^3$, with the proviso that, if E is a single covalent bond, X is a divalent unit selected from the group consisting of $C(R^3)_2$, $Si(R^3)_2$, $C=O$, $C=NR^3$, $C=C(R^3)_2$, S, O, $S=O$, $SO_2$, $P(R^3)$ and $P(=O)R^3$;
n, m are, independently of one another, 0 or 1, with the proviso that the sum of n and m is equal to 1 or 2;
Ar is a divalent or trivalent, mono- or polycyclic aromatic or heteroaromatic unit having 5 to 40 aromatic ring atoms, which may be substituted by one or more radicals $R^{4a}$;
$Ar^1$ is a mono- or polycyclic heteroaromatic group having 5 to 40 aromatic ring atoms, which may be substituted by one or more radicals $R^{4b}$;
L is either a single covalent bond or represents a divalent unit selected from the group consisting of —C(O)—, —$Ar^2$—C(O)— and —$Ar^2$—, where, in the case where the divalent unit is —$Ar^2$—C(O)—, the group $Ar^2$ is bonded to N and C(O) is bonded to the group $Ar^1$;
$Ar^2$ is a divalent mono- or polycyclic aromatic or heteroaromatic unit having 5 to 40 aromatic ring atoms, which may be substituted by one or more radicals $R^{4a}$ or $R^{4b}$;
$R^1$, $R^2$ are selected, identically or differently on each occurrence, from the group consisting of the following: H, D, F, Cl, Br, I, $N(Ar^3)_2$, $C(=O)Ar^3$, $P(=O)(Ar^3)_2$, $S(=O)Ar^3$, $S(=O)_2Ar^3$, CN, a straight-chain alkyl, alkoxy or thioalkoxy group having 1 to 40 C atoms or a branched or cyclic alkyl, alkoxy or thioalkoxy group having 3 to 40 C atoms or an alkenyl or alkynyl group having 2 to 40 C atoms, each of which may be substituted by one or more radicals $R^5$ and where in each case one or more non-adjacent $CH_2$ groups may be replaced by $R^5C=CR^5$, $C≡C$, $C=O$, $C=S$, $P(=O)(R^5)$, SO, $SO_2$, $NR^5$, O, S or $CONR^5$ and where one or more H atoms may be replaced by D, F, Cl, Br, I, CN or $NO_2$, or a mono- or polycyclic aromatic or heteroaromatic ring system having 5 to 40 aromatic ring atoms, which may in each case be substituted by one or more radicals $R^6$ or an aryloxy or heteroaryloxy group having 5 to 40 aromatic ring atoms, which may be substituted by one or more radicals $R^5$, or a combination of these systems; where, in addition, two or more adjacent substituents $R^1$ and/or $R^2$ may be linked to one another via a single covalent bond or a divalent group Z;
$R^3$ is selected, identically or differently on each occurrence, from the group consisting of the following: H, D, F, Cl, Br, I, $N(Ar^3)_2$, $C(=O)Ar^3$, $P(=O)(Ar^3)_2$, $S(=O)Ar^3$, $S(=O)_2Ar^3$, $CR^5=CR^5Ar^3$, CN, $NO_2$, $Si(R^5)_3$, $B(OR^5)_2$, $OSO_2R^5$, a straight-chain alkyl, alkoxy or thioalkoxy group having 1 to 40 C atoms or a branched or cyclic alkyl, alkoxy or thioalkoxy group having 3 to 40 C atoms or an alkenyl or alkynyl group having 2 to 40 C atoms, each of which may be substituted by one or more radicals $R^5$ and where in each case one or more non-adjacent $CH_2$ groups may be replaced by $R^5C=CR^5$, $C≡C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$ and where one or more H atoms may be replaced by D, F, Cl, Br, I, CN or $NO_2$, or a mono- or polycyclic aromatic or heteroaromatic ring system having 5 to 40 aromatic ring atoms, which may in each case be substituted by one or more radicals $R^6$, or an aryloxy or heteroaryloxy group having 5 to 40 aromatic ring atoms, which may be substituted by one or more radicals $R^5$, or a combination of these systems; where, in addition, two or more adjacent substituents $R^3$ may be linked to one another via a single covalent bond or a divalent group Z;
$R^{4a}$, $R^{4b}$ are each selected, identically or differently on each occurrence, from the group consisting of the following: D, F, Cl, Br, I, $N(Ar^3)_2$, $C(=O)Ar^3$, $P(=O)(Ar^3)_2$, $S(=O)Ar^3$, $S(=O)_2Ar^3$, CN, a straight-chain alkyl, alkoxy or thioalkoxy group having 1 to 40 C atoms or a branched or cyclic alkyl, alkoxy or thioalkoxy group having 3 to 40 C atoms or an alkenyl or alkynyl group having 2 to C atoms, each of which may be substituted by one or more radicals $R^5$ and where in each case one or more non-adjacent $CH_2$ groups may be replaced by $R^5C=CR^5$, $C≡C$, $C=O$, $C=S$, $P(=O)(R^5)$, SO, $SO_2$, $NR^5$, O, S or $CONR^5$ and where one or more H atoms may be replaced by D, F, Cl, Br, I, CN or $NO_2$, or a mono- or polycyclic aromatic or heteroaromatic ring system having 5 to 40 aromatic ring atoms, which may in each case be substituted by one or more radicals $R^6$, or an aryloxy or heteroaryloxy group having 5 to 40 aromatic ring atoms, which may be substituted by one or more radicals $R^5$, or a combination of these systems; where, in addition, two or more adjacent substituents $R^{4a}$ or $R^{4b}$ may be linked to one another via a single covalent bond or a divalent group Z;

Ar³ is a mono- or polycyclic aromatic or heteroaromatic ring system having 5 to 40 aromatic ring atoms, which may in each case be substituted by one or more radicals $R^6$;

$R^5$ is, identically or differently on each occurrence, H, D, a straight-chain alkyl group having 1 to 20 C atoms or a branched or cyclic alkyl group having 3 to 20 C atoms, where one or more non-adjacent $CH_2$ groups may be replaced by NH, O or S and where one or more H atoms may be replaced by F, or a mono- or polycyclic aromatic or heteroaromatic ring system having 5 to 20 aromatic ring atoms, which may in each case be substituted by one or more radicals $R^6$; where, in addition, two or more substituents $R^5$ may be linked to one another via a single covalent bond or a divalent group Z;

$R^6$ is, identically or differently on each occurrence, H, D, F, CN, a straight-chain alkyl group having 1 to 20 C atoms or a branched or cyclic alkyl group having 3 to 20 C atoms, where one or more non-adjacent $CH_2$ groups may be replaced by NH, O or S and where one or more H atoms may be replaced by F; where, in addition, two or more substituents $R^6$ may be linked to one another via a single covalent bond or a divalent group Z;

Z represents a divalent group —$(CH_2)_q$—, where q is equal to 1, 2, 3, 4 or 5, preferably 1, 2, 3 or 4, more preferably 1, 2 or 3 and most preferably 1 or 2.

In a preferred embodiment of the invention, in total a maximum of two symbols Y and W, particularly preferably in total a maximum of one symbol Y and W, simultaneously stand for N.

A divalent or trivalent mono- or polycyclic aromatic or heteroaromatic unit, as defined for Ar or $Ar^2$, preferably contains 5 to 40, more preferably 5 to 20, most preferably 5 to 10 aromatic ring atoms. If the unit is an aromatic unit, it preferably contains 6 to 40, more preferably 6 to 20, most preferably 6 to 10 carbon atoms as ring atoms. If the unit is a heteroaromatic unit, it preferably contains 5 to 40, more preferably 5 to 20, most preferably 5 to aromatic ring atoms, of which at least one is a heteroatom. The heteroatoms are preferably selected from N, O and/or S. An aromatic or heteroaromatic unit is taken to mean either a simple aromatic ring, i.e. benzene, a simple heteroaromatic ring, for example pyridine, pyrimidine, thiophene, etc., or a condensed aryl or heteroaryl group, for example naphthalene, anthracene, phenanthrene, quinoline, isoquinoline, benzothiophene, benzofuran or indole etc.

Examples according to the invention of the aromatic or heteroaromatic unit are accordingly: benzene, naphthalene, anthracene, phenanthrene, pyrene, chrysene, benzanthracene, perylene, naphthacene, pentacene, benzopyrene, furan, benzofuran, isobenzofuran, dibenzofuran, thiophene, benzothiophene, isobenzothiophene, dibenzothiophene, pyrrole, indole, isoindole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

As a divalent or trivalent unit, the above-mentioned compounds are in such a form that two or three hydrogen substituents are not present and these compounds are bonded at these sites—as indicated in formula I.

In the present invention, a mono- or polycyclic aromatic or heteroaromatic group is taken to mean a monovalent radical which is otherwise defined exactly like the mono- or polycyclic aromatic or heteroaromatic unit. The examples mentioned above are also illustrative here.

For the purposes of the present invention, a straight-chain, branched or cyclic alkyl group is taken to mean an alkyl, alkenyl or alkynyl group, preferably having 1 to 40 C atoms, more preferably 1 to 20 C atoms, or 3 to 40 C atoms, more preferably 3 to 20 C atoms respectively. Cyclic alkyl groups can be mono-, bi- or polycyclic alkyl groups. Individual —CH— or —$CH_2$— groups may be replaced by N, NH, O or S. The radicals are preferably taken to mean methyl, ethyl, n-propyl, i-propyl, n-butyl, i-butyl, s-butyl, t-butyl, 2-methylbutyl, n-pentyl, s-pentyl, t-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl. A $C_1$- to $C_{40}$-alkoxy group is preferably taken to mean methoxy, trifluoromethoxy, ethoxy, n-propoxy, i-propoxy, n-butoxy, i-butoxy, s-butoxy, t-butoxy or 2-methylbutoxy.

An alkoxy group or thioalkyl group is taken to mean an alkyl group as defined above which is bonded via an O or S atom.

The alkyl groups, alkoxy groups or thioalkyl groups may additionally be substituted by one or more radicals $R^5$ as defined above.

For the purposes of this invention, a mono- or polycyclic aromatic ring system is preferably taken to mean an aromatic ring system having 6 to 40, preferably 6 to 30, particularly preferably 6 to 12 carbon atoms. For the purposes of the present invention, an aromatic ring system is intended to be taken to mean a system which does not necessarily contain only aromatic groups, but instead in which, in addition, a plurality of aromatic groups may be interrupted by a short non-aromatic unit (<10% of the atoms other than H, preferably <5% of the atoms other than H), such as, for example, $sp^3$-hybridised C, O, N, etc., or a CO group. These aromatic ring systems may be monocyclic or polycyclic, i.e. they may have one ring (for example phenyl) or two or more rings, which may also be condensed (for example naphthyl) or covalently linked (for example biphenyl), or contain a combination of condensed and linked rings. However, condensed rings are particularly preferred.

Preferred aromatic ring systems are, for example, benzene, biphenyl, terphenyl, naphthalene, anthracene, binaphthyl, phenanthrene, benzanthracene, dihydrophenanthrene, pyrene, dihydropyrene, chrysene, perylene, tetracene, pentacene, benzopyrene, fluorene, spirobifluorene and indene.

For the purposes of this invention, a mono- or polycyclic heteroaromatic ring system is preferably taken to mean a heteroaromatic ring system having 5 to 40, preferably 5 to 30, particularly preferably 5 to 14 ring atoms. The heteroaromatic ring system contains at least one heteroatom selected from N, O and S (the remaining atoms are carbon). In addition, a heteroaromatic ring system is intended to be taken to mean a system which does not necessarily contain only aromatic or heteroaromatic groups, but instead in which, in addition, a plurality of aromatic or heteroaromatic groups may be interrupted by a short non-aromatic unit (<10% of the atoms other than H, preferably <5% of the atoms other than H), such as, for example, sp$^3$-hybridised C, O, N, etc., or a CO group. These heteroaromatic ring systems may be monocyclic or polycyclic, i.e. they may have one ring (for example pyridyl) or two or more rings, which may also be condensed or covalently linked, or contain a combination of condensed and linked rings. Condensed rings are particularly preferred.

Preferred heteroaromatic ring systems are, for example, 5-membered rings, such as pyrrole, pyrazole, imidazole, 1,2,3-triazole, 1,2,4-triazole, tetrazole, furan, thiophene, selenophene, oxazole, isoxazole, 1,2-thiazole, 1,3-thiazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 6-membered rings, such as pyridine, pyridazine, pyrimidine, pyrazine, 1,3,5-triazine, 1,2,4-triazine, 1,2,3-triazine, 1,2,4,5-tetrazine, 1,2,3,4-tetrazine, 1,2,3,5-tetrazine, or condensed groups, such as indole, isoindole, indolizine, indazole, benzimidazole, benzotriazole, purine, naphthimidazole, phenanthrimidazole, pyridimidazole, pyrazinoimidazole, quinoxalinoimidazole, benzoxazole, naphthoxazole, anthroxazole, phenanthroxazole, isoxazole, benzothiazole, benzofuran, isobenzofuran, dibenzofuran, quinoline, isoquinoline, pteridine, benzo-5,6-quinoline, benzo-6,7-quinoline, benzo-7,8-quinoline, benzoisoquinoline, acridine, phenothiazine, phenoxazine, benzopyridazine, benzopyrimidine, quinoxaline, phenazine, naphthyridine, azacarbazole, benzocarboline, phenanthridine, phenanthroline, thieno[2,3b]thiophene, thieno[3,2b]thiophene, dithienothiophene, isobenzothiophene, dibenzothiophene, benzothiadiazothiophene, or combinations of these groups. Particular preference is given to imidazole, benzimidazole and pyridine.

If two substituents, for example two R$^1$ or R$^1$ and R$^2$, form a divalent mono- or polycyclic aromatic or heteroaromatic ring system with one another, the above-mentioned short non-aromatic unit may also be bonded directly to Y or W. In this case, the short non-aromatic unit is particularly preferably a CO group.

An aryloxy or heteroaryloxy group having 5 to 40 aromatic ring atoms is taken to mean a group which carries a mono- or polycyclic aromatic or heteroaromatic group having 5 to 40 ring atoms, as defined above, via an O atom. The aryloxy or heteroaryloxy group may likewise carry one or more substituents which are defined above.

In an embodiment of the present invention, Y is preferably, identically or differently, CR$^1$.

It is likewise an embodiment of the present invention that W is preferably, identically or differently, CR$^2$.

In still a further embodiment of the present invention, E is preferably either a single covalent bond or a divalent unit selected from N(R$^3$), C(R$^3$)$_2$, O and S. E is even more preferably equal to a single covalent bond.

In still a further embodiment of the present invention, X is preferably, identically or differently on each occurrence, a divalent unit selected from the group consisting of C(R$^3$)$_2$, S and O. X is particularly preferably equal to C(R$^3$)$_2$.

In still a further embodiment, Ar is preferably a divalent or trivalent mono- or polycyclic aromatic or heteroaromatic unit having 5 to 10 aromatic ring atoms, which may be substituted by one or more radicals R$^{4a}$. Ar is particularly preferably equal to phenylene or naphthylene, most preferably phenylene.

In still a further embodiment of the present invention, Ar$^1$ is preferably a mono- or polycyclic heteroaromatic group having 5 to 10 aromatic ring atoms, which may be substituted by one or more radicals R$^{4b}$. Ar$^1$ is particularly preferably an electron-deficient heteroaromatic group, which may be substituted by one or more radicals R$^{4b}$. Accordingly, even greater preference is given to heteroaromatic groups having 6 aromatic ring atoms, at least one of which is an N atom, or heteroaromatic groups having 5 aromatic ring atoms, at least 2 of which are heteroatoms, preferably at least one of which is an N atom, which may be substituted by R$^{4b}$, where in each case further aryl or heteroaryl groups may also be condensed onto these groups. Preferred examples of electron-deficient heteroaromatic groups are: pyridine, pyrazine, pyrimidine, pyridazine, 1,2,4-triazine, 1,3,5-triazine, quinoline, isoquinoline, quinoxaline, pyrazole, imidazole, benzimidazole, thiazole, benzothiazole, oxazole and benzoxazole, each of which may be substituted by R$^{4b}$. Ar$^1$ is most preferably a 1,3,5-triazine which is substituted by R$^{4b}$ or unsubstituted.

In still a further embodiment of the present invention, L is preferably a single covalent bond or a divalent unit —Ar$^2$—. Ar$^2$ here is preferably a divalent mono- or polycyclic aromatic or heteroaromatic unit having 5 to 10 aromatic ring atoms, which may be substituted by one or more radicals R$^{4a}$ or R$^{4b}$. Particularly preferred examples thereof are phenylene and naphthylene, more preferably phenylene.

In a further embodiment, R$^1$ and R$^2$ are each preferably selected, independently of one another, from the group consisting of H, D, N(Ar$^3$)$_2$, C(=O)Ar$^3$, a straight-chain alkyl group having 1 to 20 C atoms or a branched or cyclic alkyl group having 3 to 20 C atoms and a mono- or polycyclic aromatic or heteroaromatic ring system having 5 to 20 aromatic ring atoms, each of which may be substituted by one or more radicals R$^6$. R$^2$ is particularly preferably equal to H, and one of the two R$^1$ is H and the other is selected from H, N(Ar$^3$)$_2$, C(=O)Ar$^3$ and a mono- or polycyclic aromatic ring system having 5 to 20 aromatic ring atoms, which may in each case be substituted by one or more radicals R$^6$. Alternatively, two R$^1$ or R$^1$ and R$^2$ together may also form a mono- or polycyclic aromatic or heteroaromatic ring system having 5 to 20 aromatic ring atoms. Preferred examples thereof are the following:

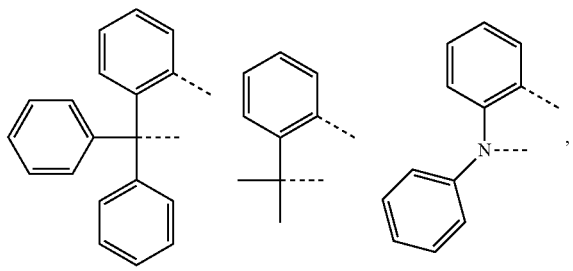

where the divalent systems are bonded via the dashed lines.

In a further embodiment of the present invention, R$^3$ is preferably selected, identically or differently on each occurrence, from the group consisting of H, D, a straight-chain alkyl group having 1 to 10 C atoms, a branched or cyclic alkyl group having 3 to 10 C atoms and a mono- or polycyclic aromatic or heteroaromatic ring system having 5 to 10 aromatic ring atoms. Preference is given here to methyl, phenyl, diphenylamino-p-phenyl and 3-(N-phenyl)carbazolyl. Alternatively, two R$^3$ may also form a divalent mono- or polycyclic aromatic or heteroaromatic ring system having 5 to 20 aromatic ring atoms with one another. A preferred example thereof is:

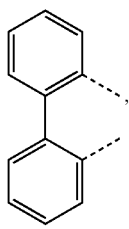

where the dashed lines represent the bonds to X.

In a further embodiment of the present invention, $R^{4a}$ is preferably selected, identically or differently on each occurrence, from the group consisting of the following: $N(Ar^3)_2$, $C(=O)Ar^3$, a straight-chain alkyl group having 1 to 6 C atoms or a branched or cyclic alkyl group having 3 to 6 C atoms, where one or more H atoms may be replaced by F, or a mono- or polycyclic aromatic or heteroaromatic ring system having 5 to 20 aromatic ring atoms. Particularly preferred examples thereof are phenyl, diphenylamine and $C(=O)$-Ph.

In a further embodiment of the present invention, $R^{4b}$ is preferably selected, identically or differently on each occurrence, from the group consisting of the following: CN, F, a straight-chain alkyl group having 1 to 6 C atoms, a branched or cyclic alkyl group having 3 to 6 C atoms, where one or more H atoms may be replaced by F, or a mono- or polycyclic aromatic or heteroaromatic ring system having 5 to 20 aromatic ring atoms. Particularly preferred examples thereof are phenyl, naphthyl and carbazolyl.

In still a further embodiment of the present invention, $Ar^3$ is preferably a mono- or polycyclic aromatic or heteroaromatic ring system having 5 to 20 aromatic ring atoms.

In a further embodiment of the present invention, the sum of the indices n+m=1.

It is part of the present invention that the said embodiments or preferred ranges or definitions of the present invention can be combined with one another as desired.

The following therefore preferably applies to the symbols and indices:

Y is on each occurrence, identically or differently, $CR^1$;

W is on each occurrence, identically or differently, $CR^2$

E is either a single covalent bond or a divalent unit selected from $N(R^3)$, $C(R^3)_2$, O and S, in particular a single covalent bond;

X is, identically or differently on each occurrence, a divalent unit selected from the group consisting of $C(R^3)_2$, S and O, in particular $C(R^3)_2$;

Ar is a divalent or trivalent mono- or polycyclic aromatic or heteroaromatic unit having 5 to 10 aromatic ring atoms, which may be substituted by one or more radicals $R^{4a}$, in particular phenylene or naphthylene, most preferably phenylene;

$Ar^1$ is a mono- or polycyclic heteroaromatic group having 5 to 10 aromatic ring atoms, which may be substituted by one or more radicals $R^{4b}$, preferably an electron-deficient heteroaromatic group, which may be substituted by one or more radicals $R^{4b}$, in particular pyridine, pyrazine, pyrimidine, pyridazine, 1,2,4-triazine, 1,3,5-triazine, quinoline, isoquinoline, quinoxaline, pyrazole, imidazole, benzimidazole, thiazole, benzothiazole, oxazole or benzoxazole, each of which may be substituted by $R^{4b}$, most preferably a 1,3,5-triazine which is substituted by $R^{4b}$ or unsubstituted;

L is a single covalent bond or a divalent unit $—Ar^2—$;

$Ar^2$ is a divalent mono- or polycyclic aromatic or heteroaromatic unit having to 10 aromatic ring atoms, which may be substituted by one or more radicals $R^{4a}$ or $R^{4b}$, in particular phenylene and naphthylene;

$R^1$, $R^2$ are each selected, independently of one another, from the group consisting of H, D, $N(Ar^3)_2$, $C(=O)Ar^3$, a straight-chain alkyl group having 1 to 20 C atoms or a branched or cyclic alkyl group having 3 to 20 C atoms and a mono- or polycyclic aromatic or heteroaromatic ring system having 5 to 20 aromatic ring atoms, each of which may be substituted by one or more radicals $R^6$;

$R^3$ is selected, identically or differently on each occurrence, from the group consisting of H, D, a straight-chain alkyl group having 1 to 10 C atoms, a branched or cyclic alkyl group having 3 to 10 C atoms and a mono- or polycyclic aromatic or heteroaromatic ring system having 5 to aromatic ring atoms;

$R^{4a}$ is selected, identically or differently on each occurrence, from the group consisting of the following: $N(Ar^3)_2$, $C(=O)Ar^3$, a straight-chain alkyl group having 1 to 6 C atoms or a branched or cyclic alkyl group having 3 to 6 C atoms, where one or more H atoms may be replaced by F, or a mono- or polycyclic aromatic or heteroaromatic ring system having 5 to 20 aromatic ring atoms;

$R^{4b}$ is selected, identically or differently on each occurrence, from the group consisting of the following: CN, F, a straight-chain alkyl group having 1 to 6 C atoms, a branched or cyclic alkyl group having 3 to 6 C atoms, where one or more H atoms may be replaced by F, or a mono- or polycyclic aromatic or heteroaromatic ring system having 5 to 20 aromatic ring atoms;

$Ar^3$ is a mono- or polycyclic aromatic or heteroaromatic ring system having to 20 aromatic ring atoms;

for the sum of the indices n+m: n+m=1.

It is furthermore preferred for the compounds of the general formula I to satisfy the following structural formulae:

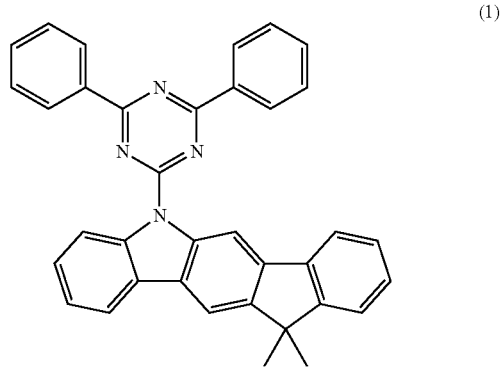

(1)

(2)
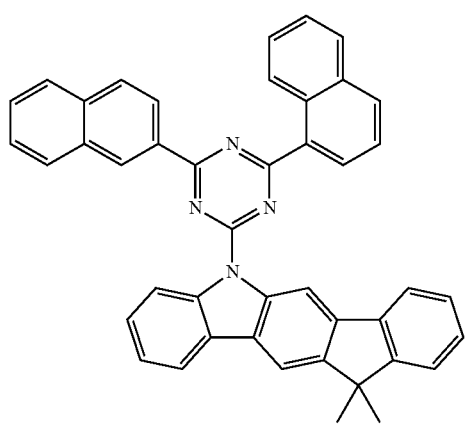
(3)
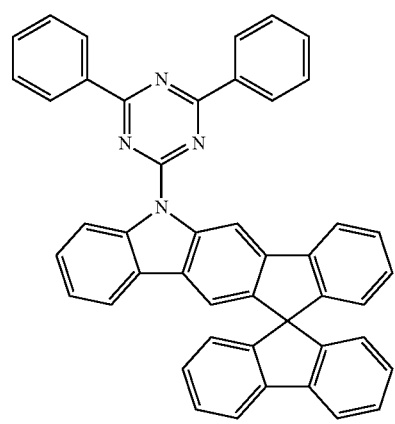
(4)
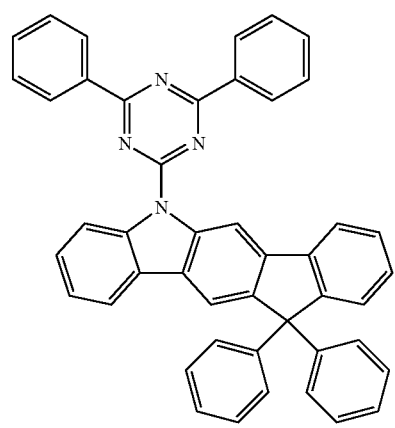
(5)
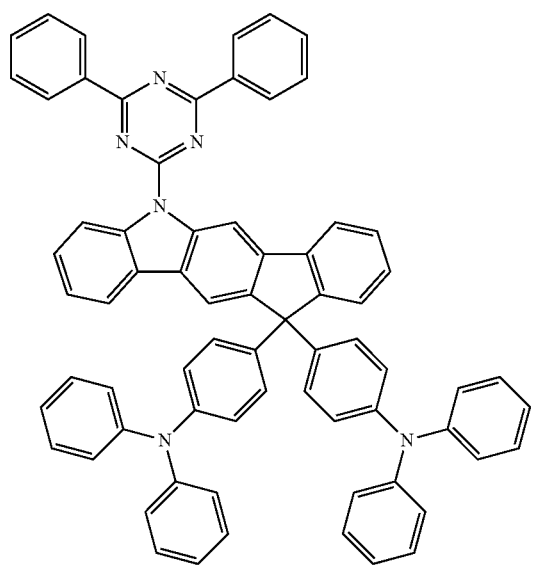
(6)
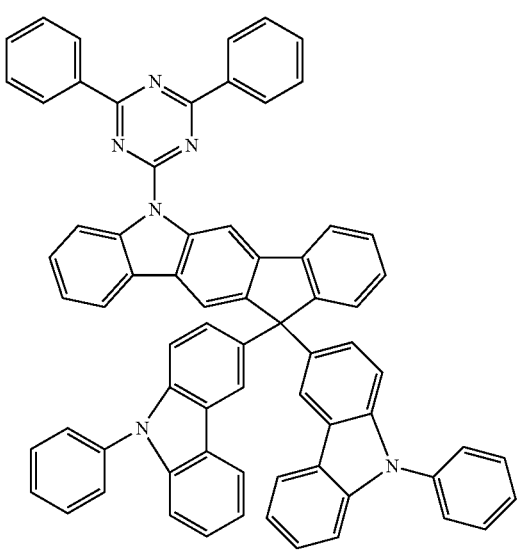
(7)
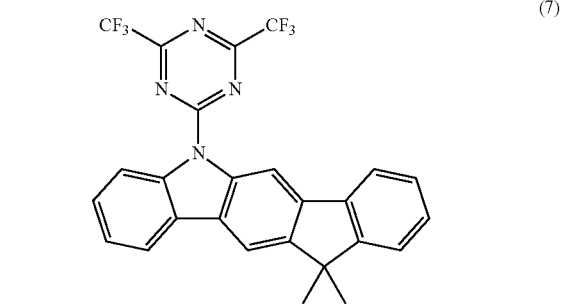

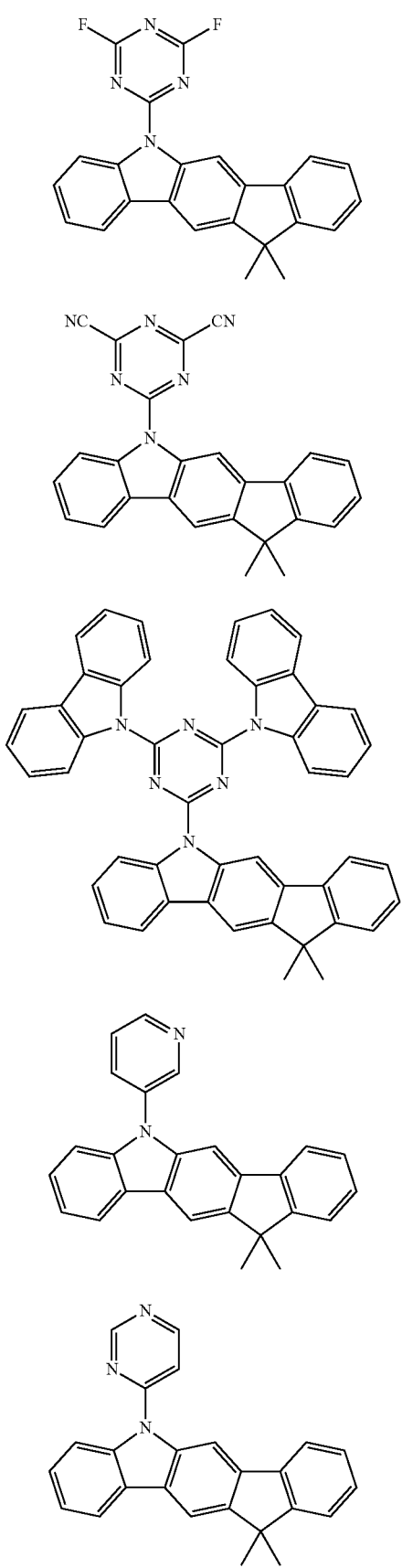
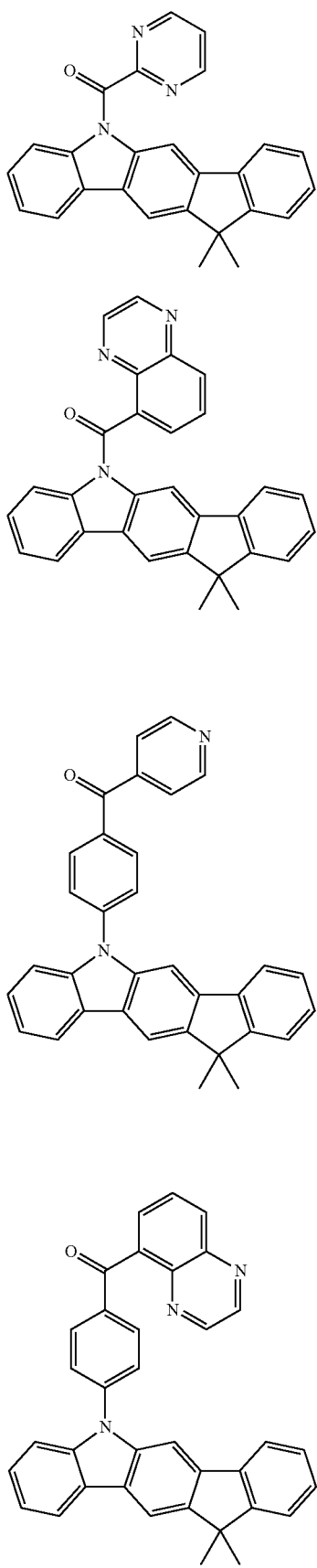

(17) 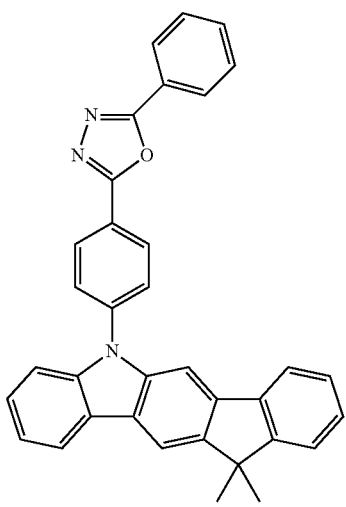
(18) 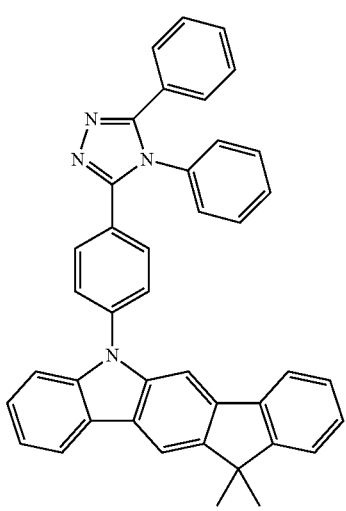
(19) 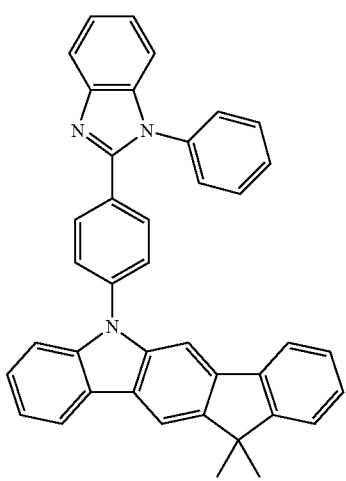
(20) 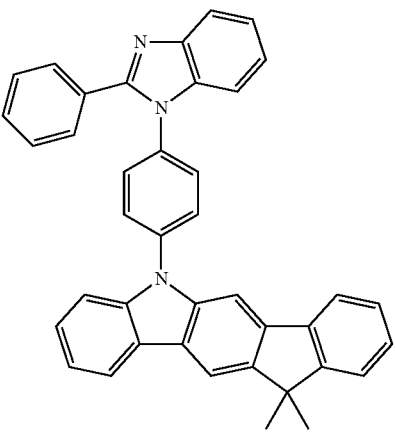
(21) 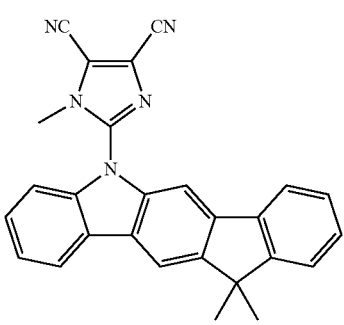
(22) 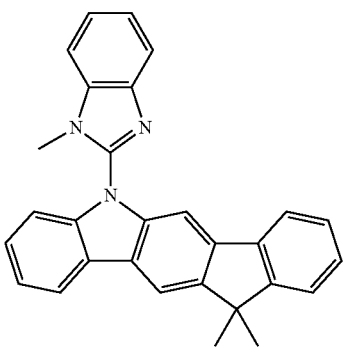
(23) 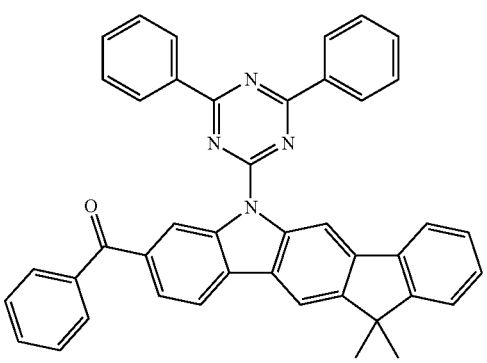

(24)
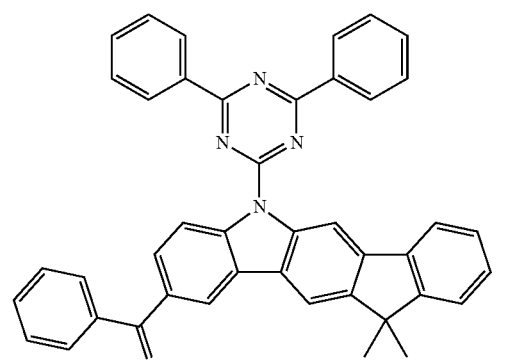
(25)
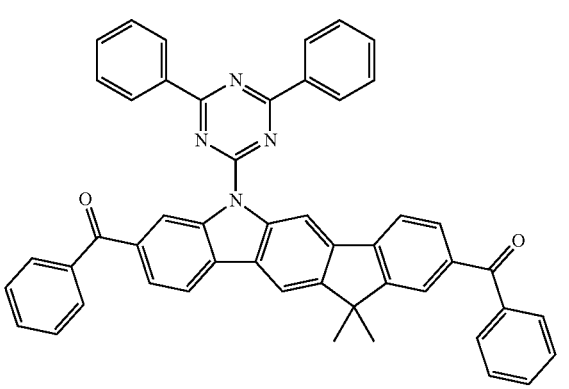
(26)
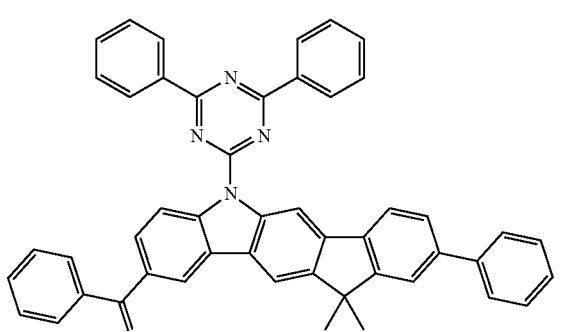
(27)
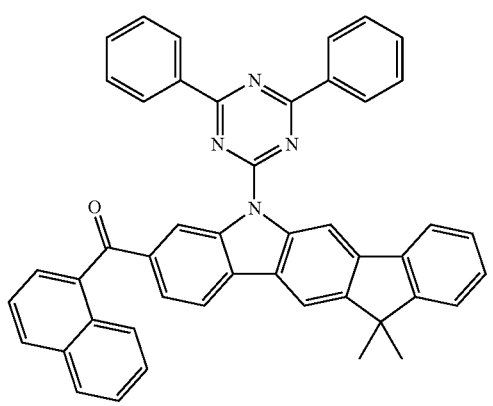
(28)
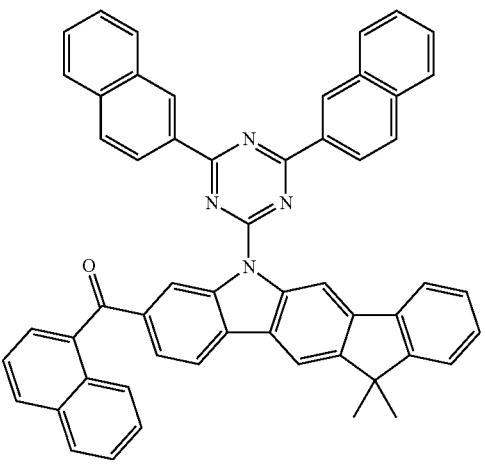
(29)
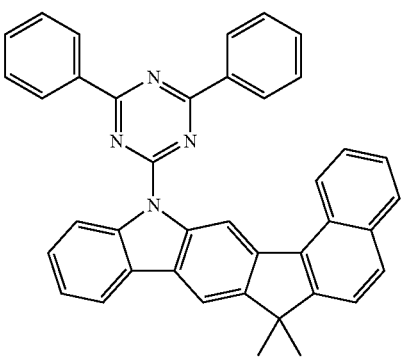
(30)
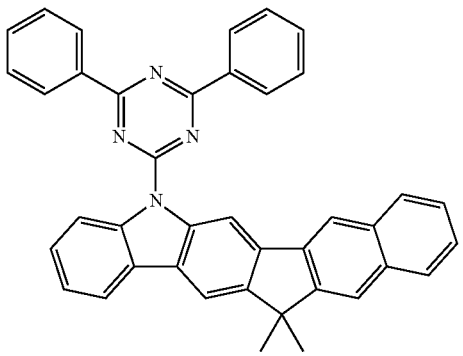
(31)
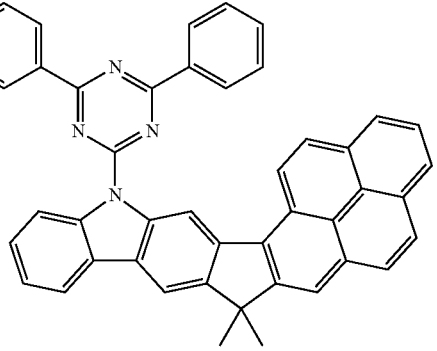

-continued
(32)
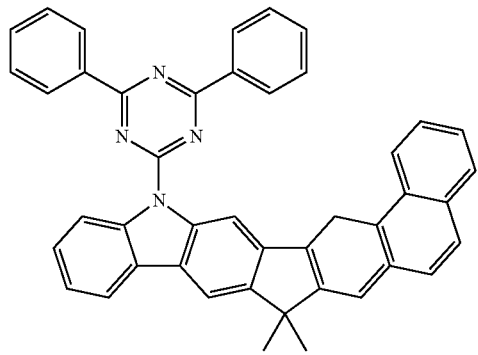
(33)
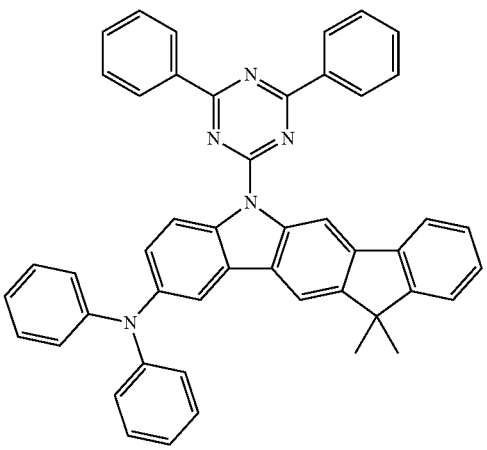
(34)
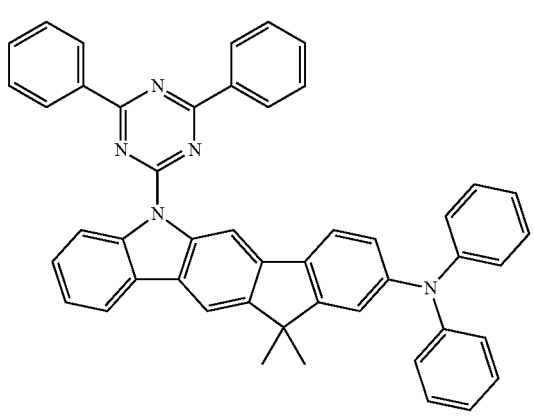
(35)
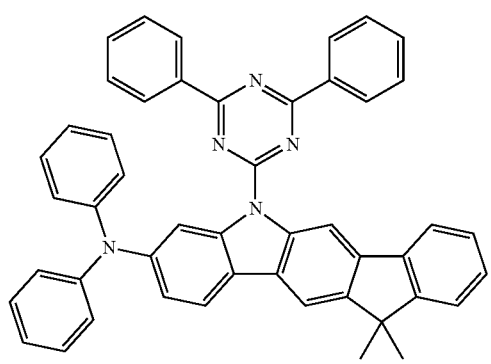
-continued
(36)
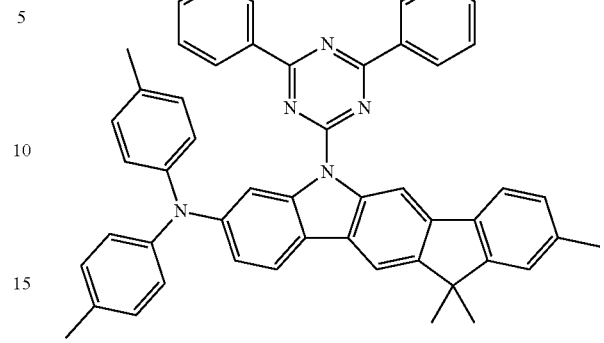
(37)
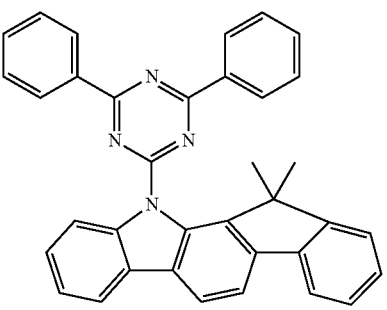
(38)
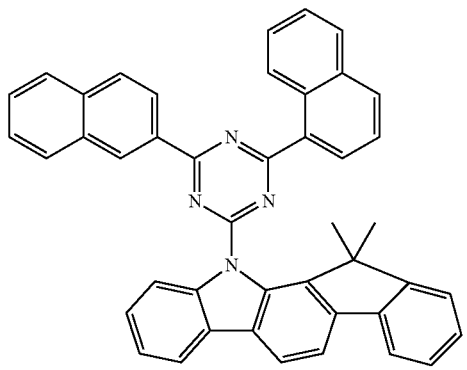
(39)
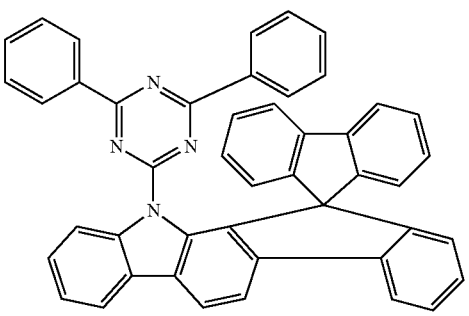

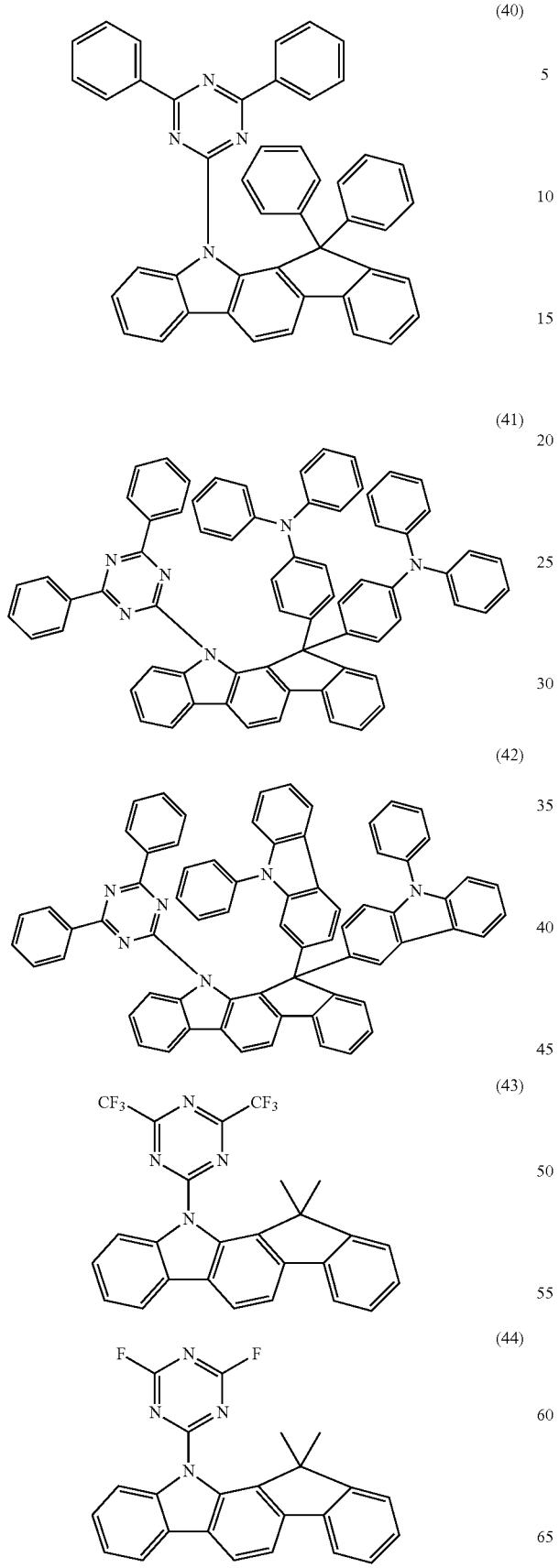
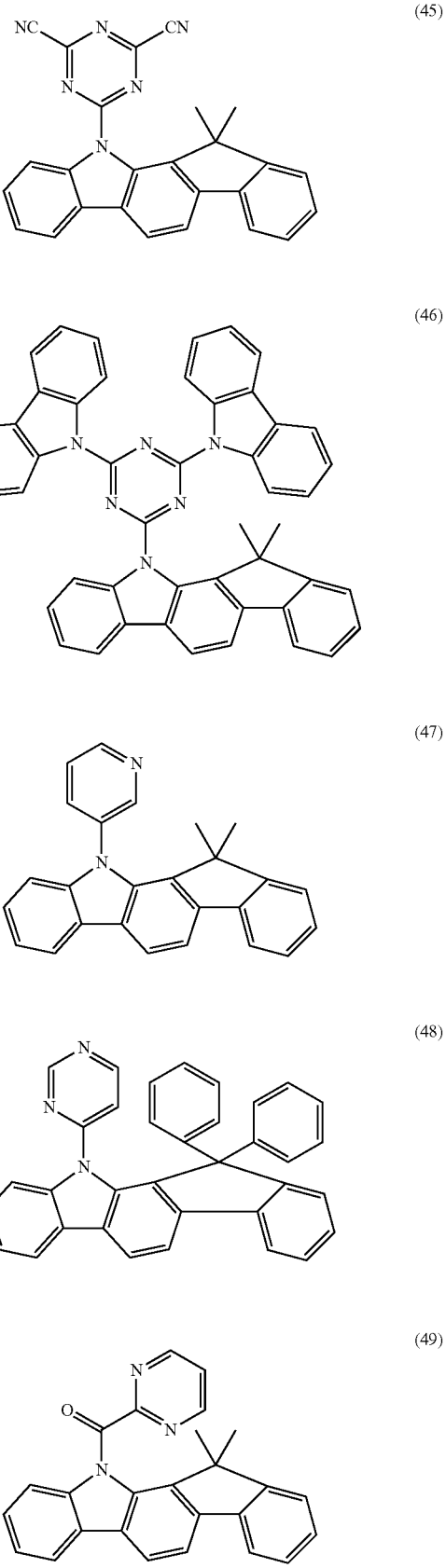

23
-continued
(50)
(51)
(52)
(53)
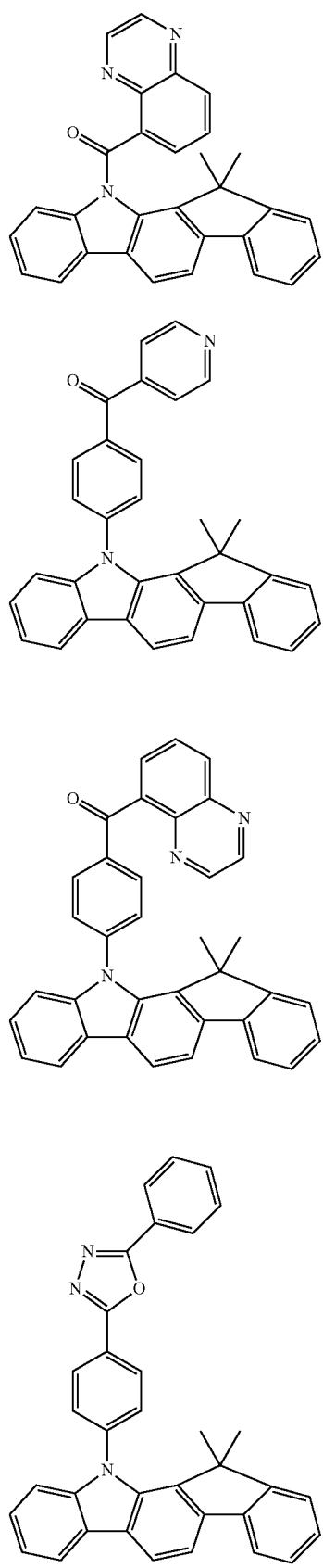
24
-continued
(54)
(55)
(56)
(57)
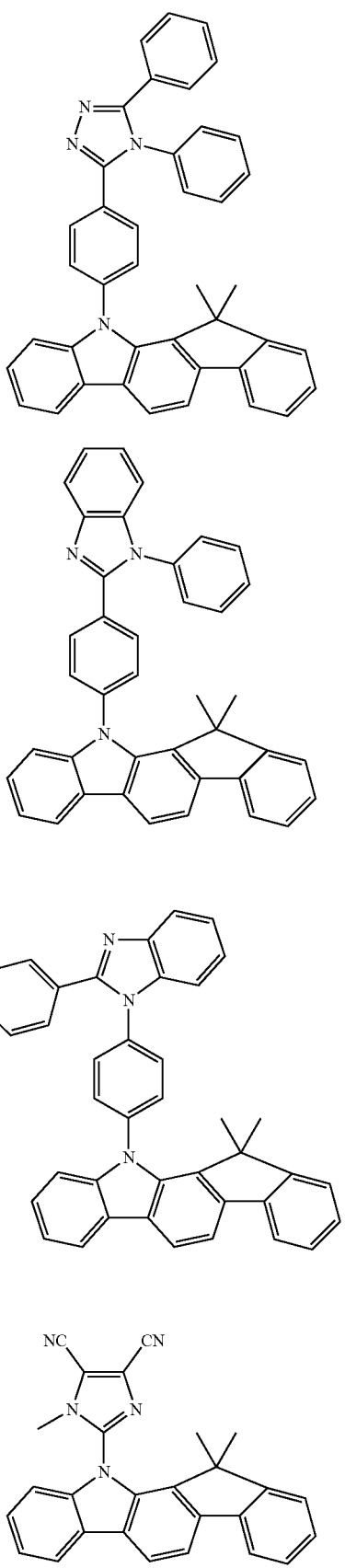

(58)
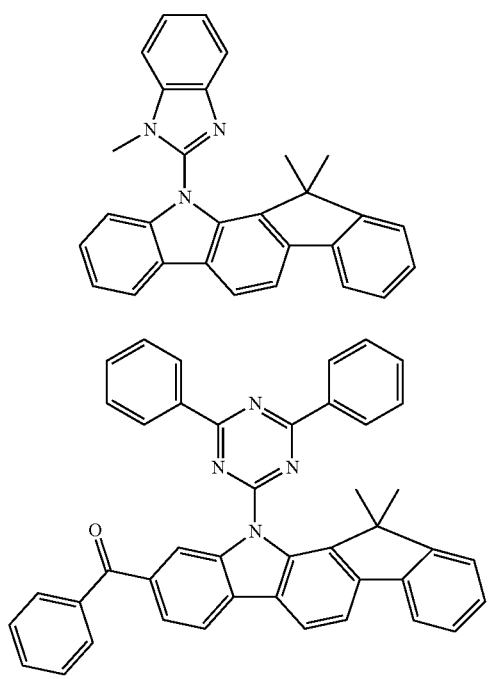
(59)
(60)
(61)
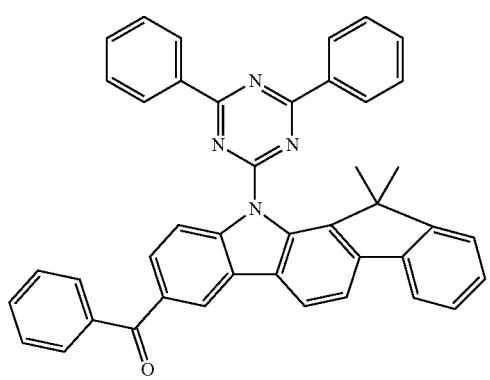
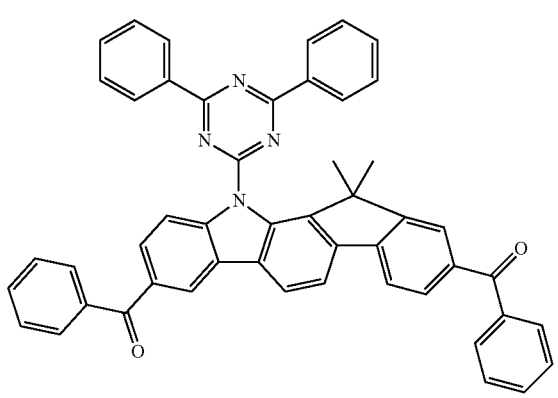
(62)
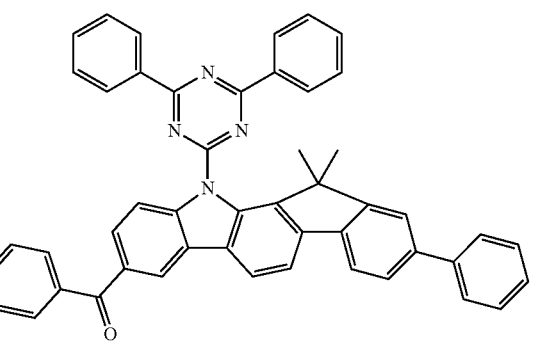
(63)
(64)
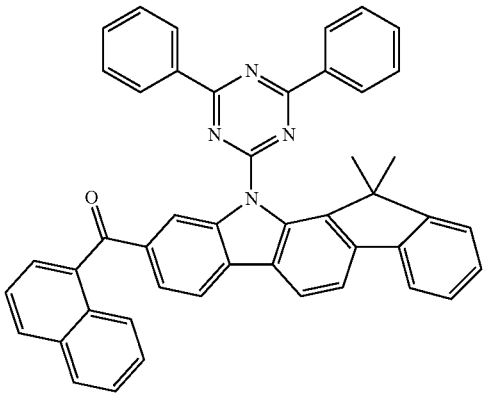
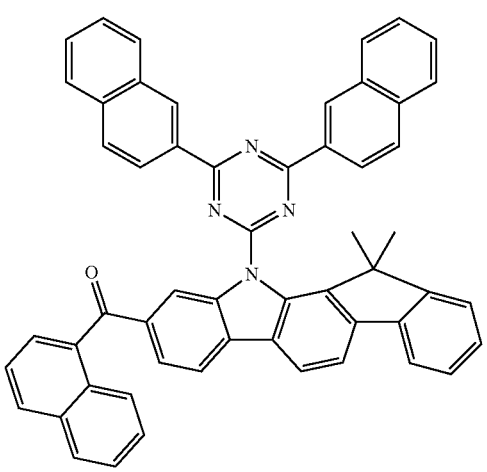
(65)
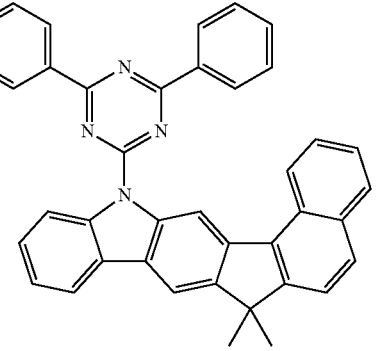

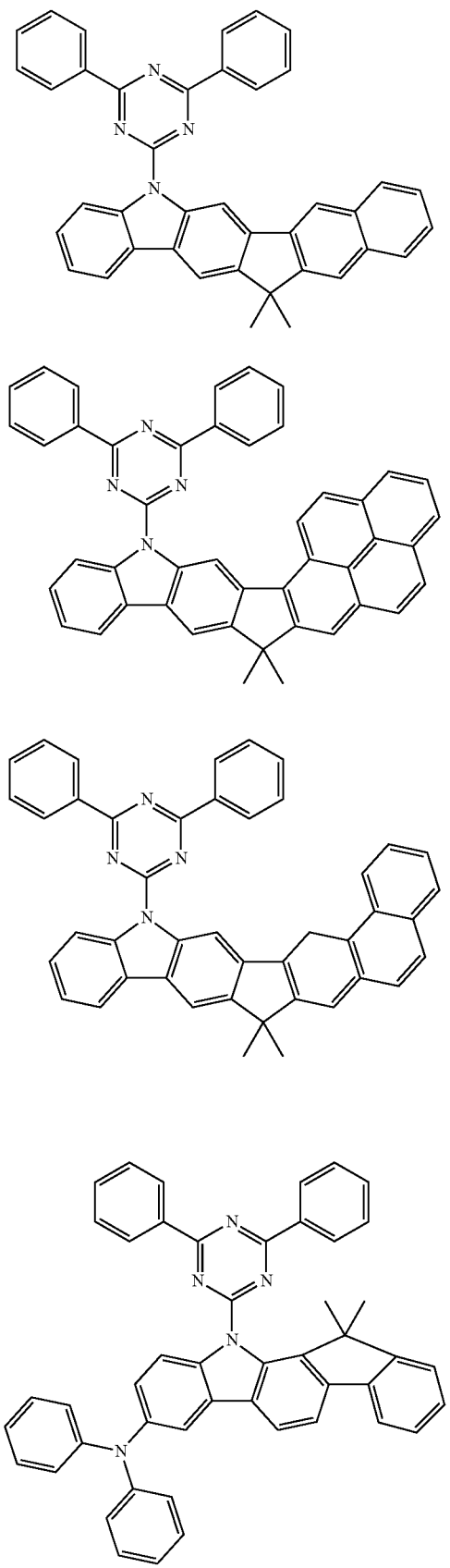
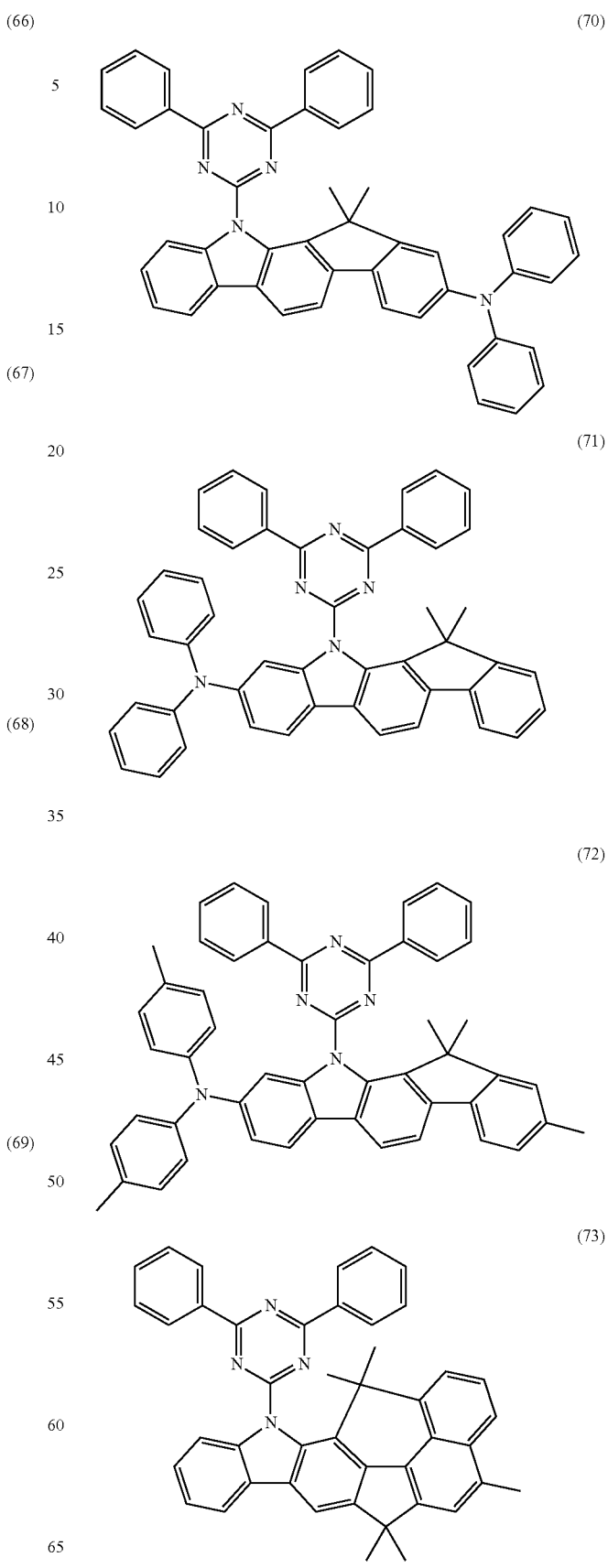

-continued
(74)
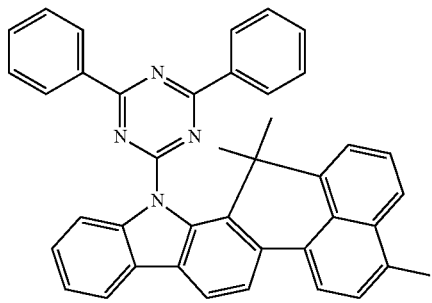
(75)
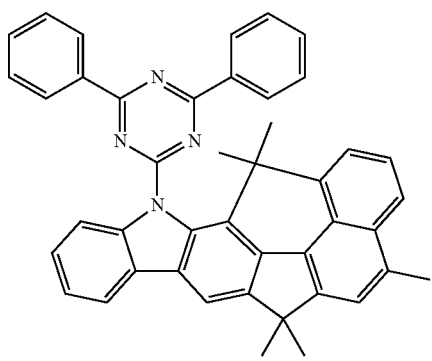
(76)
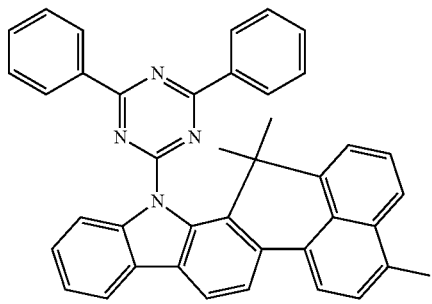
(77)
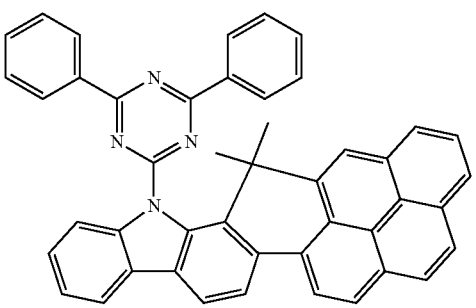
(78)
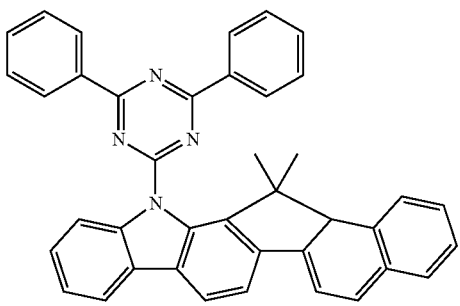
-continued
(79)
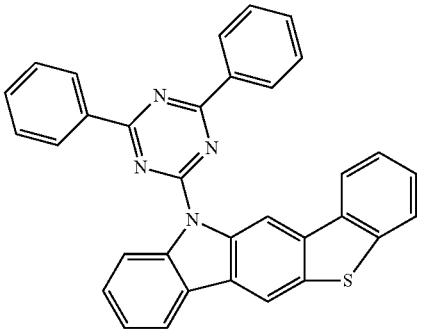
(80)
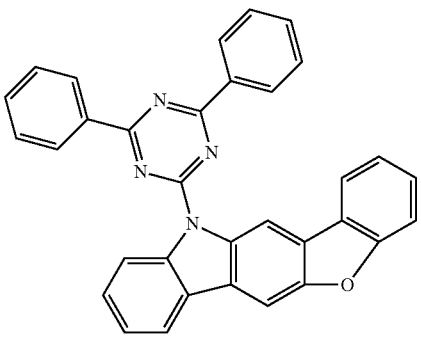
(81)
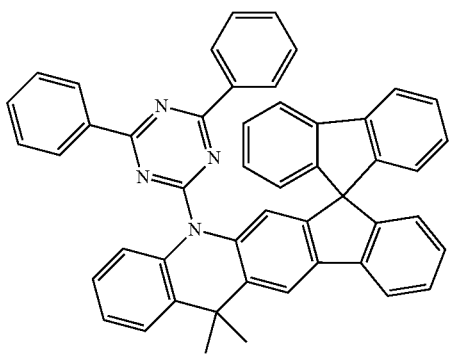
(82)
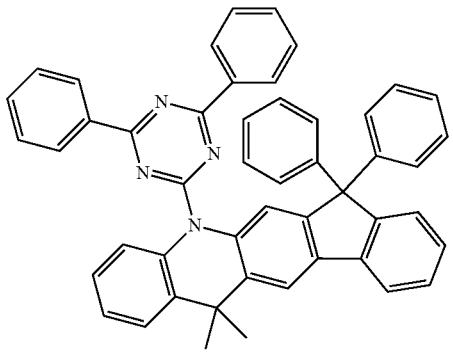

-continued
(83)
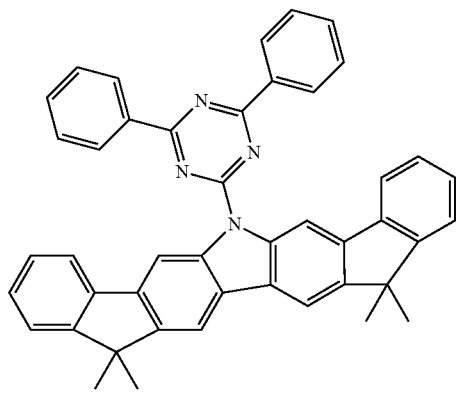
(86)
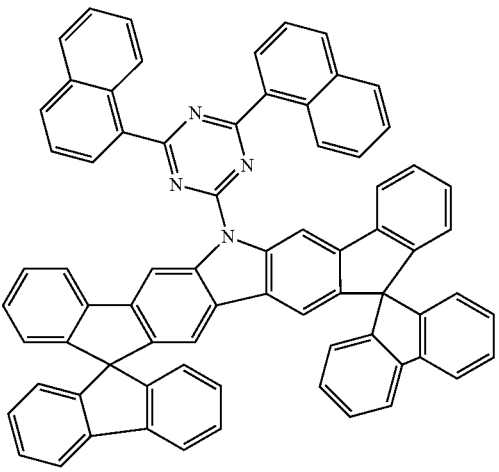
(84)
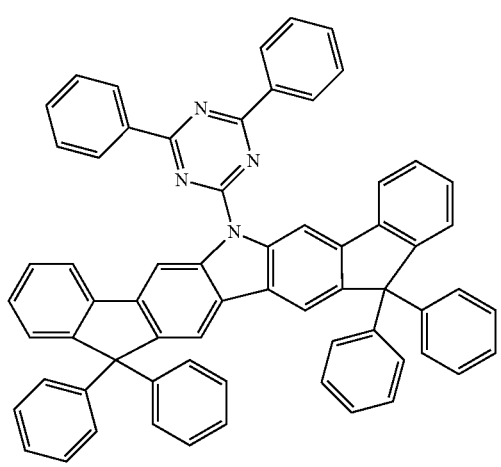
(87)
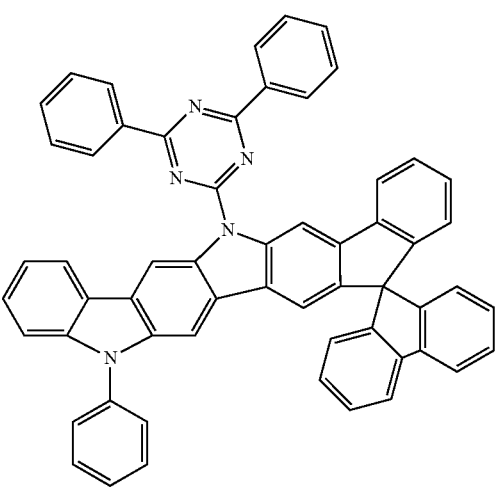
(85)
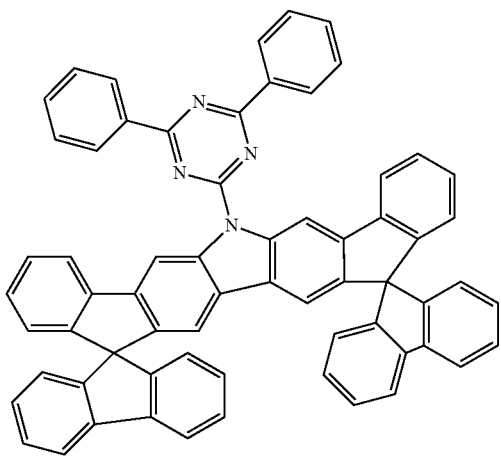
(88)
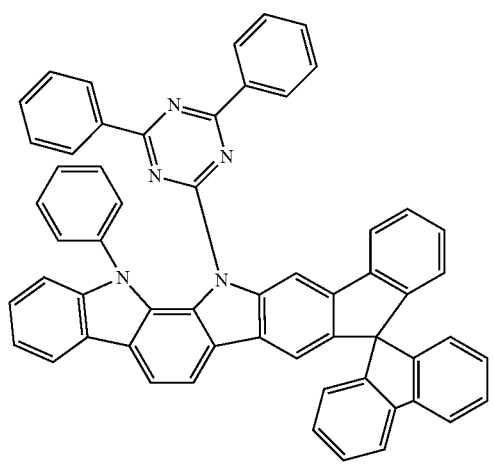

(89)
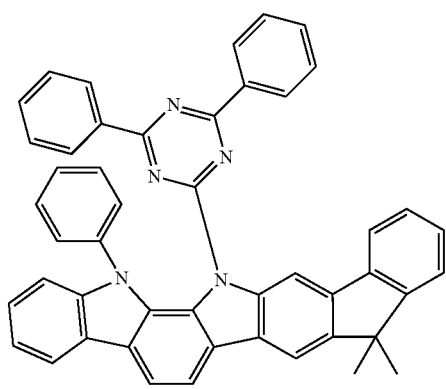
(90)
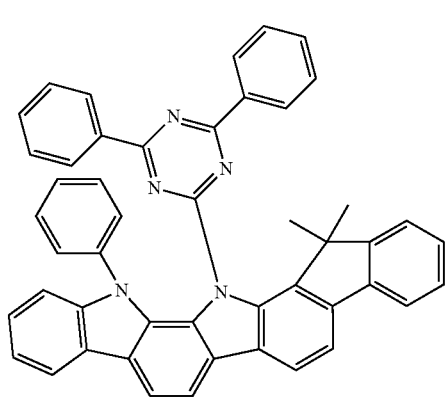
(91)
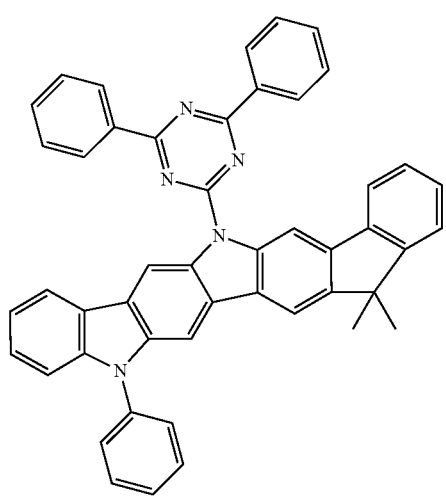
(92)
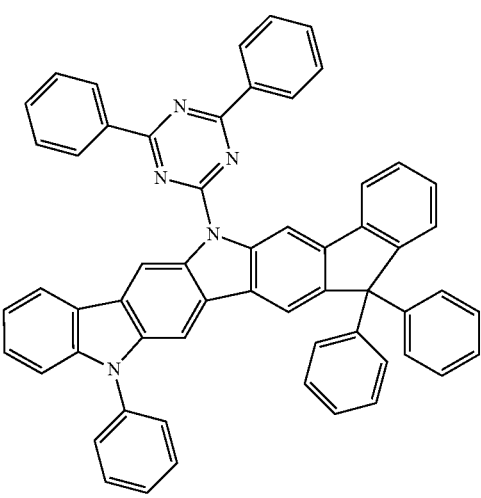
(93)
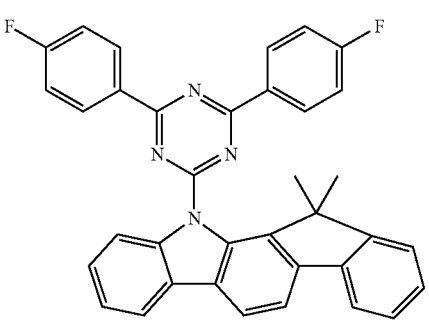
(94)
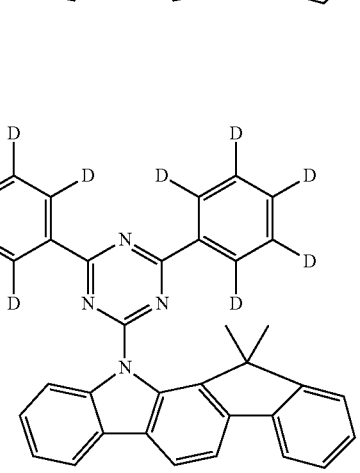
(95)
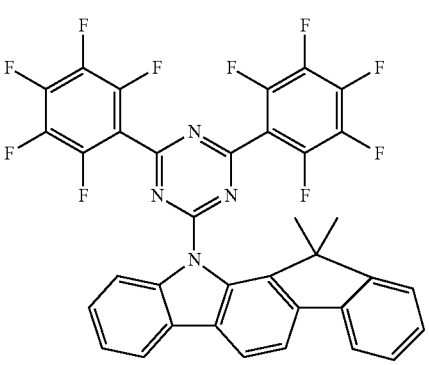

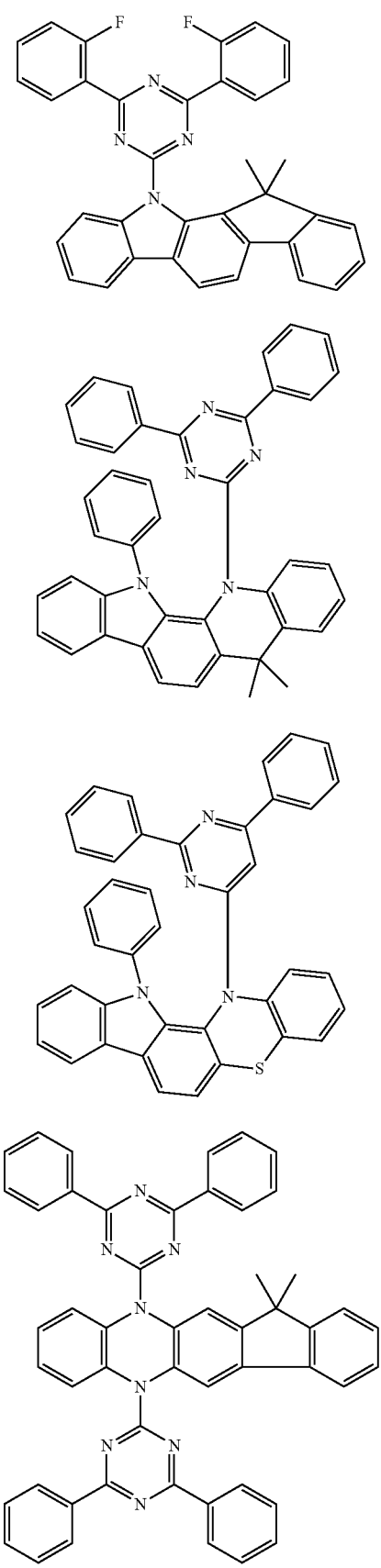
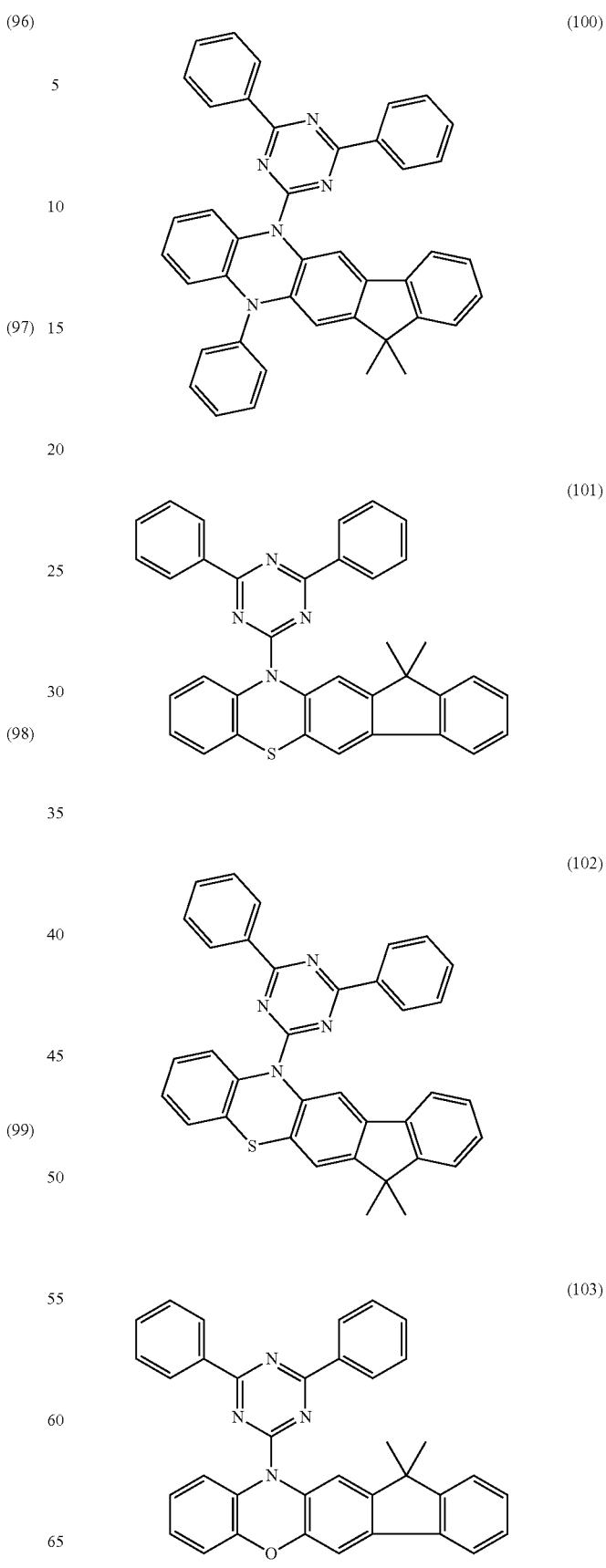

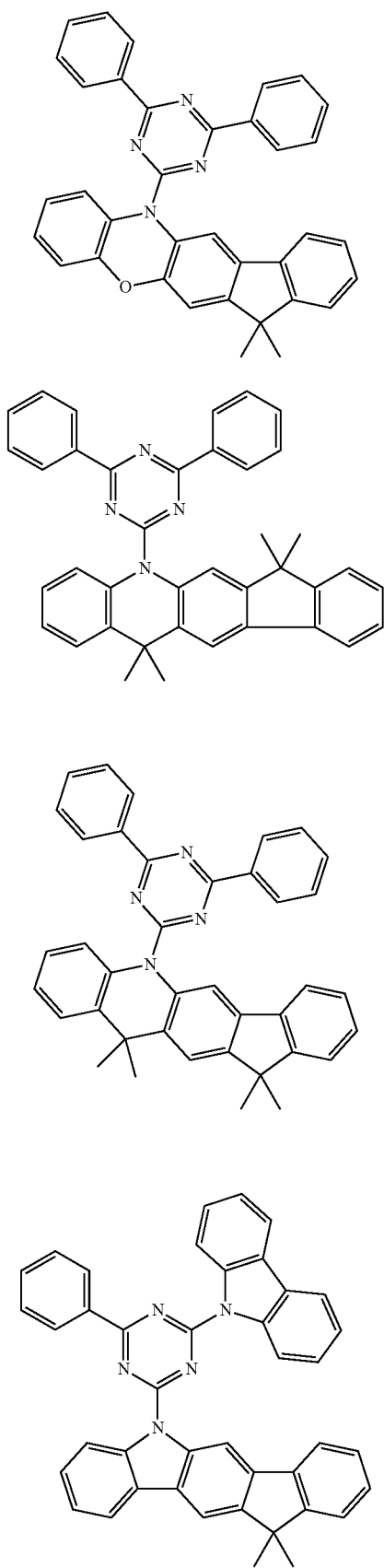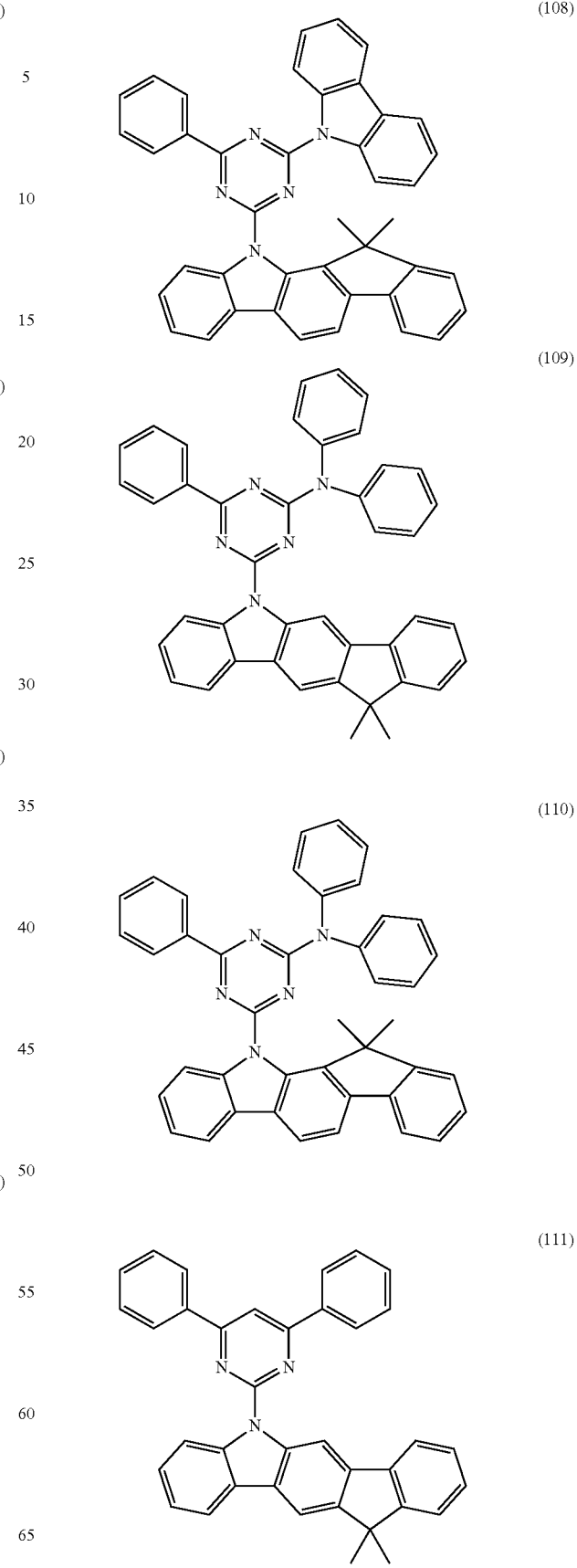

(112) 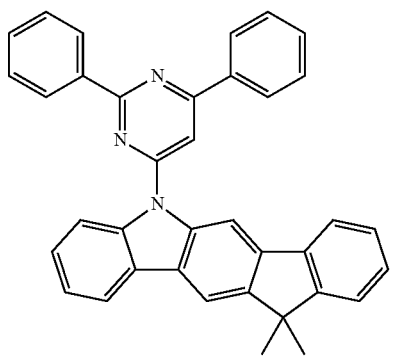
(113) 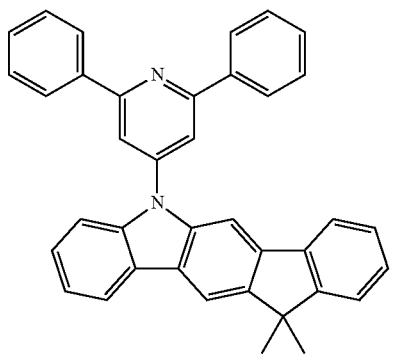
(114) 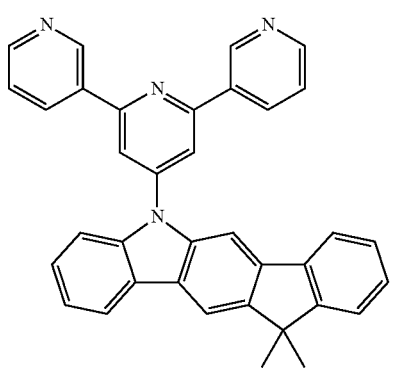
(115) 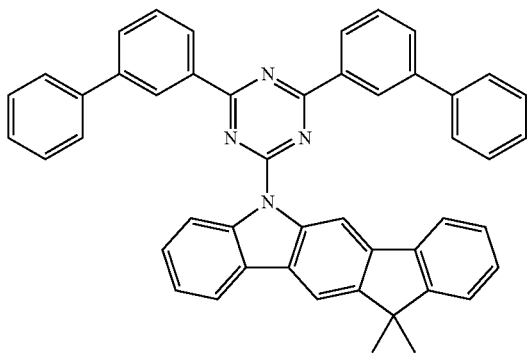
(116) 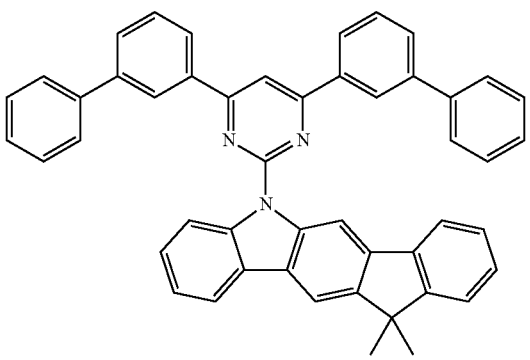
(117) 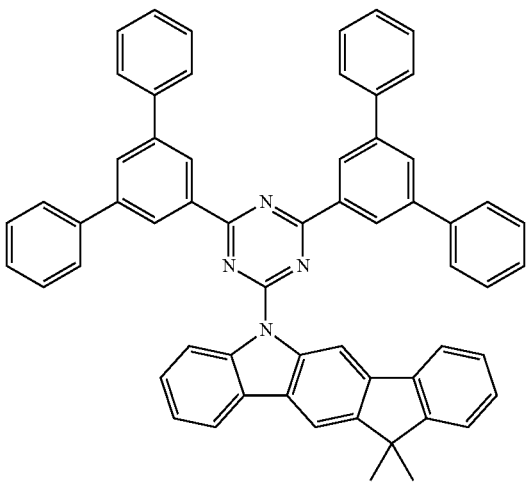
(118) 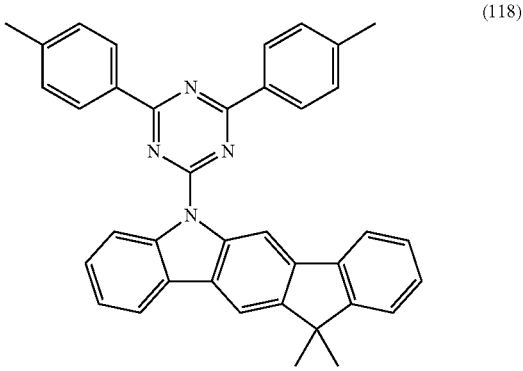
(119) 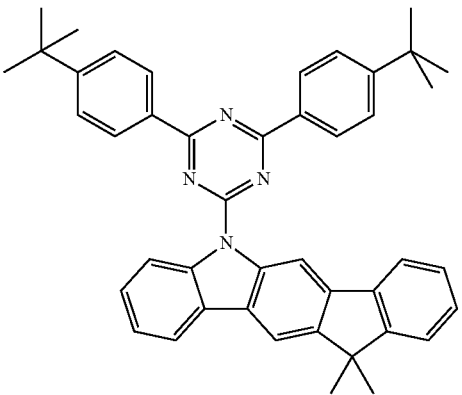

(120)
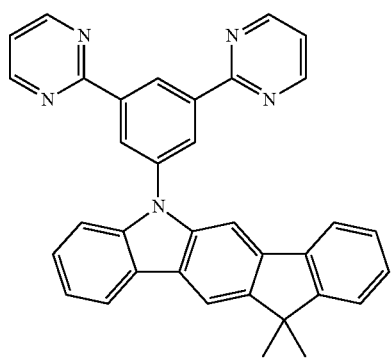
(121)
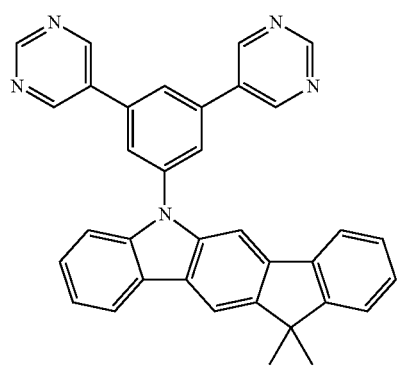
(122)
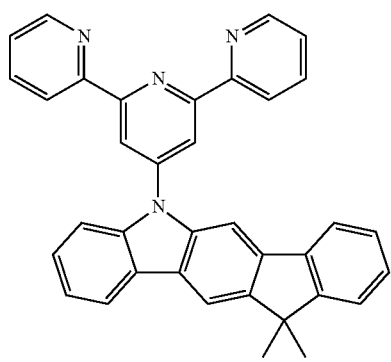
(123)
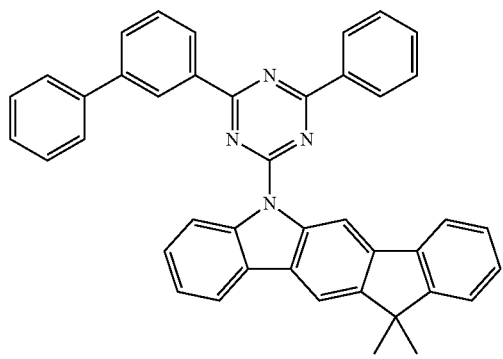
(124)
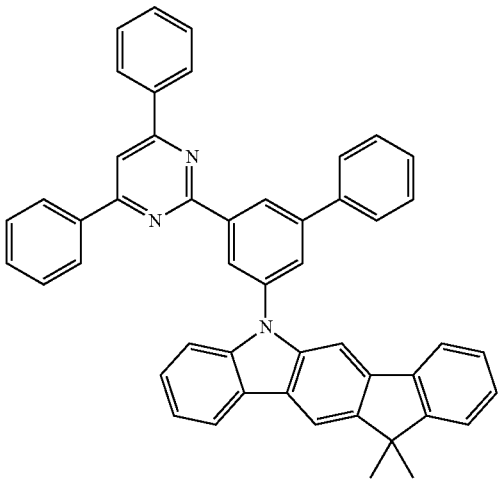
(125)
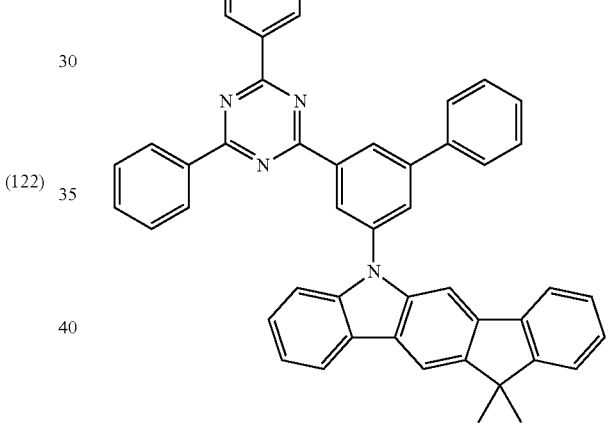
(126)
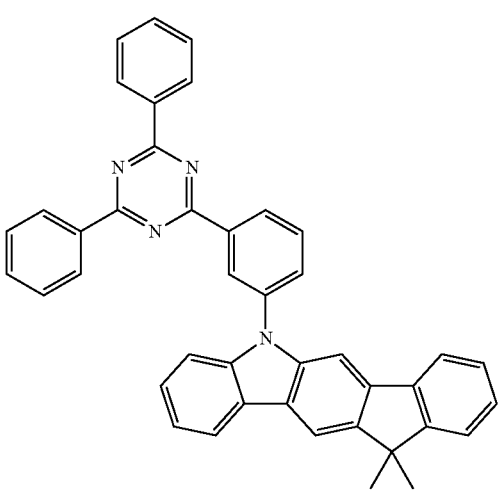

-continued
(127)
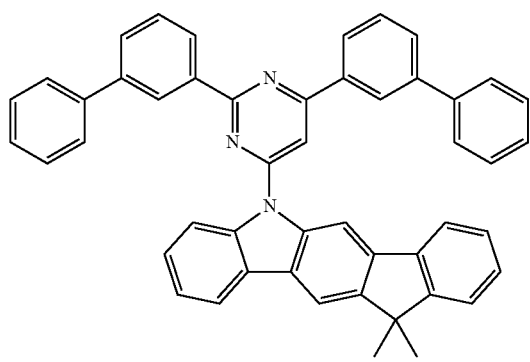
(128)
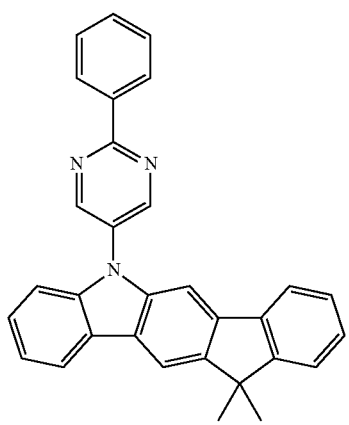
(129)
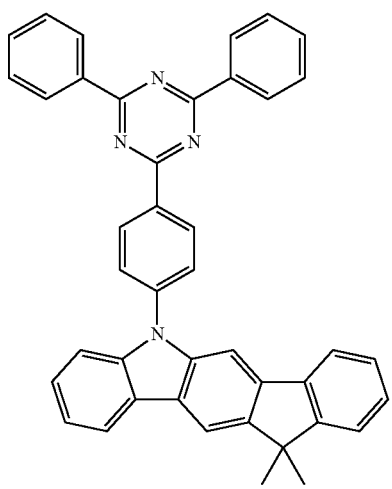
-continued
(130)
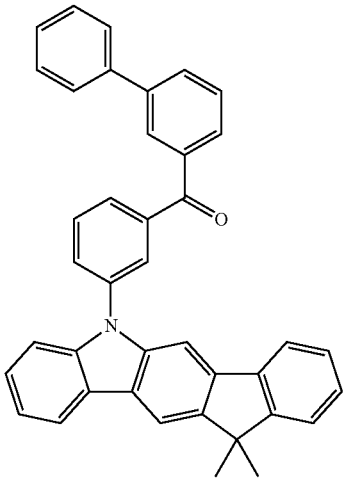
(131)
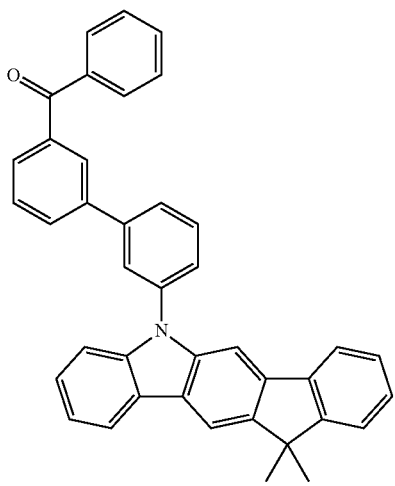
(132)
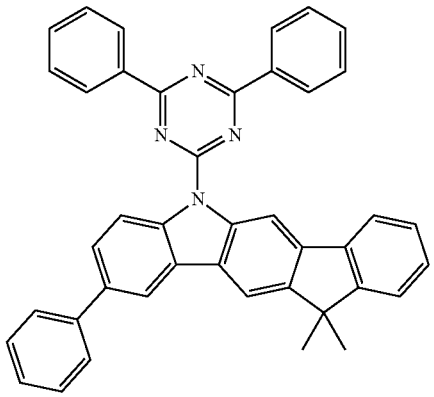

-continued
(133)
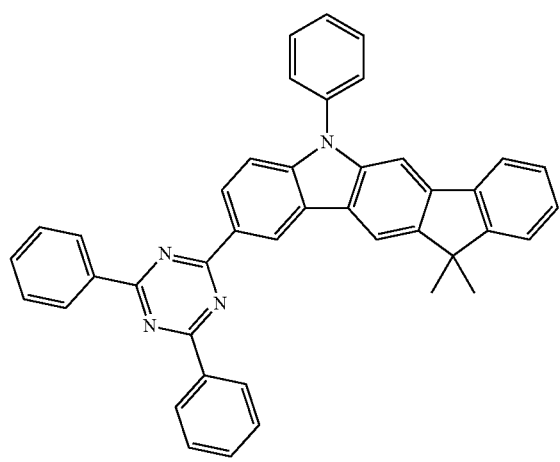
(134)
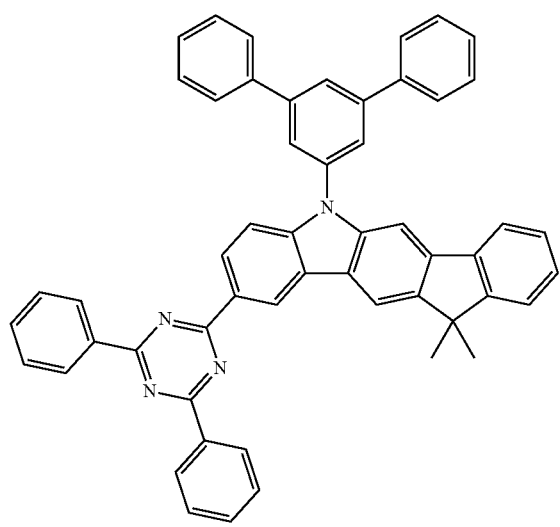
(135)
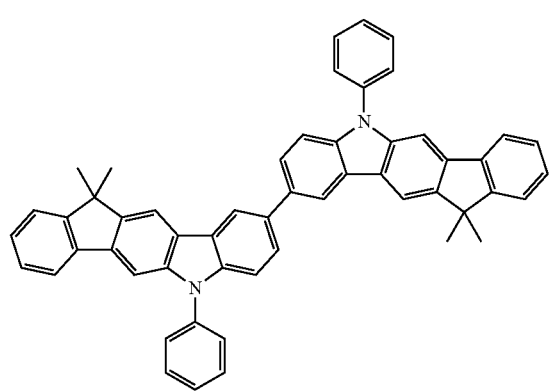
-continued
(136)
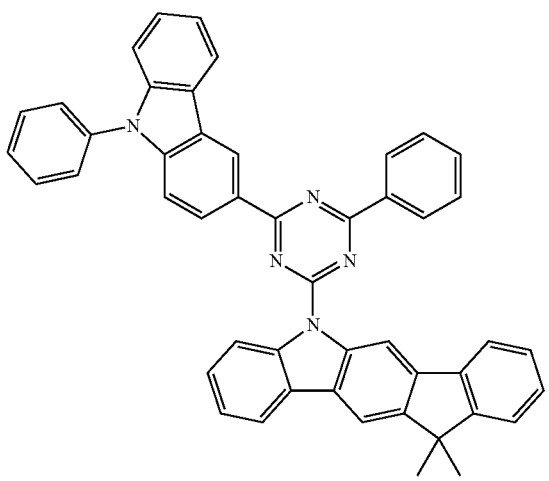
(137)
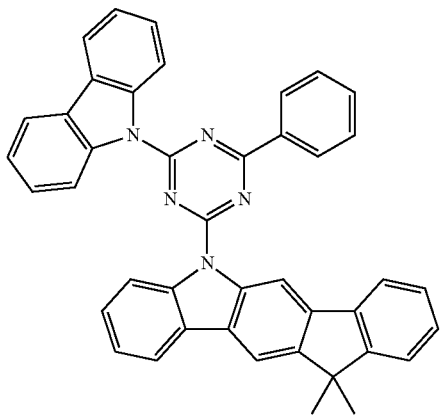
(138)
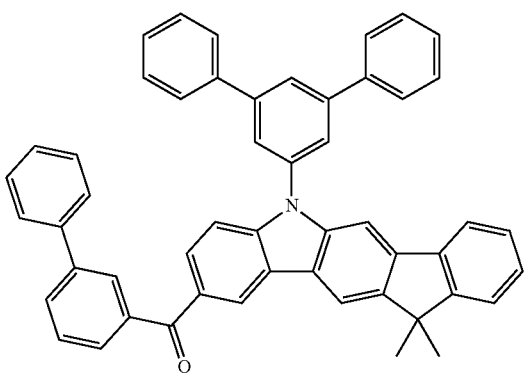

(139)
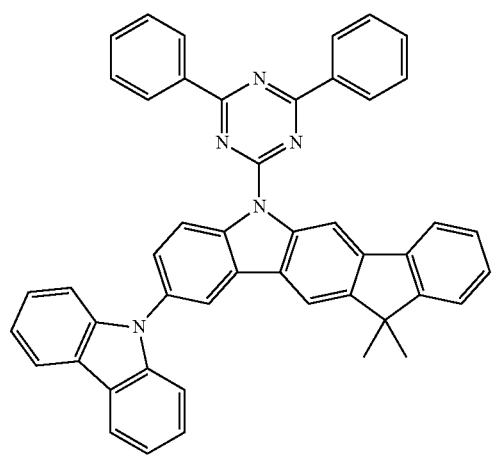
(140)
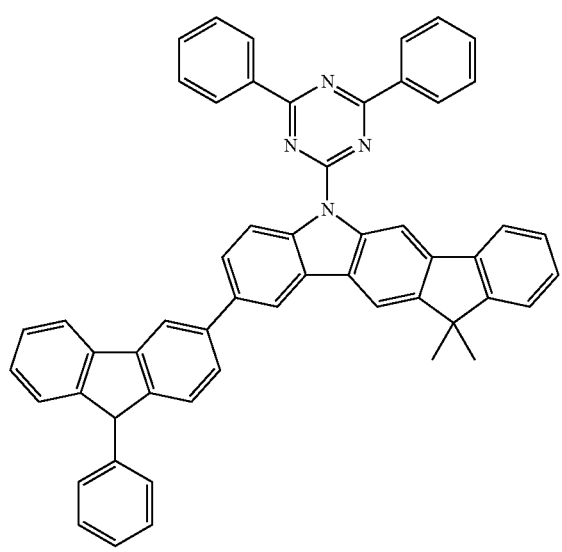
(141)
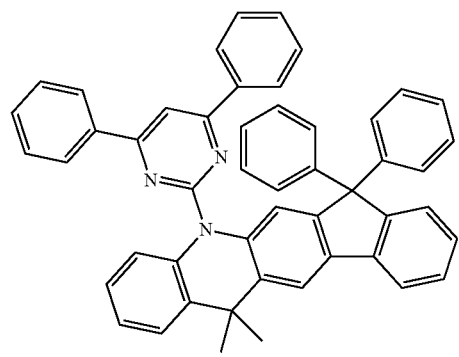
(142)
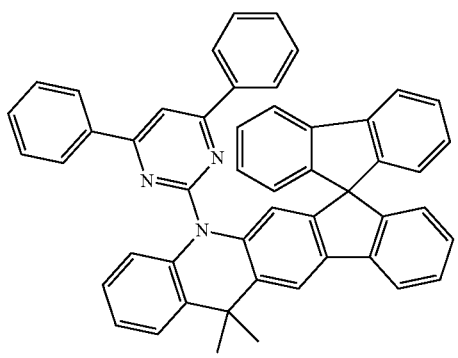
(143)
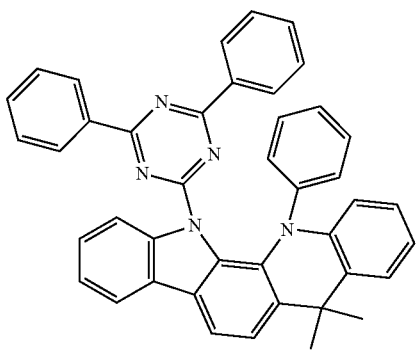
(144)
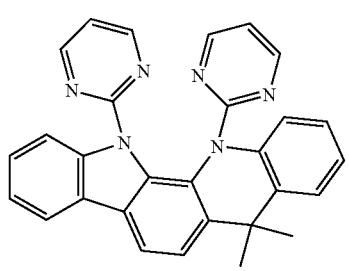
(145)
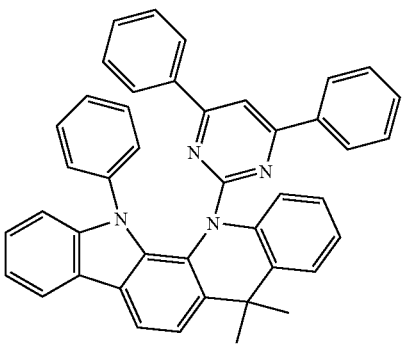

(146)
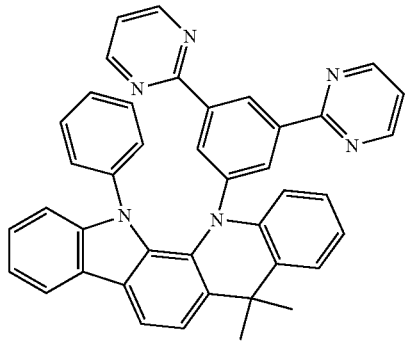
(147)
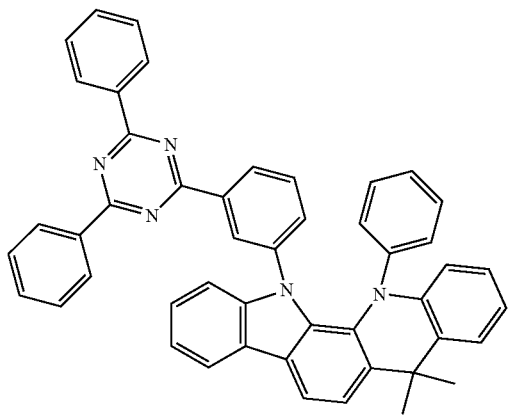
(148)
(149)
(150)
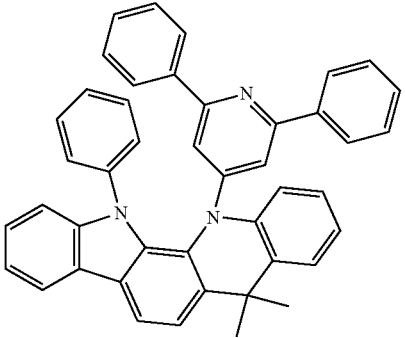
(151)
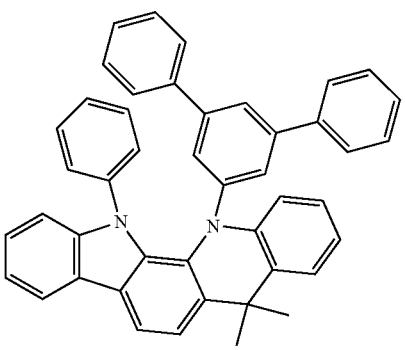
(152)
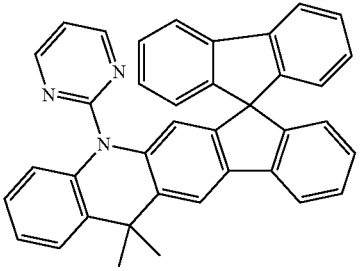
(153)
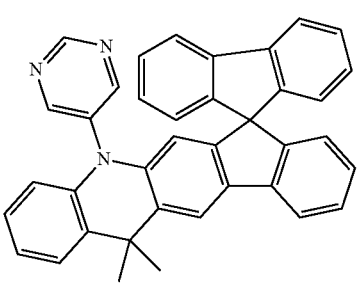

-continued (154)

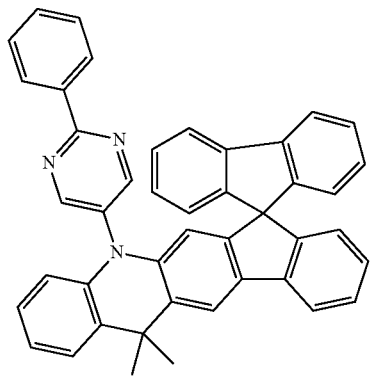

The compounds according to the invention can be prepared by synthetic steps known to the person skilled in the art, such as, for example, bromination, Suzuki coupling, Hartwig-Buchwald coupling, etc. The synthesis of compounds according to the invention is generally represented in Schemes 1 to 3 below.

Scheme 1:

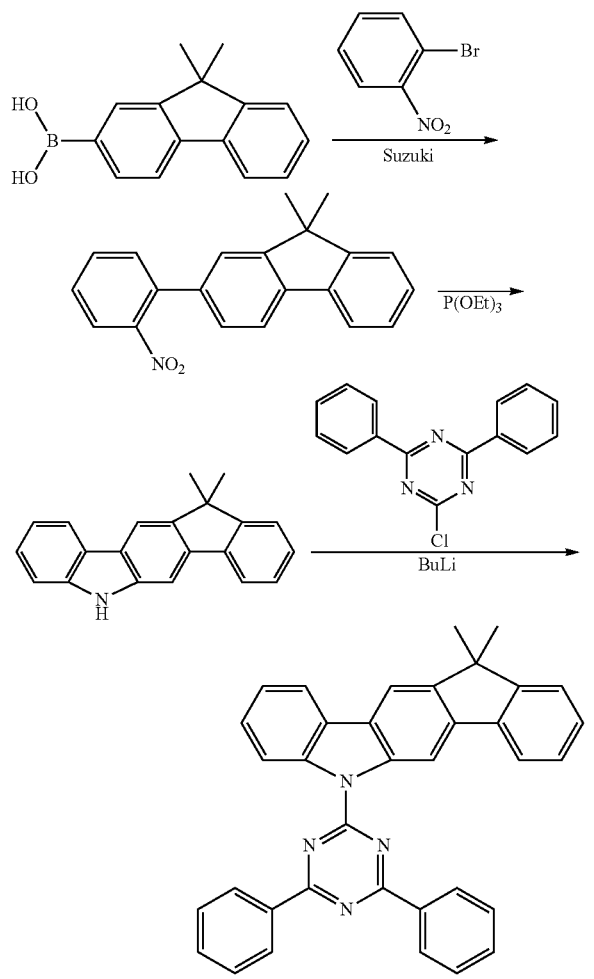

The synthesis starts, for example, from 9,9-dimethylfluorenyl-2-boronic acid (*Synlett,* 2006, 5, 737-740), which is coupled to 1-bromo-2-nitrobenzene in a Suzuki coupling. The nitro group is cyclised under the action of a phosphite, for example triethyl phosphite, giving the corresponding indenocarbazole derivative. The nitrogen can then be alkylated by alkylating agents or arylated in a Hartwig-Buchwald reaction. The group $Ar^1$ can be introduced in this way. The structures may of course also be substituted by further substituents.

An alternative possible preparation is shown in Scheme 2.

Scheme 2:

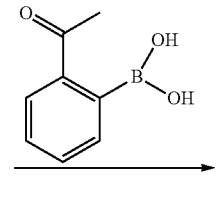

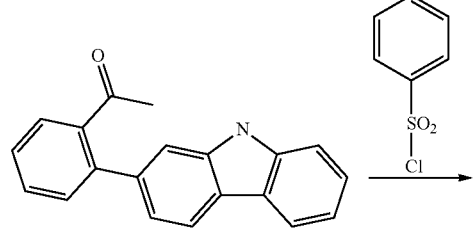

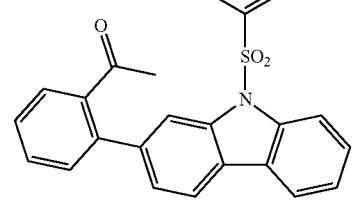

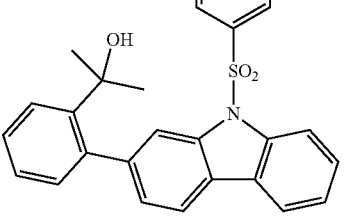

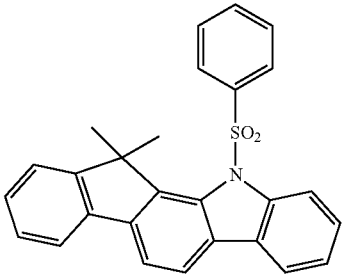

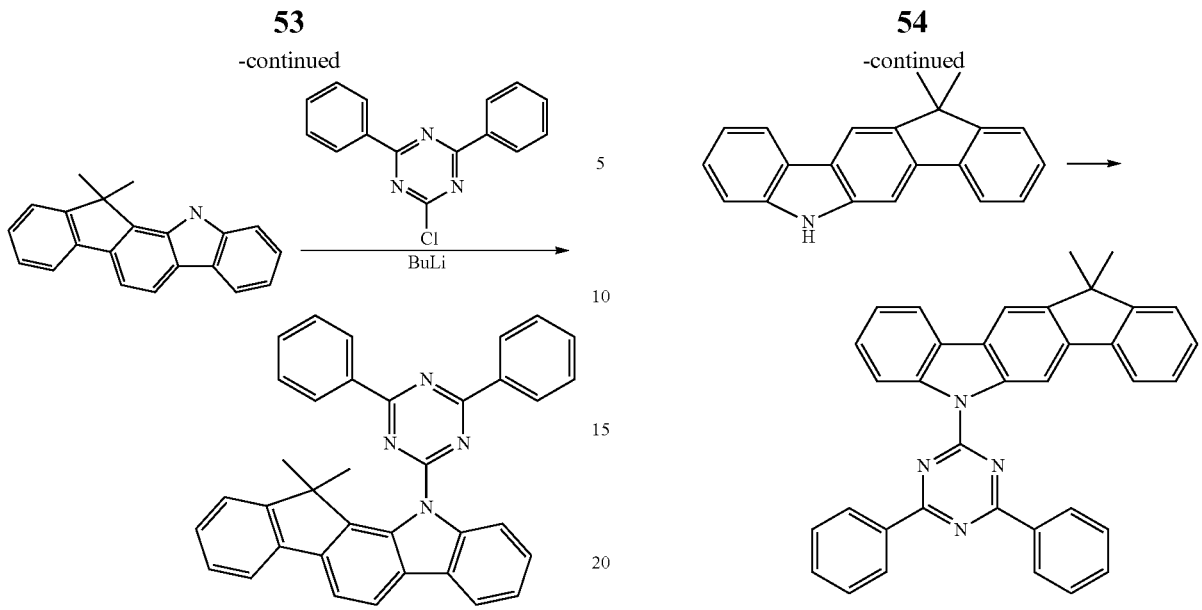

The synthesis starts from a 2-bromocarbazole derivative. This is reacted with a 2-methylcarbonylbenzene-1-boronic acid derivative in a Suzuki coupling. The nitrogen is subsequently protected using a thionyl group. The carbonyl group is reduced to a hydroxyl group using methyllithium. The subsequent cyclisation can be carried out under the action of polyphosphoric acid. After removal of the thionyl protecting group, the nitrogen can then be alkylated by alkylating agents or arylated in a Hartwig-Buchwald reaction. The Ar$^1$ group can be introduced in this way.

A further alternative possible preparation is shown in Scheme 3.

Scheme 3:

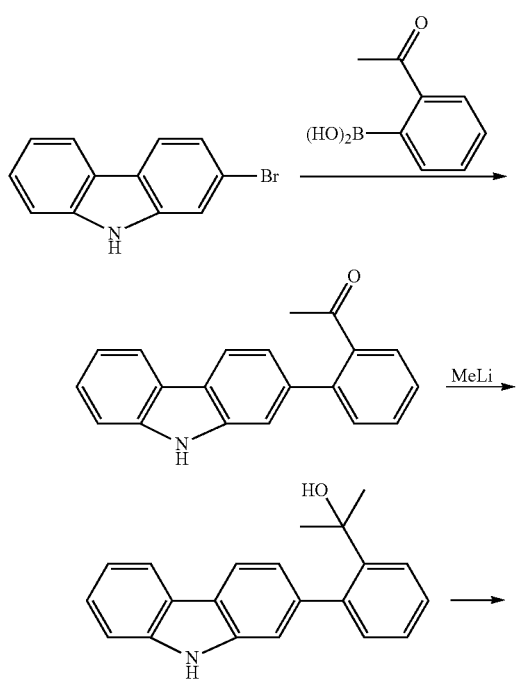

The synthesis starts from a 2-bromofluorene derivative. This is reacted with a 2-methylcarbonylbenzene-1-boronic acid derivative in a Suzuki coupling. The methylcarbonyl group is subsequently reduced to a 1-hydroxyisopropyl group using methyllithium. The subsequent cyclisation can be carried out under the action of polyphosphoric acid. The nitrogen is then either alkylated by alkylating agents or arylated in a Hartwig-Buchwald reaction. The Ar$^1$ group can be introduced in this way.

The invention furthermore relates to a process for the preparation of a compound of the general formula I, comprising the steps of:
a) coupling of a carbazole derivative or fluorene derivative to a benzene derivative, and
b) arylation of the carbazole nitrogen for the introduction of Ar$^1$.

The compounds depicted above can also be used for the preparation of polymers, oligomers or dendrimers. This is usually carried out via polymerisable functional groups. To this end, particular preference is given to compounds which are substituted by reactive leaving groups, such as bromine, iodine, boronic acid, boronic acid ester, tosylate or triflate. These can be used as comonomers for the generation of corresponding conjugated, partially conjugated or non-conjugated polymers, oligomers or also as the core of dendrimers. The polymerisation here is preferably carried out via the halogen functionality or the boronic acid functionality. The polymers may also contain crosslinkable groups or be crosslinked. Particularly suitable are crosslinkable groups which are then crosslinked in the layer of the electronic device.

The invention thus furthermore relates to polymers, oligomers or dendrimers comprising one or more compounds of the formula I, where one or more radicals or H atoms of the compounds defined above represent a bond to the polymer, oligomer or dendrimer. The polymers, oligomers or dendrimers here may be conjugated, partially conjugated or non-conjugated. Mixtures (blends) of the polymers, oligomers or dendrimers according to the invention with further polymers, oligomers or dendrimers are likewise encompassed.

For the purposes of this invention, an oligomer denotes a compound which has about three to nine recurring units. For the purposes of the invention, a polymer is taken to mean a compound which has ten or more recurring units.

These oligomers or polymers may contain further recurring units. These further recurring units are preferably selected from the group consisting of fluorenes (for example in accordance with EP 842208 or WO 2000/22026), spirobifluorenes (for example in accordance with EP 707020, EP 894107 or EP 04028865.6), triarylamines, para-phenylenes (for example in accordance with WO 92/18552), carbazoles (for example in accordance with WO 2004/070772 and WO 2004/113468), thiophenes (for example in accordance with EP 1028136), dihydrophenanthrenes (for example in accordance with WO 2005/014689), indenofluorenes (for example in accordance with WO 2004/041901 and WO 2004/113412), aromatic ketones (for example in accordance with WO 2005/040302), phenanthrenes (for example in accordance with WO 2005/104264) and/or metal complexes, in particular ortho-metallated iridium complexes. It should expressly be pointed out here that the polymers may also contain a plurality of different recurring units selected from one or more of the above-mentioned groups.

The compounds of the formula I can be employed in electronic devices, in particular in organic electroluminescent devices. The precise use of the compounds depends on the substituents.

The invention therefore furthermore relates to the use of the compounds of the formula I or the polymers, oligomers or dendrimers defined above in electronic devices.

The invention furthermore relates to an electronic device comprising at least one compound, as defined above, or a polymer, oligomer or dendrimer, as defined above. The invention likewise encompasses mixtures (blends) of the oligomers, polymers or dendrimers according to the invention, optionally with further oligomers, polymers or dendrimers which are different therefrom or with further low-molecular-weight compounds.

The electronic device is preferably selected from the group consisting of organic electroluminescent devices (OLEDs), organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic photoreceptors or organic laser diodes (O-lasers).

The present invention also relates to organic electroluminescent devices which are characterised in that a plurality of emitting compounds are used in the same layer or in different layers. The compound of the formula I according to the invention can be employed either as matrix material in an emitting layer or as electron-transport material in an electron-transport layer or as hole-transport material in a hole-transport layer. However, compounds according to the invention can also be employed in a plurality of the said layers. These emission layers particularly preferably have in total a plurality of emission maxima between 380 nm and 750 nm, resulting overall in white emission, i.e. various emitting compounds which are able to fluoresce or phosphoresce and emit blue and yellow, orange or red light are used in the emitting layers. Particular preference is given to three-layer systems, i.e. systems having three emitting layers, where at least one of these layers comprises at least one compound of the formula I and at least one phosphorescent emitter and where the three layers exhibit blue, green and orange or red emission (for the basic structure see, for example, WO 2005/011013). The use of more than three emitting layers may also be preferred. Emitters which have broad-band emission bands and thus exhibit white emission are likewise suitable for white emission.

Apart from the cathode, the anode and at least one of the layers mentioned above, the organic electroluminescent device may also comprise further layers. These can be, for example: hole-injection layer, electron-blocking layer, hole-blocking layer, electron-injection layer and/or charge-generation layer. However, it should be pointed out at this point that each of these layers does not necessarily have to be present. Thus, in particular on use of compounds of the formula I with electron-conducting host materials, very good results are furthermore obtained if the organic electroluminescent device does not comprise a separate electron-transport layer and the emitting layer is directly adjacent to the electron-injection layer or the cathode. Alternatively, the host material may also simultaneously serve as electron-transport material in an electron-transport layer. It may likewise be preferred for the organic electroluminescent device not to comprise a separate hole-transport layer and for the emitting layer to be directly adjacent to the hole-injection layer or the anode.

For the purposes of the invention, it is preferred for the compounds of the formula I according to the invention or the polymers, oligomers or dendrimers according to the invention to be employed as matrix material for phosphorescent dopants in the electronic device.

For the purposes of the invention, it is furthermore preferred for the compounds of the formula I according to the invention or the polymers, oligomers or dendrimers according to the invention to be employed as electron-transport material in an electron-transport layer and/or as hole-transport material in a hole-transport layer and/or as hole-blocking material in a hole-blocking layer in the electronic device.

An organic electroluminescent device is a device which comprises an anode, a cathode and at least one emitting layer which is arranged between the anode and the cathode. In addition, in each case one or more electron-transport layers and/or hole-transport layers may also be present. An organic electroluminescent device according to the invention comprises at least one layer which comprises a compound of the formula I between the anode and the cathode.

In a further embodiment of the present invention, the compounds of the formula I are employed as matrix material for emitting materials, preferably phosphorescent dopants. It is particularly preferred here for the compounds of the formula I to be employed as matrix material for emitting materials in an organic electroluminescent device.

In a further preferred embodiment of the invention, the organic electroluminescent device may also comprise a plurality of emitting layers, where at least one emitting layer comprises at least one compound of the formula I and at least one, preferably phosphorescent, emitter.

The invention therefore furthermore also relates to mixtures of one or more compounds of the formula I with one or more emitting compounds, in particular phosphorescent compounds.

The mixture of the compound of the formula I and the phosphorescent emitter employed in the emitting layer preferably comprises between 99 and 50% by vol., preferably between 98 and 50% by vol., particularly preferably between 97 and 60% by vol., in particular between 95 and 85% by vol., of the compound of the formula I, based on the entire mixture comprising emitter and matrix material. Correspondingly, the mixture comprises between 1 and 50% by vol., preferably between 2 and 50% by vol., particularly preferably between 3 and 40% by vol., in particular between 5 and 15% by vol., of the phosphorescent emitter, based on the entire mixture comprising emitter and matrix material.

A further preferred embodiment of the present invention is the use of the compound according to the invention as matrix material for a phosphorescent emitter in combination with a further matrix material. Particularly suitable matrix materials which can be employed in combination with the compounds according to the invention are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, diazasilole or tetraazasilole derivatives, for example in accordance with the unpublished application DE 102008056688.8, diazaphosphole derivatives, for example in accordance with the unpublished application DE 102009022858.6, or indenocarbazole derivatives, for example in accordance with the unpublished application DE 102009023155.2.

Suitable phosphorescent compounds (=triplet emitters) are, in particular, compounds which emit light, preferably in the visible region, on suitable excitation and in addition contain at least one atom having an atomic number of greater than 20, preferably greater than 38 and less than 84, particularly preferably greater than 56 and less than 80. The phosphorescent emitters used are preferably compounds which contain copper, molybdenum, tungsten, rhenium, ruthenium, osmium, rhodium, iridium, palladium, platinum, silver, gold or europium, in particular compounds which contain iridium or platinum.

Examples of the emitters described above are revealed by the applications WO 00/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as used in accordance with the prior art for phosphorescent OLEDs and as are known to the person skilled in the art in the area of organic electroluminescence are suitable, and the person skilled in the art will be able to use further phosphorescent complexes without inventive step.

It may also be preferred to use two or more different phosphorescent emitters in an emitting layer, in particular emitters which have different emission maxima. Thus, the use, for example, of a green-phosphorescent emitter and a red-phosphorescent emitter enables red luminescence to be achieved with improved efficiency.

In a further embodiment of the invention, the organic electroluminescent device according to the invention does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 2005/053051. It is furthermore possible to use a metal complex which is identical or similar to the metal complex in the emitting layer, directly adjacent to the emitting layer, as hole-transport or hole-injection material, as described, for example, in WO 2009/030981.

In a further embodiment of the present invention, the compounds of the formula I are employed as electron-transport material, preferably in an electron-transport layer. Particularly preferred compounds in this case are compounds of the formula I which contain, as $Ar^1$, an electron-deficient heteroaromatic group, as described in greater detail above.

If the compounds of the formula I are employed as electron-transport material in an organic electroluminescent device, they can also be employed in accordance with the invention in combination with an organic or inorganic alkali metal compound. "In combination with an organic alkali metal compound" here means that the compounds of the formula I and the alkali metal compound are either in the form of a mixture in one layer or separately in two successive layers. In a preferred embodiment of the invention, the compounds of the formula I and the organic alkali metal compound are in the form of a mixture in one layer.

For the purposes of this invention, an organic alkali metal compound is intended to be taken to mean a compound which contains at least one alkali metal, i.e. lithium, sodium, potassium, rubidium or caesium, and which furthermore contains at least one organic ligand. Suitable organic alkali metal compounds are, for example, the compounds disclosed in WO 2007/050301, WO 2007/050334 and EP 1144543. These are incorporated into the present application by way of reference.

Preferred organic alkali metal compounds are the compounds of the following formula A:

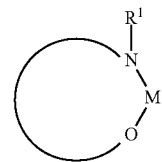

formula A where $R^1$ has the same meaning as described above, the curved line represents two or three atoms and bonds which are necessary to make up a 5- or 6-membered ring with M, where these atoms may also be substituted by one or more radicals $R^1$, and M represents an alkali metal selected from the group consisting of lithium, sodium, potassium, rubidium or caesium.

It is possible here for the complex of the formula A to be in monomeric form, as depicted above, or for it to be in the form of aggregates, for example comprising two alkali metal ions and two ligands, four alkali metal ions and four ligands, six alkali metal ions and six ligands, or other aggregates.

Preferred compounds of the formula A are the compounds of the following formulae B and C:

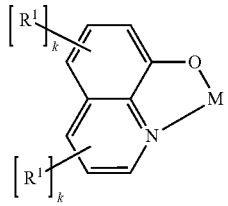

formula B formula C

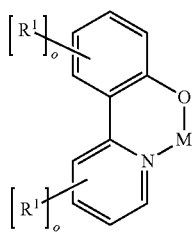

where k is equal to 0, 1, 2 or 3 and o is equal to 0, 1, 2, 3 or 4, and the other symbols used have the meanings mentioned above.

Further preferred organic alkali metal compounds are the compounds of the following formula D:

formula D

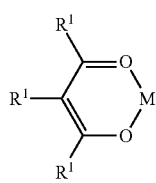

where the symbols used have the same meaning as described above.

The alkali metal is preferably selected from lithium, sodium and potassium, particularly preferably lithium and sodium, very particularly preferably lithium.

Particular preference is given to a compound of the formula B, in particular where M=lithium. The index k is furthermore very particularly preferably =0. The compound is thus very particularly preferably unsubstituted lithium quinolinate.

The organic electroluminescent device very particularly preferably comprises a mixture of a compound of the formula I, where $Ar^1$ is equal to an electron-deficient heteroaromatic group, and an organic alkali metal compound of the formula B, preferably where M=lithium, in particular unsubstituted lithium quinolinate.

Examples of suitable organic alkali metal compounds are structures (1) to (45) shown in the following table.

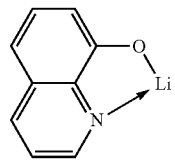

(1)

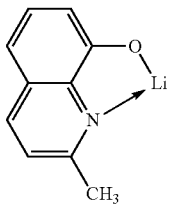

(2)

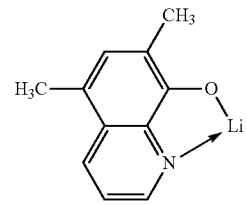

(3)

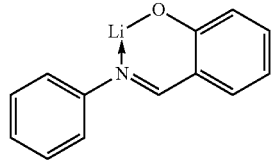

(4)

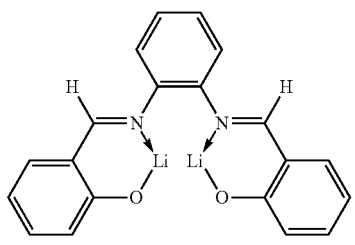

(5)

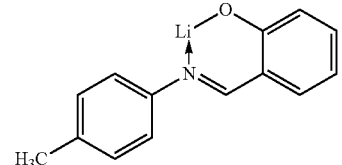

(6)

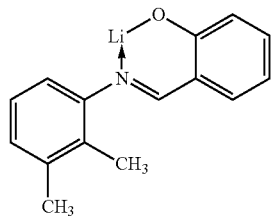

(7)

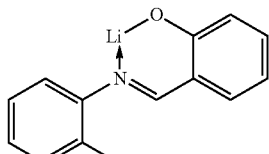

(8)

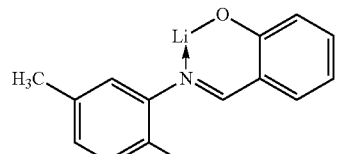

(9)

-continued
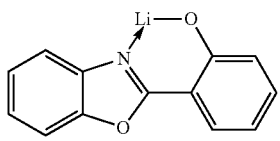
(10)
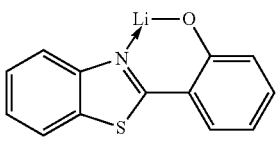
(11)
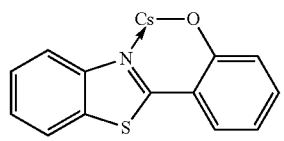
(12)
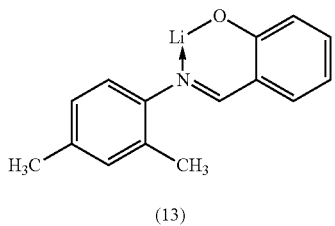
(13)
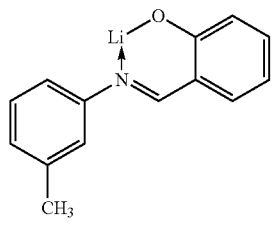
(14)
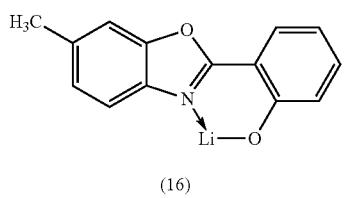
(15)
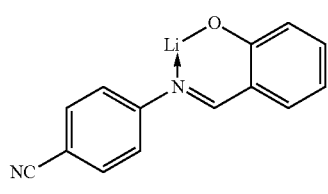
(16)
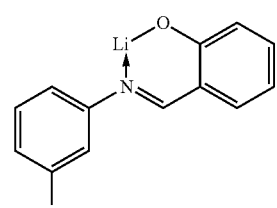
(17)
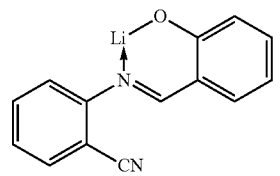
(18)
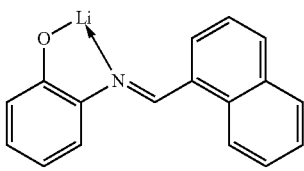
(19)
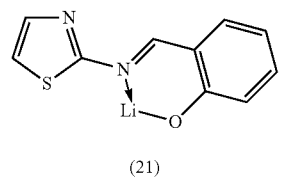
(20)
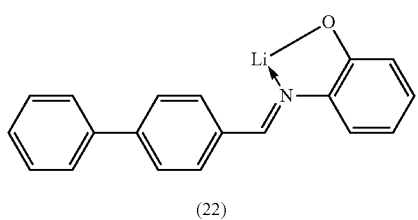
(21)
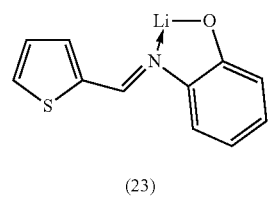
(22)
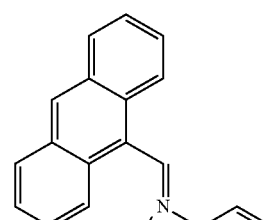
(23)
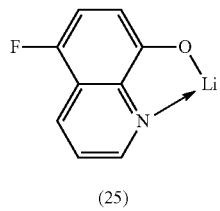
(24)
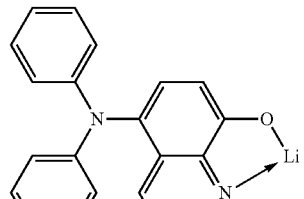
(25)
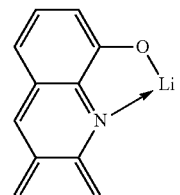
(26)
(27)

-continued
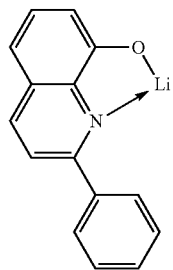
(28)
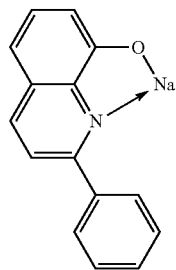
(29)
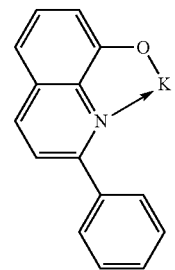
(30)
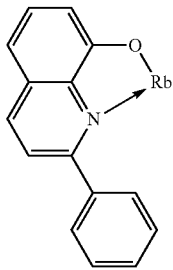
(31)
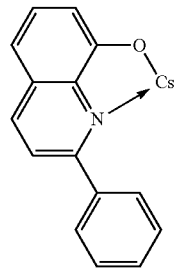
(32)
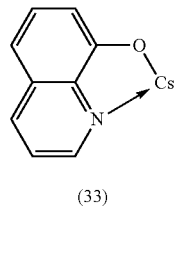
(33)
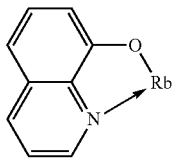
(34)
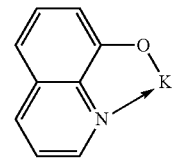
(35)
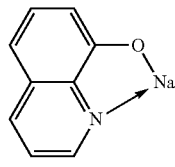
(36)
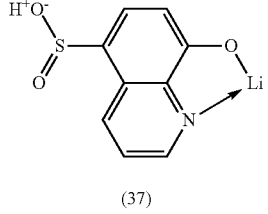
(37)
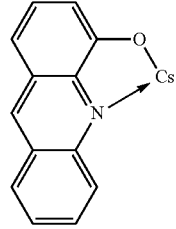
(38)
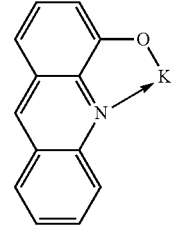
(39)
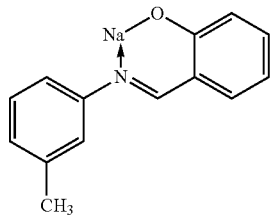
(40)
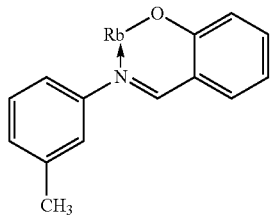
(41)
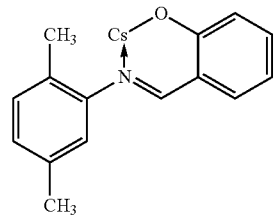
(42)
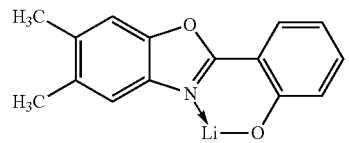
(43)
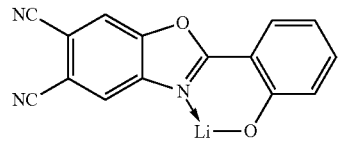
(44)
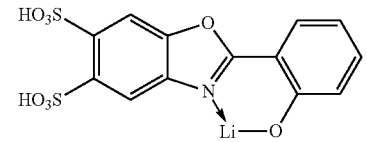
(45)

If the compound of the formula I and the organic or inorganic alkali metal compound are in the form of a mixture, the ratio of the compound of the formula I to the organic alkali metal compound is preferably 20:80 to 80:20, particularly preferably 30:70 to 70:30, very particularly preferably 30:70 to 50:50, in particular 30:70 to 45:55, in each case based on the volume. The organic alkali metal compound is thus particularly preferably present in a higher proportion than the compound of the formula I.

If the compound of the formula I and the organic or inorganic alkali metal compound are in the form of a mixture, the layer thickness of this electron-transport layer is preferably between 3 and 150 nm, particularly preferably between 5 and 100 nm, very particularly preferably between 10 and 60 nm, in particular between 15 and 40 nm.

If the compound of the formula I and the organic or inorganic alkali metal compound are in two successive layers, the layer thickness of the layer which comprises the compound of the formula I is preferably between 3 and 150 nm, particularly preferably between 5 and 100 nm, very particularly preferably between 10 and 60 nm, in particular between 15 and 40 nm. The layer thickness of the layer which comprises the organic or inorganic alkali metal compound and which is arranged between the layer comprising the compound of the formula I and the cathode is preferably between 0.5 and 20 nm, particularly preferably between 1 and 10 nm, very particularly preferably between 1 and 5 nm, in particular between 1.5 and 3 nm.

The present invention furthermore relates to the use of the compounds of the formula I as hole-blocking material. The compounds are then preferably employed in a hole-blocking layer, in particular in a phosphorescent OLED. For the purposes of this invention, a hole-blocking layer is a layer which is arranged between an emitting layer and an electron-transport layer.

The present invention furthermore relates to the use of the compounds of the formula I as hole-transport material and/or as hole-injection material. The compounds are then preferably employed in a hole-transport layer and/or in a hole-injection layer. For the purposes of this invention, a hole-injection layer is a layer which is directly adjacent to the anode. For the purposes of this invention, a hole-transport layer is a layer which is located between the hole-injection layer and the emission layer.

The cathode preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). In the case of multilayered structures, further metals which have a relatively high work function, such as, for example, Ag, can also be used in addition to the said metals, in which case combinations of the metals, such as, for example, Mg/Ag, Ca/Ag or Ba/Ag, are generally used. Preference is likewise given to metal alloys, in particular alloys comprising an alkali metal or alkaline-earth metal and silver, particularly preferably an alloy of Mg and Ag. It may also be preferred to introduce a thin interlayer of a material having a high dielectric constant between a metallic cathode and the organic semiconductor. Suitable for this purpose are, for example, alkali metal or alkaline-earth metal fluorides, but also the corresponding oxides or carbonates (for example LiF, $Li_2O$, CsF, $Cs_2CO_3$, $BaF_2$, MgO, NaF, etc.). The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/$NiO_x$, Al/$PtO_x$, $WoO_3$) may also be preferred. For some applications, at least one of the electrodes must be transparent or partially transparent in order to facilitate either irradiation of the organic material (O-SCs) or the coupling-out of light (OLEDs/PLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive, doped polymers.

The device is appropriately (depending on the application) structured, provided with contacts and finally hermetically sealed, since the lifetime of such devices is drastically shortened in the presence of water and/or air.

Compounds of the formula I can also be employed in polymers, oligomers or dendrimers as hole-transporting unit and/or as electron-transporting unit and/or as matrix for phosphorescent units.

Preference is furthermore given to an organic electroluminescent device, characterised in that one or more layers are applied by means of a sublimation process, in which the materials are vapour-deposited in vacuum sublimation units at an initial pressure of less than $10^{-5}$ mbar, preferably less than $10^{-6}$ mbar. However, it should be noted that the initial pressure may also be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, offset printing, LITI (light induced thermal imaging, thermal transfer printing), inkjet printing or nozzle printing. Soluble compounds of the formula I are necessary for this purpose. High solubility can be achieved through suitable substitution of the compounds. These processes for the production of layers are also particularly suitable for polymers, oligomers or dendrimers.

The organic electroluminescent device may also be produced as a hybrid system by applying one or more layers from solution and applying one or more other layers by vapour deposition. Thus, for example, it is possible to apply an emitting layer comprising a compound of the formula I and a phosphorescent dopant from solution and to apply a hole-blocking layer and/or an electron-transport layer on top by vacuum vapour deposition. The emitting layer comprising a compound of the formula I and a phosphorescent dopant can likewise be applied by vacuum vapour deposition, and one or more other layers can be applied from solution. Alternatively or in addition, it is also possible, for example, to apply an emitting layer from solution and to apply an electron-transport layer comprising a compound of the formula I, optionally in combination with an organic alkali metal compound, on top by vacuum vapour deposition.

These processes are generally known to the person skilled in the art and can be applied by him without problems to organic electroluminescent devices comprising compounds of the formula I or the preferred embodiments indicated above.

For application from solution, solutions or formulations of the compound according to the invention are necessary. The present invention therefore furthermore relates to a formulation comprising at least one compound of the formula I and at least one organic solvent. All organic solvents as usually used for the production of organic electroluminescent devices can be used here.

The present invention furthermore relates to mixtures comprising at least one phosphorescent emitter and at least one compound of the formula I.

The compounds according to the invention have the following surprising advantages over the prior art on use in organic electroluminescent devices:

1. The compounds according to the invention are very highly suitable for use as matrix material for phosphorescent emitters and, in this use, result in good efficiencies, long lifetimes and low operating voltages.

2. The power efficiency of corresponding devices is increased compared with systems in accordance with the prior art, in particular on use of thick layers. This applies, in particular, on use of the compound according to the invention in an electron-transport layer.

3. The stability of corresponding devices is increased compared with systems in accordance with the prior art, which is evident, in particular, from a significantly longer lifetime, in particular on use of thick layers.

4. The organic electroluminescent devices according to the invention simultaneously have a reduced operating voltage.

5. The organic electroluminescent devices according to the invention have very high efficiency. The improved efficiency may possibly be attributable to improved electron injection from the electron-transport layer into the emitting layer.

Finally, it should be noted that all features of the above-mentioned compounds according to the invention which are preferred and all those which are not explicitly mentioned as preferred, the use thereof in electronic devices and the electronic devices themselves can be combined with one another as desired. This invention likewise relates to all resultant combinations.

The invention is now explained in greater detail by the following examples, without wishing to restrict it thereby. The person skilled in the art will be able, without being inventive, to synthesise further compounds according to the invention and employ them in electronic devices.

EXAMPLES

The following syntheses are, unless indicated otherwise, carried out under a protective-gas atmosphere in dried solvents.

Example 1

2-(2-Nitrophenyl)-9,9-dimethyl-9H-fluorene

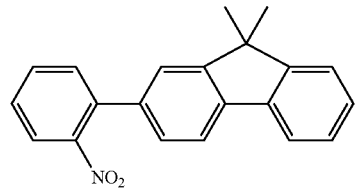 [SMILES: CC1(C)c2ccccc2-c2ccc(-c3ccccc3[N+](=O)[O-])cc21]

913 mg (3 mmol) of tri-o-tolylphosphine and then 112 mg (0.5 mmol) of palladium(II) acetate are added to a vigorously stirred suspension of 23.8 g (100 mmol) of 9,9-dimethylfluorenyl-2-boronic acid, 20.6 g (102 mmol) of 1-bromo-2-nitrobenzene, 51 g (221 mmol) of tripotassium phosphate in a mixture of 380 ml of toluene, 190 ml of dioxane and 480 ml of water, and the mixture is subsequently heated under reflux for 16 h. After cooling, the solid which has precipitated out is filtered off with suction, washed three times with 50 ml of toluene, three times with 50 ml of ethanol:water (1:1, v:v) and three times with 100 ml of ethanol and recrystallised three times from DMF (about 10 ml/g). Yield: 25.3 g (80 mmol), 81%.

Example 2

12,12-Dimethyl-6,12-dihydro-6-azaindeno[1,2-b]fluorene

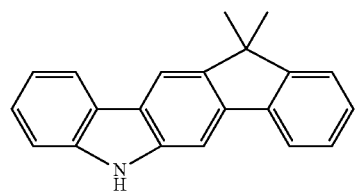 [SMILES: CC1(C)c2ccccc2-c2cc3[nH]c4ccccc4c3cc21]

A mixture of 75 g (238 mmol) of 2-(2-nitrophenyl)-9,9-dimethyl-9H-fluorene and 290.3 ml (1669 mmol) of triethyl phosphite is heated under reflux for 12 h. The triethyl phosphite which remains is subsequently removed by distillation (72-76° C./9 mm Hg). Water/MeOH (1:1) is added to the residue, and the solid is filtered off and recrystallised. Yield: 61.3 g (216 mmol), 92%.

Example 3a 6-(4,6-Diphenyl-1,3,5-triazin-2-yl)-12,12-dimethyl-6,12-dihydro-6-azaindeno[1,2-b]fluorene

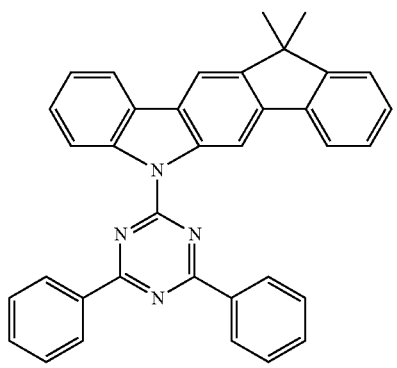 [SMILES: CC1(C)c2ccccc2-c2cc3c(cc21)c1ccccc1n3-c1nc(-c2ccccc2)nc(-c2ccccc2)n1]

1.5 g (37.5 mmol) of NaH (60% in oil) are initially introduced in 150 ml of dichloromethane. A solution of 8 g (28 mmol) of 12,12-dimethyl-6,12-dihydro-6-azaindeno[1,2-b]fluorene in dichloromethane is added dropwise at room temperature. After 1 h, 8.5 g (31 mmol) of 2-chloro-4,6-diphenyl-1,3,5-triazine are added dropwise, and the mixture is stirred at RT for 8 h. The solid which has precipitated out is recrystallised from toluene. The crystals which have deposited are filtered off with suction, washed with a little MeOH and dried in vacuo; yield: 11.6 g; 80% of theory; purity: 99.9% according to HPLC.

The following compounds are obtained analogously:

| Ex. | Starting material 1 | Product | Yield |
|---|---|---|---|
| 3b | 222-21-9 | | 83% |
| 3c | 222-21-9 | | 78% |
| 3d | 237-97-8 | | 86% |

-continued
| Ex. | Starting material 1 | Product | Yield |
|---|---|---|---|
| 3e | 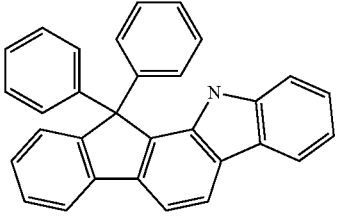 [SMILES: c1ccc(C2(c3ccccc3)c3ccccc3-c3ccc4c([nH]c5ccccc54)c32)cc1]<br>1190100-22-1 | 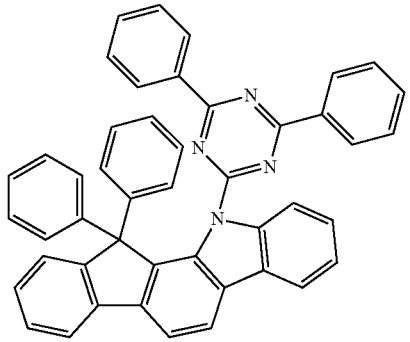 [SMILES: c1ccc(-c2nc(-c3ccccc3)nc(-n3c4ccccc4c4ccc5c(c43)C(c3ccccc3)(c3ccccc3)c3ccccc3-5)n2)cc1] | 77% |
| 3f | 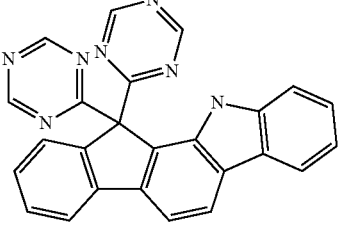<br>1190100-24-3 | 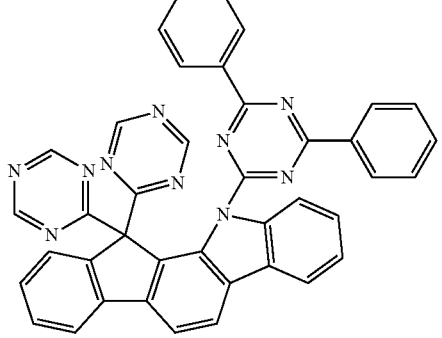 | 72% |
| 3g | 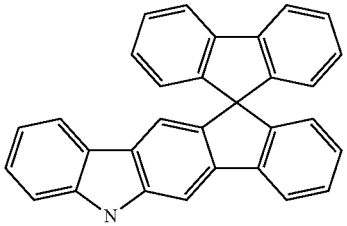 [SMILES: c1ccc2c(c1)-c1ccccc1C21c2ccccc2-c2cc3[nH]c4ccccc4c3cc21]<br>1207061-08-2 | 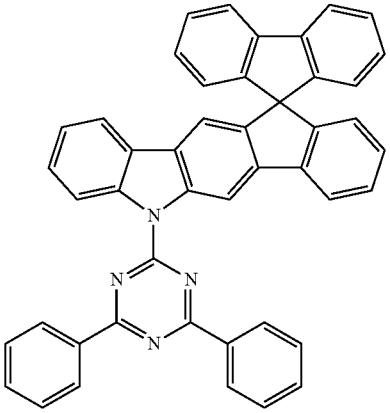 [SMILES: c1ccc(-c2nc(-c3ccccc3)nc(-n3c4ccccc4c4cc5c(cc43)-c3ccccc3C53c4ccccc4-c4ccccc43)n2)cc1] | 76% |

-continued
| Ex. | Starting material 1 | Product | Yield |
|---|---|---|---|
| 3h | 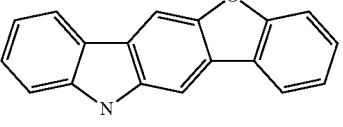 1199350-22-5 | 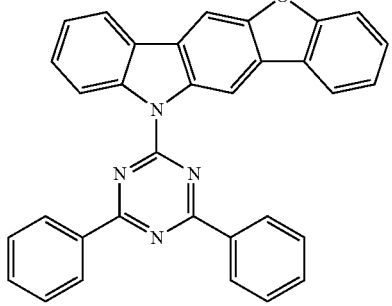 | 81% |
| 3i | 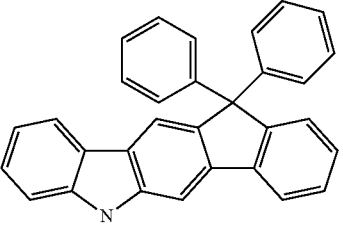 [SMILES: c1ccc(C2(c3ccccc3)c3ccccc3-c3cc4[nH]c5ccccc5c4cc32)cc1] 1190100-18-5 | 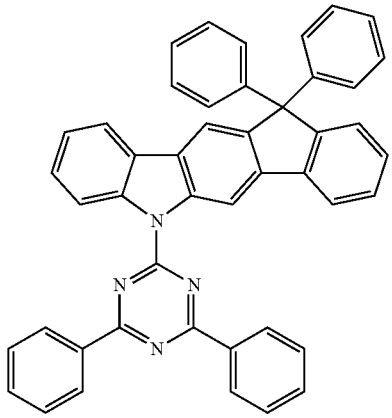 [SMILES: c1ccc(-c2nc(-c3ccccc3)nc(-n3c4ccccc4c4cc5c(cc43)-c3ccccc3C5(c3ccccc3)c3ccccc3)n2)cc1] | 85% |
| 3j | 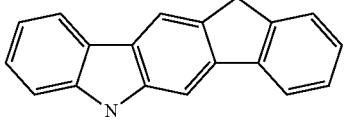 879689-95-9 | 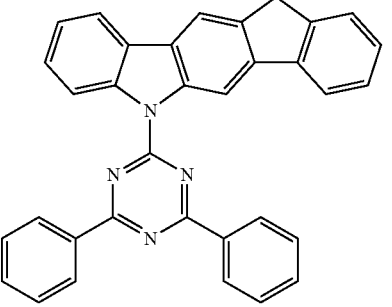 | 76% |

Example 4a 12,13-Bis-(4,6-diphenyl-1,3,5-triazin-2-yl)-12,13-dihydro-indolo[3,2-c]acridin-7-one

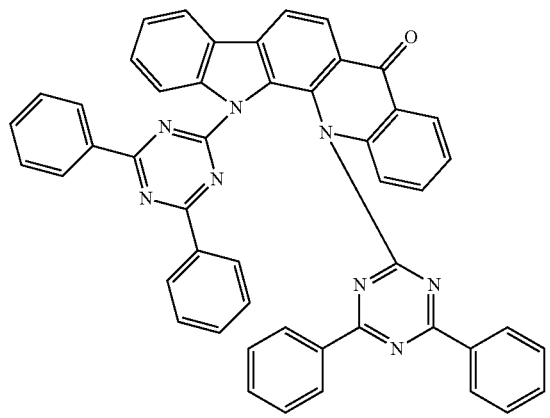 [SMILES: O=c1c2ccccc2n(-c2nc(-c3ccccc3)nc(-c3ccccc3)n2)c2c1ccc1c3ccccc3n(-c3nc(-c4ccccc4)nc(-c4ccccc4)n3)c12]

3 g (75 mmol) of NaH (60% in oil) are initially introduced in 150 ml of dichloromethane. A solution of 8.4 g (28 mmol) of 3-((Z)-propenyl)-2-vinyl-1H,11H-1,11-diazacyclopenta[a]anthracen-6-one in dichloromethane is added dropwise at RT. After 1 h, 17 g (62 mmol) of 2-chloro-4,6-diphenyl-1,3,5-triazine are added dropwise, and the mixture is stirred at room temperature for 8 h. The solid which has precipitated out is recrystallised from toluene. The crystals which have deposited are filtered off with suction, washed with a little MeOH and dried in vacuo; yield: 14.6 g; 70% of theory; purity: 99.9% according to HPLC.

The following compounds are obtained analogously:

| Ex. | Starting material 1 | Product | Yield |
|---|---|---|---|
| 4b | 259676-14-7 | | 69% |
| 4c | 897023-31-3 | | 66% |

Example 5a

6-(2,6-Diphenylpyridin-4-yl)-12,12-dimethyl-6,12-dihydro-6-azaindeno[1,2-b]fluorene a) 2,6-Dibromo-4-nitropyridine

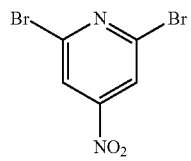

A solution of 50 g (211 mmol) of 2,6-dibromopyridine in 250 ml of trifluoroacetic acid is warmed to 90° C. 53 ml (515 mmol) of a 33% hydrogen peroxide solution are added dropwise. After 3 h, the reaction mixture is cooled and poured into 200 ml of ice-water. The filtrate is extracted three times with dichloromethane, and the combined organic phases are washed four times with a 0.5 M $K_2CO_3$ solution, dried over $Na_2SO_4$ and evaporated. The residue of 2,6-dibromopyridine 1-oxide (41.2 g) is employed further.

A solution of 20 g (78 mmol) of 2,6-dibromopyridine 1-oxide is warmed to 40° C. in 70 ml of $H_2SO_4$. Nitrating acid (70 ml of $H_2SO_4$ and 34 ml of fuming $HNO_3$) is added to the solution at this temperature. The reaction mixture is heated at 90° C. for 3 h. After cooling, the reaction mixture is poured into 800 ml of ice-water. The solid which has precipitated out is filtered off and washed with water. After drying, the 2,6-dibromo-4-nitropyridine 1-oxide (17.9 g) is suspended in 200 ml of chloroform, 6 ml of phosphorus tribromide (64 mmol) are added at room temperature, and the mixture is stirred for 1 h and then heated under reflux for 2 days. After cooling, the solution is poured into 500 ml of ice-water, and the mixture is neutralised using solid $NaHCO_3$. The aqueous phase is separated off and extracted a number of times with $CHCl_3$, and the combined organic phases are washed with a sodium thiosulfate solution and then with water, dried and evaporated. The residue is recrystallised from EtOH. Yield: 41.7 g (148 mmol), 70% of theory.

b) 6-(2,6-Diphenylpyridin-4-yl)-12,12-dimethyl-6,12-dihydro-6-azaindeno[1,2-b]fluorene

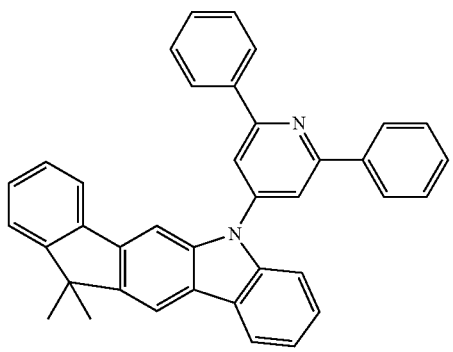 [SMILES: CC1(C)c2ccccc2-c2cc3c(cc21)c1ccccc1n3-c1cc(-c2ccccc2)nc(-c2ccccc2)c1]

20 g (70.7 mmol) of 12,12-dimethyl-6,12-dihydro-6-azaindeno[1,2-b]fluorene are dissolved in 50 ml of dimethylformamide under a protective-gas atmosphere, and 3.1 g of 60% NaH in mineral oil (78 mmol) are added. After 1 h at room temperature, a solution of 2,6-dibromo-4-nitropyridine (20 g, 70.7 mmol) in 20 ml of DMF is added dropwise. The reaction mixture is stirred at room temperature for 12 h. The reaction mixture is then poured onto ice and extracted three times with dichloromethane. The combined organic phases are dried over $Na_2SO_4$ and evaporated. The residue is recrystallised from toluene. Yield: 29.6 g (80 mmol), 95% of theory.

25 g (48 mmol) of 6-(2,6-dibromopyridin-4-yl)-12,12-dimethyl-6,12-dihydro-6-azaindeno[1,2-b]fluorene and 12.9 g of phenylboronic acid (106 mmol) are suspended in 300 ml of ethylene glycol dimethyl ether. 75 ml of a 2 M $Na_2CO_3$ solution are added to the reaction mixture. 2.8 g (2.4 mmol) of $Pd(PPh_3)_4$ are added to this suspension. The reaction mixture is heated under reflux for 12 h. After cooling, the solid which has precipitated out is filtered off with suction, washed with water and ethanol and dried. The residue is extracted with hot toluene, recrystallised from toluene and finally sublimed in a high vacuum, the purity is 99.9%. Yield: 18 g, 72% of theory.

The following compounds are obtained analogously:

| Ex. | Starting material 1 | Product | Yield |
|---|---|---|---|
| 5b | ![structure] 1199350-22-5 | ![structure] | 81% |

| Ex. | Starting material 1 | Product | Yield |
|---|---|---|---|
| 5c | 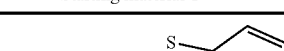 222-21-9 |  | 75% |

Example 6a

6-(3,5-Dipyrimidin-2-ylphenyl)-12,12-dimethyl-6, 12-dihydro-6-azaindeno[1,2-b]fluorene a) 5-Iodo-1,3-(2'-pyrimidyl)benzene

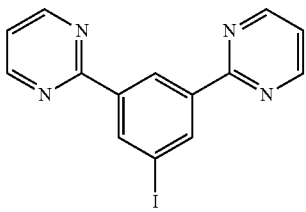 [SMILES: Ic1cc(-c2ncccn2)cc(-c2ncccn2)c1]

40 g (127 mmol) of tribromobenzene are dissolved in 800 ml of Et$_2$O and cooled to −78° C. 88 ml (140 mmol) of n-BuLi (1.6 M solution in hexane) are added dropwise to this solution. After the solution has been stirred at this temperature for 3 h, 19.4 ml of chlorotrimethylsilane are added dropwise, and the reaction mixture is stirred at room temperature for a further 1 h. The mixture is subsequently partitioned between heptane and water, and the aqueous phase is extracted three times with heptane, dried over Na$_2$SO$_4$ and evaporated in a rotary evaporator. The residue which remains, 31.4 g (80% yield), is distilled and reacted further.

25 g (79.4 mmol) of 5-trimethylsilyl-1,3-bromobenzene, 37.7 g (159 mmol) of bis(pinacolato)diborane and 4 g of potassium acetate (350 mmol) are suspended in 700 ml of DMSO. 11.9 g (16 mmol) of 1,1-bis(diphenyl-phosphino) ferrocenepalladium(II) dichloride complex with dichloromethane are added to this suspension. The reaction mixture is heated under reflux for 16 h. After cooling, the organic phase is separated off, washed three times with 200 ml of water and subsequently evaporated to dryness. The residue is recrystallised from toluene. Yield: 24 g, 75% of theory.

20 g (49.7 mmol) of 5-trimethylsilylbenzene-1,3-bis(boronic acid pinacol ester) and 15.8 g of 2-bromopyrimidine (99.5 mmol) are suspended in 600 ml of ethylene glycol dimethyl ether. 100 ml of a 2 M Na$_2$CO$_3$ solution are added to the reaction mixture. 1.5 g (4.9 mmol) of Pd(PPh$_3$)$_4$ are added to this suspension. The reaction mixture is heated under reflux for 12 h. After cooling, the solid which has precipitated out is filtered off with suction, washed with water and ethanol and dried. The residue is recrystallised from toluene. Yield: 9.5 g, 60% of theory.

15 g (49 mmol) of 5-trimethylsilyl-1,3-(2'-pyrimidyl)benzene are dissolved in 200 ml of dichloromethane under a protective-gas atmosphere, and 8.1 g of I-Cl (50 mol) are added at 0° C. The reaction mixture is stirred at this temperature for 12 h. After this time, the reaction mixture is poured into water and extracted three times with dichloromethane. The combined organic phases are washed with a sodium dithionite solution, dried over Na$_2$SO$_4$ and evaporated. The residue is recrystallised from heptane/ethyl acetate. Yield: 12.6 g (80 mmol), 60% of theory.

b) 6-(3,5-Dipyrimidin-2-ylphenyl)-12,12-dimethyl-6, 12-dihydro-6-azaindeno[1,2-b]fluorene

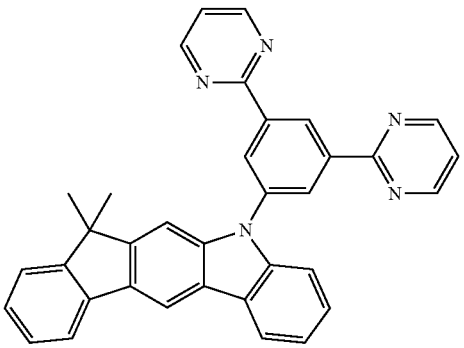 [SMILES: CC1(C)c2ccccc2-c2cc3c4ccccc4n(-c4cc(-c5ncccn5)cc(-c5ncccn5)c4)c3cc21]

10.9 g (38.32 mmol) of 12,12-dimethyl-6,12-dihydro-6-azaindeno[1,2-b]-fluorene, 12 g (38.32 mmol) of 5-iodo-1,3-(2'-pyrimidyl)benzene and 16 g of K$_2$CO$_3$ are suspended in 300 ml of p-xylene. 0.86 g (3.84 mmol) of Pd(OAc)$_2$ and 7.6 ml of a 1 M tri-tert-butylphosphine solution are added to this suspension. The reaction mixture is heated under reflux for 16 h. After cooling, the organic phase is separated off, washed three times with 200 ml of water and subsequently evaporated to dryness. The residue is extracted with hot toluene, recrystallised from toluene and finally sublimed in a high vacuum, the purity is 99.9%. Yield: 16.4 g (26.6 mmol), 96% of theory.

The following compounds are obtained analogously:

| Ex. | Starting material 1 | Product | Yield |
|---|---|---|---|
| 6b | 1199350-22-5 | | 86% |
| 6c | 222-21-9 | | 76% |

Example 7a 6-(4,6-Diphenylpyrimidin-2-yl)-12,12-dimethyl-6,12-dihydro-6-azaindeno[1,2-b]fluorene a) 2-Chloro-4,6-diphenylpyrimidine

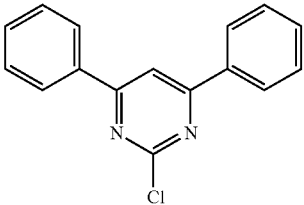 [SMILES: Clc1nc(-c2ccccc2)cc(-c2ccccc2)n1]

75 g (0.41 mmol) of 1,3,5-trichloropyrimidine, 100 g (0.82 mol) of phenylboronic acid and 625 ml of 4 M NaHCO$_3$ solution are suspended in 2.5 l of ethylene glycol dimethyl ether. 2.3 g (10.23 mmol) of Pd(OAc)$_2$ and 10.35 g (34 mmol) of (o-Tol)$_3$P are added to this suspension, and the reaction mixture is heated under reflux for 16 h. The mixture is subsequently partitioned between ethyl acetate and water, and the organic phase is washed three times with water and dried over Na$_2$SO$_4$ and evaporated in a rotary evaporator. The residue which remains is recrystallised from heptane/toluene. The yield is 43 g (0.15 mol, 38%).

b) 6-(4,6-Diphenylpyrimidin-2-yl)-12,12-dimethyl-6,12-dihydro-6-azaindeno[1,2-b]fluorene

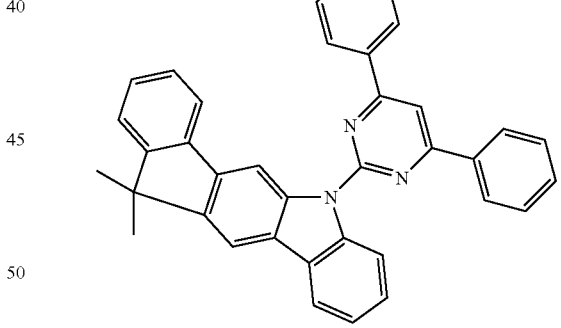

4.2 g of 60% NaH in mineral oil (0.106 mol) are dissolved in 300 ml of dimethylformamide under a protective-gas atmosphere. 30 g of 12,12-dimethyl-6,12-dihydro-6-azaindeno[1,2-b]fluorene (0.106 mol) are dissolved in 250 ml of DMF and added dropwise to the reaction mixture. After 1 hour at room temperature, a solution of 2-chloro-4,6-diphenyl-1,3-pyrimidine (34.5 g, 0.122 mol) in 200 ml of THF is added dropwise. The reaction mixture is then stirred at room temperature for 12 h. After this time, the reaction mixture is poured onto ice and extracted three times with dichloromethane. The combined organic phases are dried over Na$_2$SO$_4$ and evaporated. The residue is extracted with hot toluene, recrystallised from toluene/n-heptane and finally sublimed in a high vacuum, the purity is 99.9%. The yield is 27 g (51%).

The following compounds are obtained analogously:

| Ex. | Starting material 1 | Product | Yield |
|---|---|---|---|
| 7b | 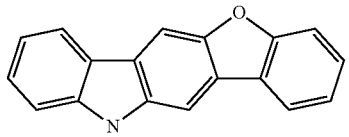 [SMILES: c1ccc2c(c1)[nH]c1cc3c(cc12)oc1ccccc13] 1199350-22-5 | 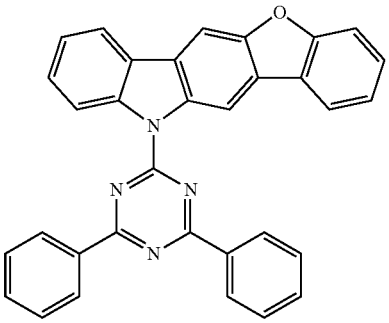 [SMILES: c1ccc(-c2nc(-c3ccccc3)nc(-n3c4ccccc4c4cc5oc6ccccc6c5cc43)n2)cc1] | 55% |
| 7c | 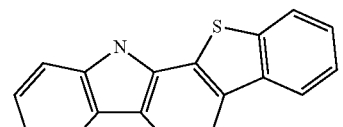 222-21-9 | 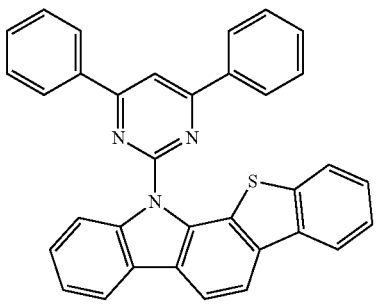 [SMILES: c1ccc(-c2cc(-c3ccccc3)nc(-n3c4ccccc4c4ccc5c6ccccc6sc5c43)n2)cc1] | 59% |

Device Examples

Production of OLEDs (Examples 1 to 31 and Comparative Examples 1 to 7)

OLEDs according to the invention and OLEDs in accordance with the prior art are produced by a general process as described in WO 2004/058911, which is adapted to the circumstances described here (layer-thickness variation, materials used).

The data for various OLEDs are presented in the following Comparative Examples 1 to 7 and Examples 1 to 31 (see Tables 1 and 2). Glass plates coated with structured ITO (indium tin oxide) in a thickness of 150 nm are coated with 20 nm of PEDOT (spin-coated from water; purchased from H. C. Starck, Goslar, Germany; poly(3,4-ethylenedioxy-2,5-thiophene)) for improved processing. These coated glass plates are the substrates to which the OLEDs are applied. The OLEDs have in principle the following layer structure: substrate/optional hole-injection layer (HIL1) 5 nm/hole-transport layer (HTM1)/electron-blocking layer (EBL) 20 nm/emission layer (EML)/optional hole-blocking layer (HBL) 10 nm/electron-transport layer (ETM) and finally a cathode. The cathode is formed by an aluminium layer with a thickness of 100 nm, where an electron-injection layer comprising LiF with a thickness of 1 nm is introduced between the cathode and the electron-transport layer, depending on the electron-transport material used. The precise structure of the OLEDs is explained in connection with the examples indicated below. The materials used for the production of the OLEDs are shown in Table 3.

All materials are applied by thermal vapour deposition in a vacuum chamber. The emission layer here always consists of at least one matrix material (host) and a dopant, with which the host material or materials is/are admixed by co-evaporation. Information such as H2:TER1 (85%:15%) here means that the material H2 is present in the layer in a volume proportion of 85% and TER1 is present in the layer in a proportion of 15%. The electron-transport layer may analogously also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminance, calculated from current-voltage-luminance characteristic lines (IUL characteristic lines), and the lifetime are determined. The lifetime is defined as the time after which the luminance has dropped to half from a certain initial luminance. This value can be converted to data for other initial luminances with the aid of conversion formulae known to the person skilled in the art. The lifetime for an initial luminance of 1000 cd/m$^2$ is the usual value quoted in this case.

Some of the examples are explained in greater detail below in order to illustrate the advantages of the compounds according to the invention. However, it should be pointed out that this only represents a selection of the data shown. As can be seen from the tables, significant improvements over the prior art are also achieved on use of the compounds according to the invention that are not described in greater detail, in some cases in all parameters, in some cases only an improvement in the efficiency or voltage or lifetime is observable. However, an improvement in just one of the parameters mentioned represents a significant advance, since various applications require optimisation with respect to different parameters.

Use of Compounds According to the Invention as Electron-Transport Materials

Table 1 shows data for some OLEDs which exhibit the advantages on use of compounds according to the invention in the electron-transport layer. The OLEDs consist of the layer sequence substrate/hole-injection layer (HIL1) 5 nm/hole-transport layer (HTM1) 140 nm/NPB 20 nm/emission layer 30 nm/electron-transport layer (ETM) 20 nm/optionally 1 nm of LiF/aluminium 100 nm. The emission layer here consists of the host material H1, which is doped with the blue-emitting dopant D1 in a volume proportion of 5%. In Comparative Example 2 and Examples 2 and 4, the electron-transport layer employed is a mixed layer comprising an electron-transport material and LiQ produced by co-evaporation. The volume proportion of LiQ here is 60%.

The OLEDs corresponding to Comparative Examples 1 and 2 and Examples 1 to 4 exhibit comparable CIE colour coordinates and a comparable lifetime of about 150 h at an initial luminance of 6000 cd/m$^2$. This corresponds to about 5500 h at an initial luminance of 1000 cd/m$^2$ based on the extrapolation formulae known to the person skilled in the art.

The use of materials ETM2 and ETM3 according to the invention results in a significant improvement both in the external quantum efficiency (EQE), the current efficiency (in cd/A), but in particular also the operating voltage and thus the power efficiency (in lm/W). The increase in the power efficiency in particular is important with respect to mobile applications. Here, an increase of only 10% should be regarded as a significant improvement.

The greatest improvement in the power efficiency is achieved with LiF as electron-injection layer. The use of compounds ETM2 and ETM3 according to the invention increases the power efficiency here by about 40% compared with the use of Alq$_3$ (comparison of Comparative Example 1 with Examples 1 and 3). A significant improvement by about 15% can also be achieved through the use of ETM2 or E™3 on use of a mixed electron-transport layer which already gives rise to good power efficiency with electron-transport material ETM1 in accordance with the prior art (Comparative Example 2) (comparison of Comparative Example 2 with Examples 2 and 4).

Furthermore, compound ETM3 according to the invention exhibits significantly improved processability compared with the prior art ETM1. Layers of the materials with a thickness of about 1 μm are deposited under the same vapour-deposition conditions (vapour-deposition rate of 0.1 nm/s). Material ETM3 according to the invention exhibits no clogging of the vapour-deposition source. By contrast, a layer of the material grows inwardly in an annular manner at the upper edge of the vapour-deposition source on use of ETM1. This means that controlled layer deposition is no longer possible after a vapour-deposition time of about 1.5 h. The compounds according to the invention are thus significantly more suitable for use in mass production than compound ETM1 in accordance with the prior art.

Use of Compounds According to the Invention as Host Materials for Phosphorescent Dopants The compounds according to the invention can also be employed as host materials for phosphorescent dopants. Besides compound H5, materials ETM2 and ETM3 described in the previous section, which are referred to below as H3 and H4 for clarity, are used here. Compound H2 is used as comparison in accordance with the prior art. OLEDs comprising the green-emitting dopant TEG1 and the red-emitting dopants TER1 and TER2 are compared.

The OLEDs have the structure substrate/hole-transport layer (HTM1)/electron-blocking layer (EBL) 20 nm/emission layer (EML)/optional hole-blocking layer (HBL) 10 nm/electron-transport layer (ETM)/optionally LiF 1 nm/aluminium 100 nm. In the OLEDs of Comparative Examples 3-5 and Examples 5-7 and 13, 14 and 25, the thickness of the hole-transport layer is 20 nm, the electron-blocking layer is formed by NPB, the electron-transport layer is an Alq$_3$ layer with a thickness of 20 nm with an electron-injection layer comprising LiF with a thickness of 1 nm. The OLEDs of Comparative Example 5 and Example 7 additionally comprise a hole-blocking layer of material H2 with a thickness of 10 nm between the emission layer and the electron-transport layer.

The OLEDs of Comparative Examples 6 and 7 and Examples 8-12, 15-24 and 26-31 comprise a hole-transport layer with a thickness of 160 nm and an electron-blocking layer which is formed by material EBM1. As electron-transport layer, these OLEDs comprise a mixture of ETM1 and LiQ in the volume ratio 50%:50%, an electron-injection layer is not present. In the OLEDs of Comparative Examples 6, 11, 13, 24 and 32, a hole-blocking layer comprising material H2 with a thickness of 10 nm is present; the thickness of the electron-transport layer is 30 nm. The hole-blocking layer is not present in the OLEDs of Comparative Example 7 and Examples 9, 11, 12, 15-20, 22-24, 26-28, 30 and 31; the thickness of the electron-transport layer here is 40 nm.

The use of compounds H3, H4 and H5 according to the invention gives rise to significant improvements with respect to efficiency, operating voltage and lifetime compared with the use of H2 in accordance with the prior art (see Table 2).

In red-emitting OLEDs, a 25-50% increase in the power efficiency is obtained on use of host material H5, depending on whether dopant TER1 or TER2 is used and whether a further host material is present (comparison of Comparative Examples 3 to 5 with Examples 5 to 7). Furthermore, the lifetime increases by 20-35% on use of H5 compared with

TABLE 1

Use of compounds according to the invention as electron-transport materials

|  | ETM | EIM | Voltage for 1000 cd/m$^2$ | Efficiency at 1000 cd/m$^2$ | Efficiency at 1000 cd/m$^2$ | EQE at 1000 cd/m$^2$ | CIE x/y at 1000 cd/m$^2$ |
|---|---|---|---|---|---|---|---|
| Comparative Example 1 | Alq$_3$ | LiF 1 nm | 6.4 V | 5.1 cd/A | 2.5 lm/W | 4.2% | 0.142/0.151 |
| Comparative Example 2 | ETM1: LiQ | — | 4.7 V | 8.1 cd/A | 5.4 lm/W | 6.3% | 0.142/0.155 |
| Example 1 | ETM2 | LiF 1 nm | 5.8 V | 6.2 cd/A | 3.4 lm/W | 4.9% | 0.141/0.154 |
| Example 2 | ETM2: LiQ | — | 4.5 V | 8.8 cd/A | 6.1 lm/W | 6.9% | 0.142/0.156 |
| Example 3 | ETM3 | LiF 1 nm | 5.6 V | 6.4 cd/A | 3.6 lm/W | 5.0% | 0.141/0.152 |
| Example 4 | ETM3: LiQ | — | 4.5 V | 9 cd/A | 6.3 lm/W | 7.1% | 0.143/0.157 | components in which material H2 in accordance with the prior art is employed. The compounds according to the invention thus give rise to significant improvements in all relevant parameters on use as host material in red-emitting phosphorescent OLEDs.

The use of materials H3 and H4 according to the invention in green-phosphorescent OLEDs even enables the efficiency, operating voltage and lifetime to be improved to a greater extent than in the red-emitting OLEDs just described. The use of H4 as host material gives rise to an improvement by 35-40% in the power efficiency and an increase by about 30-40% in the lifetime compared with the use of H2 (comparison of Comparative Example 6 with Example 10, or Comparative Example 7 with Example 11 respectively). The very large increase in the power efficiency arises, in particular, due to the significant reduction in the operating voltage by about 1 V. Compared with the prior art H2, a significant improvement in the power efficiency by about 20% and an increase in the lifetime by 20-30% likewise arise on use of compound H3 according to the invention (comparison of Comparative Example 6 with Example 8, or Comparative Example 7 with Example 9 respectively).

TABLE 2

Use of compounds according to the invention as host materials in phosphorescent OLEDs

| | EML | HBL | Voltage for 1000 cd/m² | Efficiency at 1000 cd/m² | Efficiency at 1000 cd/m² | CIE x/y at 1000 cd/m² | Lifetime from 1000 cd/m² |
|---|---|---|---|---|---|---|---|
| Comparative Example 3 | H2:TER1 (85%:15%) | — | 5.0 V | 7.2 cd/A | 4.5 lm/W | 0.69/0.31 | 14000 |
| Comparative Example 4 | H2:TER2 (85%:15%) | — | 6.5 V | 9.0 cd/A | 4.3 lm/W | 0.66/0.33 | 18000 |
| Comparative Example 5 | H2:CBP:TER1 (45%:45%:10%) | H2 | 5.2 V | 8.1 cd/A | 4.9 lm/W | 0.68/0.32 | 15000 |
| Comparative Example 6 | H2:TEG1 (90%:10%) | H2 | 4.7 V | 55 cd/A | 37 lm/W | 0.36/0.61 | 27000 |
| Comparative Example 7 | H2:TEG1 (90%:10%) | — | 4.6 V | 54 cd/A | 37 lm/W | 0.37/0.60 | 24000 |
| Example 5 | H5:TER1 (85%:15%) | — | 4.4 V | 8.1 cd/A | 5.8 lm/W | 0.69/0.31 | 17000 |
| Example 6 | H5:TER2 (85%:15%) | — | 4.7 V | 9.9 cd/A | 6.6 lm/W | 0.65/0.32 | 23000 |
| Example 7 | H5:CBP:TER1 (45%:45%:10%) | H2 | 4.6 V | 8.9 cd/A | 6.1 lm/W | 0.69/0.31 | 20000 |
| Example 8 | H3:TEG1 (90%:10%) | H2 | 3.9 V | 54 cd/A | 44 lm/W | 0.37/0.60 | 35000 |
| Example 9 | H3:TEG1 (90%:10%) | — | 3.8 V | 53 cd/A | 44 lm/W | 0.37/0.60 | 29000 |
| Example 10 | H4:TEG1 (90%:10%) | H2 | 3.8 V | 60 cd/A | 50 lm/W | 0.37/0.61 | 37000 |
| Example 11 | H4:TEG1 (90%:10%) | — | 3.6 V | 58 cd/A | 51 lm/W | 0.38/0.60 | 32000 |
| Example 12 | H6:TEG1 (90%:10%) | — | 3.7 V | 51 cd/A | 43 lm/W | 0.38/0.60 | 26000 |
| Example 13 | H7:TER1 (85%:15%) | — | 3.9 V | 7.1 cd/A | 5.7 lm/W | 0.69/0.31 | 21000 |
| Example 14 | H8:TER1 (85%:15%) | — | 4.3 V | 7.7 cd/A | 5.6 lm/W | 0.69/0.31 | 19000 |
| Example 15 | H9:TEG1 (90%:10%) | — | 3.6 V | 56 cd/A | 49 lm/W | 0.38/0.60 | 39000 |
| Example 16 | H10:TEG1 (90%:10%) | — | 3.4 V | 53 cd/A | 49 lm/W | 0.37/0.59 | 25000 |
| Example 17 | H11:TEG1 (90%:10%) | — | 4.0 V | 53 cd/A | 41 lm/W | 0.38/0.60 | 27000 |
| Example 18 | H12:TEG1 (90%:10%) | — | 3.9 V | 49 cd/A | 40 lm/W | 0.37/0.60 | 28000 |
| Example 19 | H13:TEG1 (90%:10%) | — | 3.9 V | 54 cd/A | 43 lm/W | 0.36/0.60 | 35000 |
| Example 20 | H14:TEG1 (90%:10%) | — | 4.1 V | 61 cd/A | 47 lm/W | 0.36/0.61 | 39000 |
| Example 21 | H14:TEG1 (90%:10%) | H2 | 4.1 V | 63 cd/A | 48 lm/W | 0.36/0.61 | 42000 |
| Example 22 | H15:TEG1 (90%:10%) | — | 4.2 V | 51 cd/A | 39 lm/W | 0.36/0.60 | 31000 |
| Example 23 | H16:TEG1 (90%:10%) | — | 4.0 V | 50 cd/A | 39 lm/W | 0.36/0.60 | 30000 |
| Example 24 | H17:TEG1 (90%:10%) | — | 3.5 V | 58 cd/A | 52 lm/W | 0.36/0.60 | 38000 |
| Example 25 | H17:TER1 (85%:15%) | — | 4.1 V | 7.8 cd/A | 6.1 lm/W | 0.69/0.31 | 25000 |
| Example 26 | H18:TEG1 (90%:10%) | — | 3.7 V | 53 cd/A | 45 lm/W | 0.36/0.60 | 32000 |
| Example 27 | H19:TEG1 (90%:10%) | — | 3.6 V | 48 cd/A | 42 lm/W | 0.36/0.60 | 28000 |
| Example 28 | H20:TEG1 (90%:10%) | — | 3.7 V | 52 cd/A | 44 lm/W | 0.37/0.60 | 30000 |
| Example 29 | H20:TEG1 (90%:10%) | H2 | 3.8 V | 52 cd/A | 44 lm/W | 0.37/0.60 | 35000 |

TABLE 2-continued

Use of compounds according to the invention as host materials in phosphorescent OLEDs

| | EML | HBL | Voltage for 1000 cd/m² | Efficiency at 1000 cd/m² | Efficiency at 1000 cd/m² | CIE x/y at 1000 cd/m² | Lifetime from 1000 cd/m² |
|---|---|---|---|---|---|---|---|
| Example 30 | H21:TEG1 (90%:10%) | — | 3.8 V | 48 cd/A | 40 lm/W | 0.36/0.60 | 27000 |
| Example 31 | H22:TEG1 (90%:10%) | — | 3.7 V | 49 cd/A | 42 lm/W | 0.36/0.60 | 28000 |

TABLE 3

Structures of the materials used

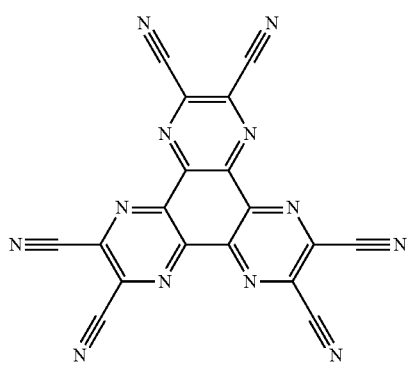 [SMILES: N#Cc1nc2c3nc(C#N)c(C#N)nc3c3nc(C#N)c(C#N)nc3c2nc1C#N]

HIL1

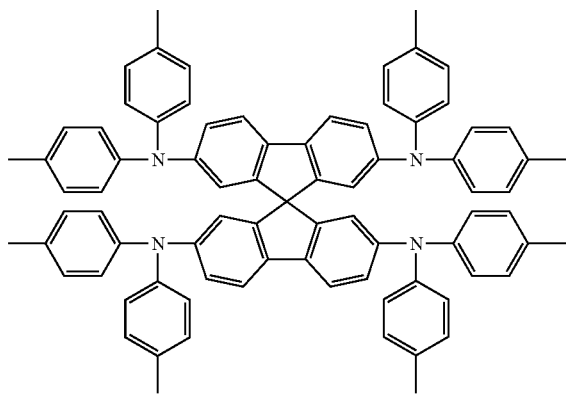

HTM1

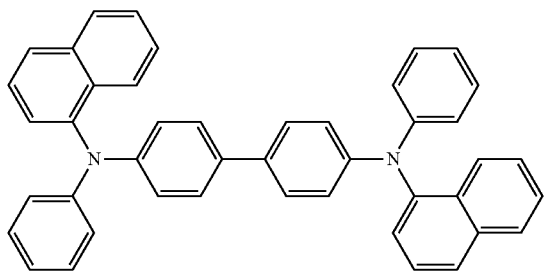 [SMILES: c1ccc(N(c2ccc(-c3ccc(N(c4ccccc4)c4cccc5ccccc45)cc3)cc2)c2cccc3ccccc23)cc1]

NPB

TABLE 3-continued

Structures of the materials used

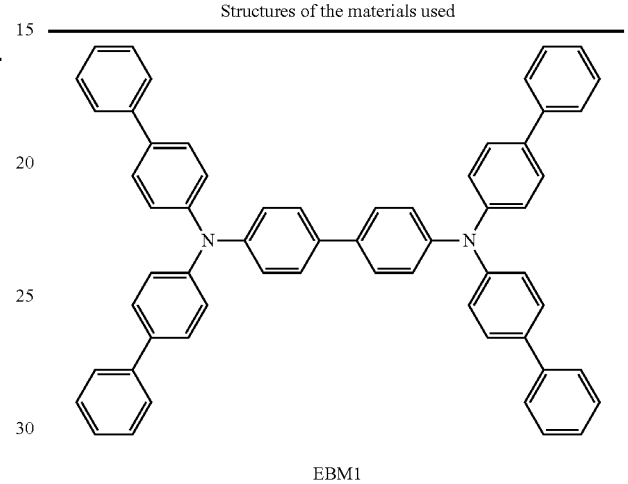

EBM1

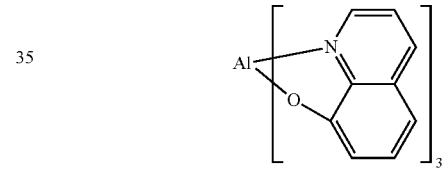

Alq₃

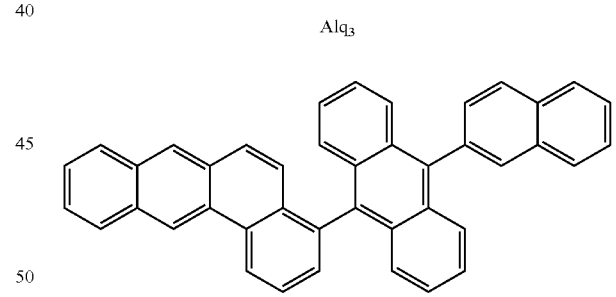

H1

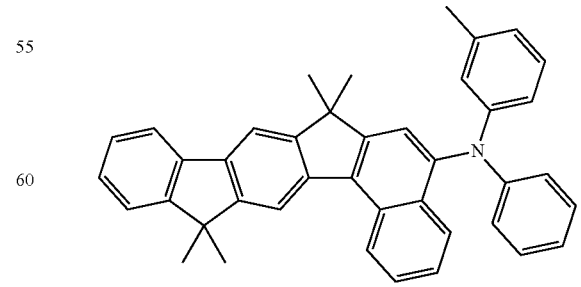

D1

TABLE 3-continued
Structures of the materials used
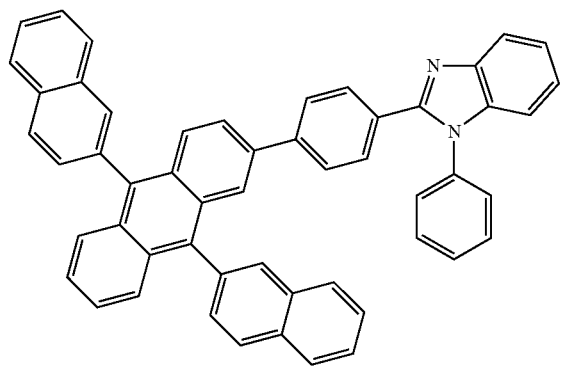 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1]
ETM1
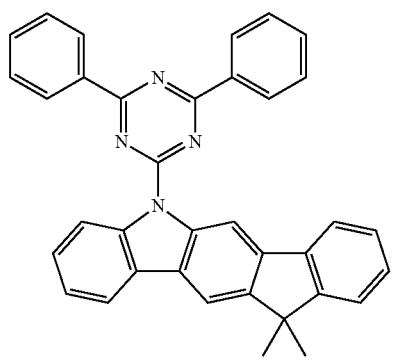 [SMILES: CC1(C)c2ccccc2-c2cc3c(cc21)c1ccccc1n3-c1nc(-c2ccccc2)nc(-c2ccccc2)n1]
ETM2 = H3
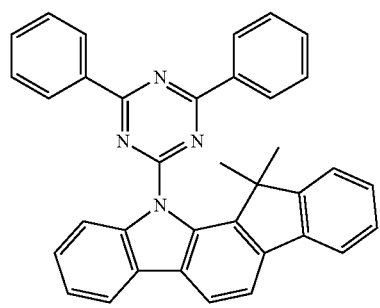 [SMILES: CC1(C)c2ccccc2-c2ccc3c4ccccc4n(-c4nc(-c5ccccc5)nc(-c5ccccc5)n4)c3c21]
ETM3 = H4
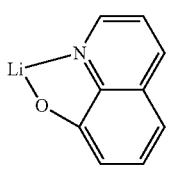
LiQ
TABLE 3-continued
Structures of the materials used
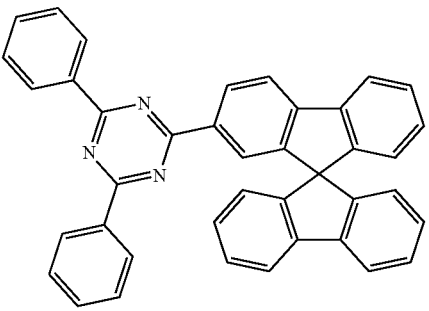 [SMILES: c1ccc(-c2nc(-c3ccccc3)nc(-c3ccc4c(c3)C3(c5ccccc5-c5ccccc53)c3ccccc3-4)n2)cc1]
H2
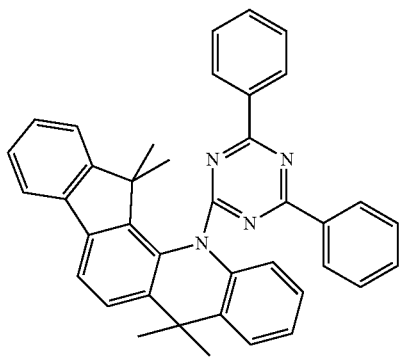 [SMILES: CC1(C)c2ccccc2N(c2nc(-c3ccccc3)nc(-c3ccccc3)n2)c2c1ccc1c2C(C)(C)c2ccccc2-1]
H5
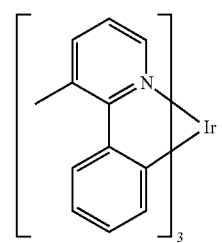
TEG1
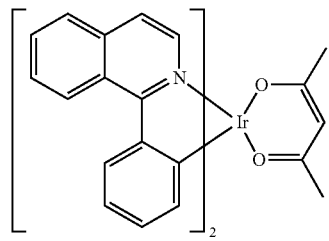
TER1

TABLE 3-continued
Structures of the materials used
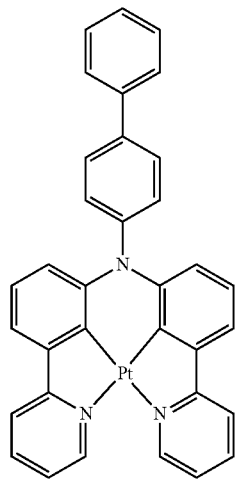
TER2
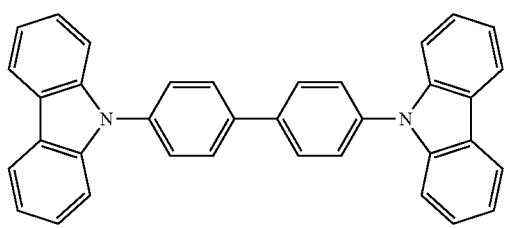 [SMILES: c1ccc2c(c1)c1ccccc1n2-c1ccc(-c2ccc(-n3c4ccccc4c4ccccc43)cc2)cc1]
CBP
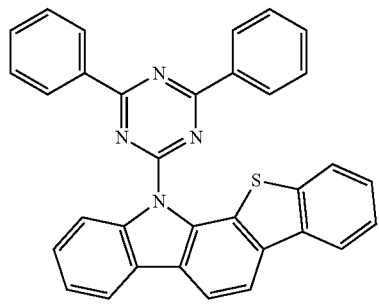
H6
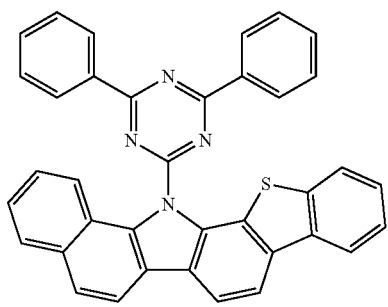 [SMILES: c1ccc(-c2nc(-c3ccccc3)nc(-n3c4c5ccccc5ccc4c4ccc5c6ccccc6sc5c43)n2)cc1]
H7
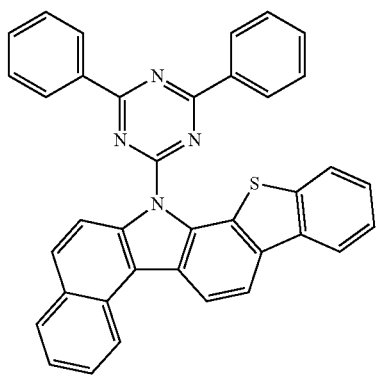 [SMILES: c1ccc(-c2nc(-c3ccccc3)nc(-n3c4ccc5ccccc5c4c4ccc5c6ccccc6sc5c43)n2)cc1]
H8
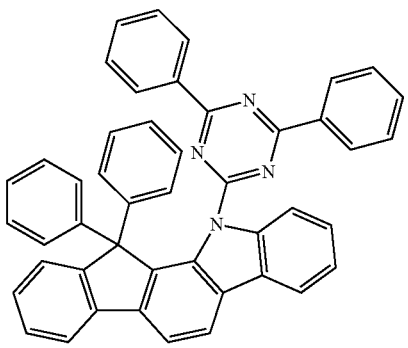 [SMILES: c1ccc(-c2nc(-c3ccccc3)nc(-n3c4ccccc4c4ccc5c(c43)C(c3ccccc3)(c3ccccc3)c3ccccc3-5)n2)cc1]
H9
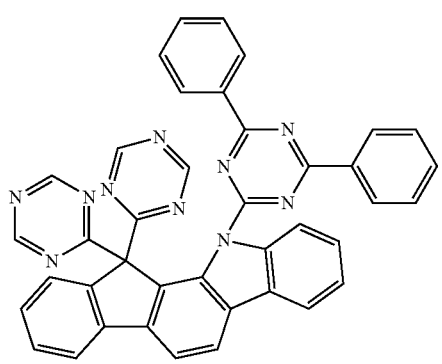 [SMILES: c1ccc(-c2nc(-c3ccccc3)nc(-n3c4ccccc4c4ccc5c(c43)C(c3ncncn3)(c3ncncn3)c3ccccc3-5)n2)cc1]
H10

TABLE 3-continued
Structures of the materials used
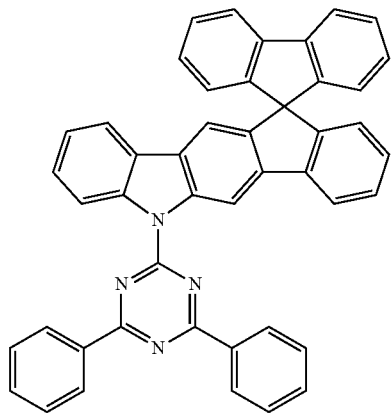 [SMILES: c1ccc(-c2nc(-c3ccccc3)nc(-n3c4ccccc4c4cc5c(cc43)-c3ccccc3C53c4ccccc4-c4ccccc43)n2)cc1]
H11
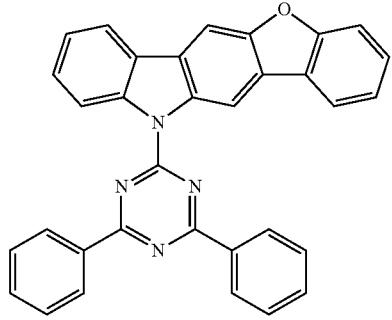 [SMILES: c1ccc(-c2nc(-c3ccccc3)nc(-n3c4ccccc4c4cc5oc6ccccc6c5cc43)n2)cc1]
H12
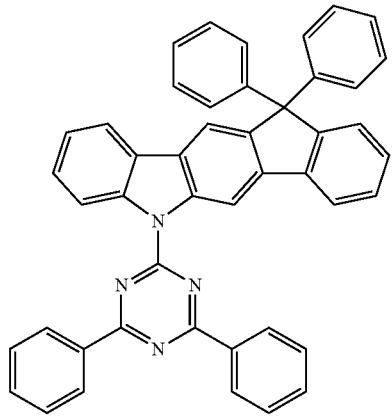 [SMILES: c1ccc(-c2nc(-c3ccccc3)nc(-n3c4ccccc4c4cc5c(cc43)-c3ccccc3C5(c3ccccc3)c3ccccc3)n2)cc1]
H13
TABLE 3-continued
Structures of the materials used
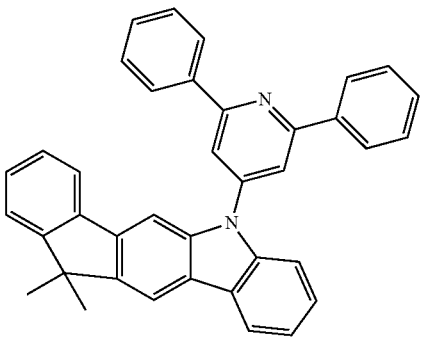 [SMILES: CC1(C)c2ccccc2-c2cc3c(cc21)c1ccccc1n3-c1cc(-c2ccccc2)nc(-c2ccccc2)c1]
H14
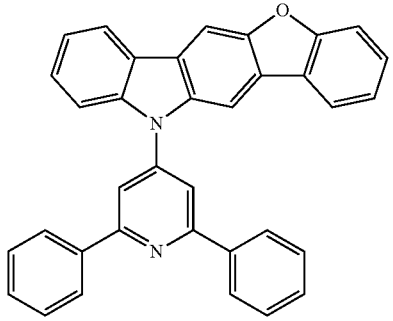 [SMILES: c1ccc(-c2cc(-n3c4ccccc4c4cc5oc6ccccc6c5cc43)cc(-c3ccccc3)n2)cc1]
H15
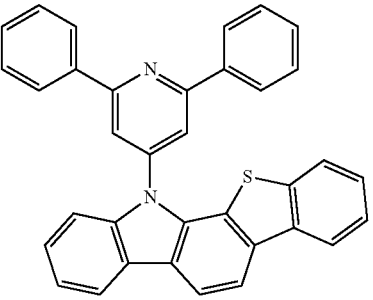 [SMILES: c1ccc(-c2cc(-n3c4ccccc4c4ccc5c6ccccc6sc5c43)cc(-c3ccccc3)n2)cc1]
H16
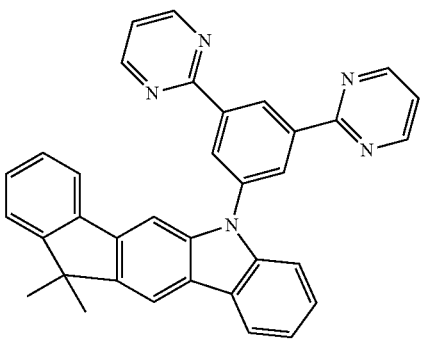 [SMILES: CC1(C)c2ccccc2-c2cc3c(cc21)c1ccccc1n3-c1cc(-c2ncccn2)cc(-c2ncccn2)c1]
H17

TABLE 3-continued

Structures of the materials used

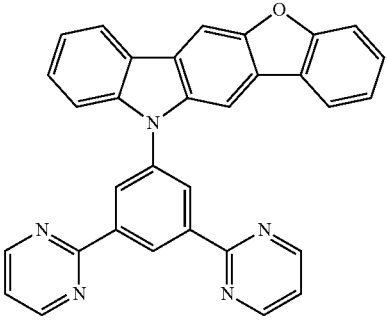 [SMILES: c1cnc(-c2cc(-c3ncccn3)cc(-n3c4ccccc4c4cc5oc6ccccc6c5cc43)c2)nc1]

H18

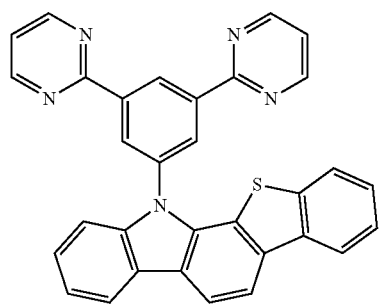 [SMILES: c1cnc(-c2cc(-c3ncccn3)cc(-n3c4ccccc4c4ccc5c6ccccc6sc5c43)c2)nc1]

H19

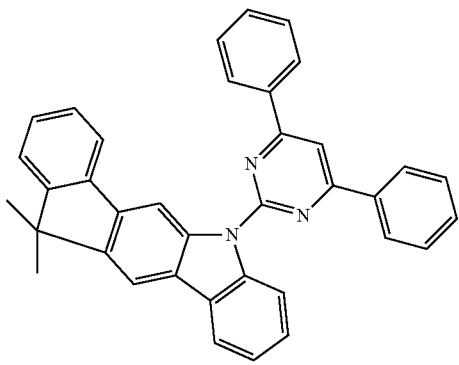 [SMILES: CC1(C)c2ccccc2-c2cc3c(cc21)c1ccccc1n3-c1nc(-c2ccccc2)cc(-c2ccccc2)n1]

H20

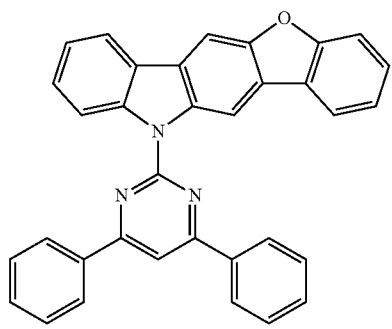 [SMILES: c1ccc(-c2cc(-c3ccccc3)nc(-n3c4ccccc4c4cc5oc6ccccc6c5cc43)n2)cc1]

H21

TABLE 3-continued

Structures of the materials used

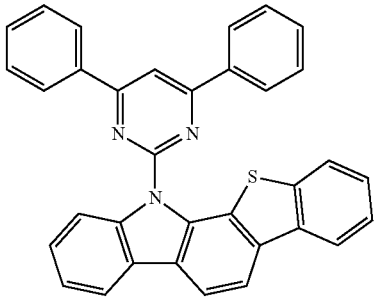

H22

The invention claimed is:
1. A compound of formula (I):

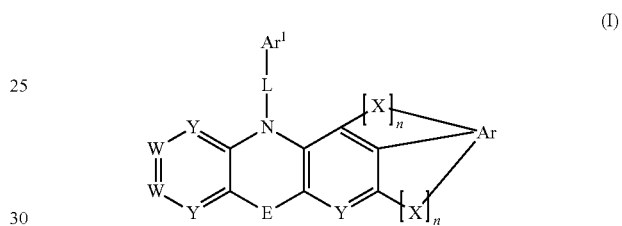

(I)

wherein

W is, identically or differently on each occurrence, N or $CR^1$;

Y is, identically or differently on each occurrence, N or $CR^2$;

E is either a single covalent bond or a divalent unit selected from the group consisting of $N(R^3)$, $C(R^3)_2$, $Si(R^3)_2$, C=O, C=NR$^3$, C=C(R$^3$)$_2$, S, S=O, SO$_2$, P(R$^3$) and P(=O)R$^3$;

X is, identically or differently on each occurrence, a divalent unit selected from the group consisting of $C(R^3)_2$, $N(R^3)$, $Si(R^3)_2$, C=O, C=NR$^3$, C=C(R$^3$)$_2$, S, O, S=O, SO$_2$, P(R$^3$) and P(=O)R$^3$, with the proviso that, if E is a single covalent bond, X is a divalent unit selected from the group consisting of $C(R^3)_2$, $Si(R^3)_2$, C=O, C=NR$^3$, C=C(R$^3$)$_2$, S, O, S=O, SO$_2$, P(R$^3$) and P(=O)R$^3$;

n and m
are, independently of one another, 0 or 1, with the proviso that the sum of n and m is equal to 1 or 2;

Ar is a divalent or trivalent, mono- or polycyclic aromatic or heteroaromatic unit having 5 to 40 aromatic ring atoms optionally substituted by one or more radicals $R^{4a}$;

Ar$^1$ is a mono- or polycyclic heteroaromatic group having 5 to 40 aromatic ring atoms optionally substituted by one or more radicals $R^{4b}$;

L is either a single covalent bond or represents a divalent unit selected from the group consisting of —C(O)—, —Ar$^2$—C(O)— and —Ar$^2$—, where, in the case where the divalent unit is —Ar$^2$—C(O)—, the group Ar$^2$ is bonded to N and C(O) is bonded to the group Ar$^1$;

Ar$^2$ is a divalent mono- or polycyclic aromatic or heteroaromatic unit having 5 to 40 aromatic ring atoms optionally substituted by one or more radicals $R^{4a}$ or $R^{4b}$;

$R^1$ and $R^2$
- are selected, identically or differently on each occurrence, from the group consisting of H, D, F, Cl, Br, I, $N(Ar^3)_2$, $C(=O)Ar^3$, $P(=O)(Ar^3)_2$, $S(=O)Ar^3$, $S(=O)_2Ar^3$, CN, a straight-chain alkyl, alkoxy or thioalkoxy group having 1 to 40 C atoms, a branched or cyclic alkyl, alkoxy or thioalkoxy group having 3 to 40 C atoms, or an alkenyl or alkynyl group having 2 to 40 C atoms, each of which is optionally substituted by one or more radicals $R^5$ and where in each case one or more non-adjacent $CH_2$ groups are optionally replaced by $R^5C=CR^5$, $C\equiv C$, $C=O$, $C=S$, $P(=O)(R^5)$, SO, $SO_2$, $NR^5$, O, S, or $CONR^5$ and where one or more H atoms are optionally replaced by D, F, Cl, Br, I, CN, or $NO_2$, or a mono- or polycyclic aromatic ring system having 5 to 40 aromatic ring atoms, which in each case are optionally substituted by one or more radicals $R^6$, or an aryloxy or heteroaryloxy group having 5 to 40 aromatic ring atoms, which are optionally substituted by one or more radicals $R^5$, or a combination of these systems; wherein two or more adjacent substituents $R^1$ and/or $R^2$ are optionally linked to one another via a single covalent bond or a divalent group Z;

$R^3$ is selected, identically or differently on each occurrence, from the group consisting of H, D, F, Cl, Br, I, $N(Ar^3)_2$, $C(=O)Ar^3$, $P(=O)(Ar^3)_2$, $S(=O)Ar^3$, $S(=O)_2Ar^3$, $CR^5=CR^5Ar^3$, CN, $NO_2$, $Si(R^5)_3$, $B(OR^5)_2$, $OSO_2R^5$, a straight-chain alkyl, alkoxy or thioalkoxy group having 1 to 40 C atoms, a branched or cyclic alkyl, alkoxy or thioalkoxy group having 3 to 40 C atoms, or an alkenyl or alkynyl group having 2 to 40 C atoms, each of which is optionally substituted by one or more radicals $R^5$ and where in each case one or more non-adjacent $CH_2$ groups is optionally replaced by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S, or $CONR^5$ and where one or more H atoms is optionally replaced by D, F, Cl, Br, I, CN, or $NO_2$, or a mono- or polycyclic aromatic or heteroaromatic ring system having 5 to 40 aromatic ring atoms, which in each case is optionally substituted by one or more radicals $R^6$, or an aryloxy or heteroaryloxy group having 5 to 40 aromatic ring atoms, which is optionally substituted by one or more radicals $R^5$, or a combination of these systems; wherein two or more adjacent substituents $R^3$ are optionally linked to one another via a single covalent bond or a divalent group Z;

$R^{4a}$
- is selected, from the group consisting of D, F, Cl, Br, I, CN, a straight-chain alkyl, alkoxy or thioalkoxy group having 1 to 40 C atoms, a branched or cyclic alkyl, alkoxy or thioalkoxy group having 3 to 40 C atoms, or an alkenyl or alkynyl group having 2 to 40 C atoms, each of which is optionally substituted by one or more radicals $R^5$ and where in each case one or more non-adjacent $CH_2$ groups is optionally replaced by $R^5C=CR^5$, $C\equiv C$, $C=O$, $C=S$, $P(=O)(R^5)$, SO, $SO_2$, $NR^5$, O, S or $CONR^5$ and where one or more H atoms is optionally replaced by D, F, Cl, Br, I, CN or $NO_2$, or a mono- or polycyclic aromatic ring system having 5 to 40 aromatic ring atoms, which in each case is optionally substituted by one or more radicals $R^6$, or an aryloxy or heteroaryloxy group having 5 to 40 aromatic ring atoms, which is optionally substituted by one or more radicals $R^5$, or a combination of these systems; wherein two or more adjacent substituents $R^{4a}$ or $R^{4b}$ are optionally linked to one another via a single covalent bond or a divalent group Z;

$R^{4b}$
- is selected from the group consisting of D, F, Cl, Br, I, $N(Ar^3)_2$, $C(=O)Ar^3$, $P(=O)(Ar^3)_2$, $S(=O)Ar^3$, $S(=O)_2Ar^3$, CN, a straight-chain alkyl, alkoxy or thioalkoxy group having 1 to 40 C atoms, a branched or cyclic alkyl, alkoxy or thioalkoxy group having 3 to 40 C atoms, or an alkenyl or alkynyl group having 2 to 40 C atoms, each of which is optionally substituted by one or more radicals $R^5$ and where in each case one or more non-adjacent $CH_2$ groups is optionally replaced by $R^5C=CR^5$, $C\equiv C$, $C=O$, $C=S$, $P(=O)(R^5)$, SO, $SO_2$, $NR^5$, O, S or $CONR^5$ and where one or more H atoms is optionally replaced by D, F, Cl, Br, I, CN or $NO_2$, or a mono- or polycyclic aromatic or heteroaromatic ring system having 5 to 40 aromatic ring atoms, which in each case is optionally substituted by one or more radicals $R^6$, or an aryloxy or heteroaryloxy group having 5 to 40 aromatic ring atoms, which is optionally substituted by one or more radicals $R^5$, or a combination of these systems; wherein two or more adjacent substituents $R^{4a}$ or $R^{4b}$ are optionally linked to one another via a single covalent bond or a divalent group Z;

$Ar^3$ is a mono- or polycyclic aromatic or heteroaromatic ring system having 5 to 40 aromatic ring atoms, which in each case is optionally substituted by one or more radicals $R^6$;

$R^5$ is, identically or differently on each occurrence, H, D, a straight-chain alkyl group having 1 to 20 C atoms, or a branched or cyclic alkyl group having 3 to 20 C atoms, where one or more non-adjacent $CH_2$ groups are optionally replaced by NH, O or S and where one or more H atoms are optionally replaced by F, or a mono- or polycyclic aromatic or heteroaromatic ring system having 5 to 20 aromatic ring atoms, which in each case is optionally substituted by one or more radicals $R^6$; wherein two or more substituents $R^5$ are optionally linked to one another via a single covalent bond or a divalent group Z;

$R^6$ is, identically or differently on each occurrence, H, D, F, CN, a straight-chain alkyl group having 1 to 20 C atoms, or a branched or cyclic alkyl group having 3 to 20 C atoms, where one or more non-adjacent $CH_2$ groups are optionally replaced by NH, O or S and where one or more H atoms are optionally replaced by F; wherein two or more substituents $R^6$ are optionally linked to one another via a single covalent bond or a divalent group Z;

Z is a divalent group $—(CH_2)_q—$, wherein q is equal to 1, 2, 3, 4, or 5.

2. The compound of claim 1, wherein Y is, identically or differently on each occurrence, $CR^2$ and W is, identically or differently on each occurrence, $CR^1$.

3. The compound of claim 1, wherein E is either a single covalent bond or a divalent unit selected from $N(R^3)$, $C(R^3)_2$, O, and S.

4. The compound of claim 1, wherein X is, identically or differently on each occurrence, a divalent unit selected from the group consisting of $C(R^3)_2$, S, and O.

5. The compound of claim 1, wherein Ar is a divalent or trivalent mono- or polycyclic aromatic or heteroaromatic unit having 5 to 10 aromatic ring atoms optionally substituted by one or more radicals $R^{4a}$.

6. The compound of claim 1, wherein $Ar^1$ represents an electron-deficient, mono- or polycyclic heteroaromatic group having 5 to 10 aromatic ring atoms optionally substituted by one or more radicals $R^{4b}$.

7. The compound of claim 6, wherein $Ar^1$ is selected from the group consisting of pyridine, pyrazine, pyrimidine, pyridazine, 1,2,4-triazine, 1,3,5-triazine, quinoline, isoquinoline, quinoxaline, pyrazole, imidazole, benzimidazole, thiazole, benzothiazole, oxazole, and benzoxazole, each of which is optionally substituted by $R^{4b}$.

8. The compound of claim 1, wherein L is a single covalent bond or a divalent unit —$Ar^2$— optionally substituted by one or more radicals $R^{4a}$ or $R^{4b}$.

9. The compound of claim 1, wherein the sum of the indices n+m=1.

10. A process for preparing the compound of claim 1, comprising the steps of:
   a) coupling a carbazole derivative or fluorene derivative to a benzene derivative, and
   b) arylating the carbazole nitrogen to introduce $Ar^1$.

11. A polymer, oligomer, or dendrimer comprising one or more compounds of claim 1, wherein one or more radicals or H atoms of said compounds is a bond to said polymer, oligomer, or dendrimer.

12. An electronic device comprising the compound of claim 1 or a polymer, oligomer, or dendrimer of claim 11.

13. The electronic device of claim 12, wherein said electronic device is selected from the group consisting of organic electroluminescent devices, organic field-effect transistors, organic thin-film transistors, organic light-emitting transistors, organic integrated circuits, organic solar cells, organic field-quench devices, light-emitting electrochemical cells, organic photoreceptors, and organic laser diodes.

14. The electronic device of claim 13, wherein said electronic device is an organic electroluminescent device and wherein said compound of claim 1 or a polymer, oligomer, or dendrimer comprising one or more compounds of claim 1 is employed as matrix material for phosphorescent dopants in an emitting layer and/or as electron-transport material in an electron-transport layer and/or as hole-transport material in a hole-transport layer and/or as hole-blocking material in a hole-blocking layer.

15. A mixture of one or more compounds of claim 1 and/or one or more polymers, oligomers, or dendrimers of claim 11 with one or more emitting compounds.

16. A formulation comprising at least one compound of claim 1 and/or a polymer, oligomer, or dendrimer of claim 11 or a mixture of claim 15 and at least one organic solvent.

* * * * *